US008846866B2

(12) United States Patent
Carrico et al.

(10) Patent No.: US 8,846,866 B2
(45) Date of Patent: Sep. 30, 2014

(54) ALDEHYDE TAGS, USES THEREOF IN SITE-SPECIFIC PROTEIN MODIFICATION

(71) Applicant: The Regents of the University of California, Oakland, CA (US)

(72) Inventors: Isaac S. Carrico, Stony Brook, NY (US); Brian L. Carlson, Richmond, CA (US); Peng Wu, Berkeley, CA (US); Carolyn Bertozzi, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/708,528

(22) Filed: Dec. 7, 2012

(65) Prior Publication Data
US 2013/0203111 A1 Aug. 8, 2013

Related U.S. Application Data

(60) Continuation of application No. 13/163,574, filed on Jun. 17, 2011, now Pat. No. 8,349,910, which is a division of application No. 11/857,385, filed on Sep. 18, 2007, now Pat. No. 7,985,783.

(60) Provisional application No. 60/846,644, filed on Sep. 21, 2006.

(51) Int. Cl.
*C07K 1/00* (2006.01)
*C07K 16/00* (2006.01)
*A61L 33/00* (2006.01)
*C07K 1/13* (2006.01)
*C07K 1/107* (2006.01)
*C07K 14/00* (2006.01)
*C12P 21/00* (2006.01)
*C07K 16/46* (2006.01)
*C12N 9/96* (2006.01)

(52) U.S. Cl.
CPC .............. *C07K 1/1072* (2013.01); *C07K 1/13* (2013.01); *C07K 14/00* (2013.01); *C07K 1/006* (2013.01); *C12P 21/005* (2013.01); *C07K 16/46* (2013.01); *C12P 21/00* (2013.01); *C12N 9/96* (2013.01)
USPC .......................... 530/350; 530/387.1; 522/87

(58) Field of Classification Search
USPC ........................................................ 530/350
See application file for complete search history.

(56) References Cited

U.S. PATENT DOCUMENTS 5,204,449 A 4/1993 Puri
6,900,304 B2 5/2005 Tsien et al.
(Continued)

FOREIGN PATENT DOCUMENTS

WO WO 2005113765 12/2005
WO WO 2008/036350 * 3/2008
WO WO 2009120611 10/2009

OTHER PUBLICATIONS

Adams, et al., "New Biarsenical Ligands and Tetracysteine Labeling in Vitro and in Vivo: Synthesis Applications" *J. Amer. Chem. Soc.* 124(21), (2002):6063-6076.

(Continued)

*Primary Examiner* — Alexander Kim
(74) *Attorney, Agent, or Firm* — Carol L. Francis; Rudy J. Ng; Bozicevic, Field & Francis LLP

(57) ABSTRACT

The invention features compositions and methods for site-specific modification of proteins by incorporation of an aldehyde tag. Enzymatic modification at a sulfatase motif of the aldehyde tag through action of a formylglycine generating enzyme (FGE) generates a formylglycine (FGly) residue. The aldehyde moiety of FGly residue can be exploited as a chemical handle for site-specific attachment of a moiety of interest to a polypeptide.

49 Claims, 26 Drawing Sheets

(56) References Cited

U.S. PATENT DOCUMENTS

| | | |
|---|---|---|
| 7,985,783 B2 | 7/2011 | Carrico et al. |
| 8,097,701 B2 | 1/2012 | Carrico et al. |
| 8,349,910 B2 | 1/2013 | Carrico et al. |
| 2002/0146504 A1 | 10/2002 | Schwartz |
| 2003/0186229 A1 | 10/2003 | Tsien et al. |
| 2004/0229250 A1 | 11/2004 | Figura et al. |
| 2005/0026234 A1 | 2/2005 | Violin et al. |
| 2006/0035305 A1 | 2/2006 | Bertozzi |
| 2011/0117621 A1 | 5/2011 | Rush et al. |

OTHER PUBLICATIONS

Banghart, et al., "Light-Activated Ion Channels for Remote Control of Neuronal Firing" *Nat. Neurosci.* 7(12), (2004):1381-6.

Berteau, et al., "A New Type of Bacterial Sulfatase Reveals a Novel Maturation Pathway in Prokaryotes" *J Biol Chem.* 281(32) (2006):22464-70.

Chen et al., "Synthetic Erythropoietic Proteins: Tuning Biological Performance by Site-Specific Polymer Attachment" *Chem. Biol.* 12(3), (2005):371-383.

Chen, et al., "Site-Specific Labeling of Cell Surface Proteins with Biophysical Probes Using Biotin Ligase" *Nature Methods* 2(2), (2005):99-104.

Cosma, et al., "The Multiple Sulfatase Deficiency Gene Encodes an Essential and Limiting Factor for the Activity of Sulfatases" *Cell* 113(4), (2003):445-56.

Dierks, et al., "Conversion of Cysteine to Formylglycine in Eukaryotic Sulfatases Occurs by a Common Mechanism in the Endoplasmic Reticulum" *FEBS Lett.* 423(1), (1998):61-5.

Dierks, et al., "Conversion of Cysteine to Formylglycine: A Protein Modification in the Endoplasmic Reticulum" *Proc Natl Acad Sci USA*, 94(22), (1997):11963-8.

Dierks, et al., "Molecular Basis for Multiple Sulfatase Deficiency and Mechanism for Formylglycine Generation of the Human Formylglycine-Generating Enzyme" *Cell* 121(4), (2005):541-52.

Dierks, et al., "Posttranslational Formation of Formylglycine in Prokaryotic Sulfatases by Modification of Either Cysteine or Serine" *J Biol Chem*, 273(40), (1998):25560-25564.

Fang, et al., "Post-Translational Formylglycine Modification of Bacterial Sulfatases by the Radical S-Adenosylmethionine Protein AtsB" *J Biol Chem.* 279(15), (2004):14570-8 [Epub Jan. 2, 2004].

GenBank Acc. No. NP_215226 (Jan. 6, 2005).

GenBank Acc. No. NP_215226 (May 24, 2007).

George, et al. "Specific Labeling of Cell Surface Proteins with Chemically Diverse Compounds" *J. Amer. Chem. Soc.* 126(29), (2004):8896-8897.

Griffin, et al., "Specific Covalent Labeling of Recombinant Protein Molecules Inside Live Cells" *Science* 281(5374), (1998):269-272.

Guignet, et al., "Reversible Site-Selective Labeling of Membrane Proteins in Live Cells" *Nature Biotechnol.* 22(4), (2004):440-444.

Knaust et al., "Residues Critical for Formylglycine Formation and/or Catalytic Activity of Arylsulfatase A," Biochemistry, 37(40), (1998):13941-13946.

Landgrebe, et al., "The Human SUMF1 Gene, Required for Post-translational Sulfatase Modification, Defines a New Gene Family Which Is Conserved from Pro- to Eukaryotes" *Gene* 316, (2003):47-56.

Lemieux, et al., "Chemoselective Ligation Reactions with Proteins, Oligosaccharides and Cells" *Trends Biotechnol* 16(12), (1998):506-13.

Lisenbee, et al., "Overexpression and Mislocalization of a Tail-Anchored GFP Redefines the Identity of Peroxisomal ER" *Traffic* 4(7), (2003):491-501.

Mariappan, et al., "Expression, Localization, Structural, and Functional Characterization of pFGE, the Paralog of the Cα-Formylglycine-generating Enzyme" *J. Biol. Chem.* 280(15), (2005):15173-9.

Mougous et al., "Identification, Function and Structure of the Mycobacterial Sulfotransferase that Initiates Sulfolipid-1 Biosynthesis" *Nat. Struc. Mol. Biol.* 11(8), (2004):721-729.

Preusser, et al., "Molecular Characterization of the Human Cα-formylglycine-generating Enzyme" *J. Biol. Chem.* 280(15), (2005):14900-10.

Roeser, et al., "A General Binding Mechanism for All Human Sulfatases by the Formylglycine-Generating Enzyme" *Proc Natl Acad Sci USA* 103(1), (2006):81-6.

Rush, et al., "An α-Formylglycine Building Block for Fmoc-Based Solid-Phase Peptide Synthesis" *Org Lett.* 8(1), (2006):131-4.

Samuel, et al., "Chemical Tools for the Study of Polysialic Acid", (2004) *Trends in Glycoscience and Technology* 16(91), (2004):305-318.

Sardiello et al., "Sulfatases and Sulfatase Modifying Factors: An Exclusive and Promiscuous Relationship" *Human Mol. Genet.* 14(21), (2005)3203-3217.

Schirmer, et al., "Computational Analysis of Bacterial Sulfatases and Their Modifying Enzymes", *Chem Biol* 5(8), (1998):R181-R186.

Schmidt, et al., "A Novel Amino Acid Modification in Sulfatases that Is Defective in Multiple Sulfatase Deficiency" *Cell* 82(2), (1995):271-8.

Stroffekova, et al. "The Protein-Labeling Reagent FLASH-EDT2 Binds Not Only to CCXXCC Motifs but Also Non-Specifically to Endogenous Cysteine-Rich Proteins" *Archiv-Europ. J. Physiol.* 442(6), (2001):859-866.

Szameit, et al., "The Iron Sulfur Protein AtsB Is Required for Post-translational Formation of Formylglycine in the Klebsiella Sulfatase" *J Biol Chem* 274(22), (1999):15375-81.

Villani et al., "Expression of Five Iduronate-2-Sulfatase Site-Directed Mutations" Biochimica et Biophysica Acta 1501(2-3), (2000):71-80.

Yin, et al., "Genetically Encoded Short Peptide Tag for Versatile Protein Labeling by Sfp Phosphopantetheinyl Transferase" *Proc. Natl. Acad. Sci. USA* 102(44), (2005):15815-15820.

Carrico, et al., "Introducing genetically encoded aldehydes into proteins" Nature Chemical Biology, 3(6), (2007):321-322.

Dierks, et al., "Multiple Sulfatase Deficiency Is Caused by Mutations in the Gene Encoding the Human Cα-Formylglycine Generating Enzyme" *Cell* 113(4), (2003):435-44.

Dierks, et al., "Sequence Determinants Directing Conversion of Cysteine to Formylglycine in Eukaryotic Sulfatases" *EMBO J* 18(8), (1999):2084-91.

Figura, et al. "A Novel Protein Modification Generating an Aldehyde Group in Sulfatases: Its Role in Catalysis and Disease" *Bioessays.* 20(6), (1998):505-10.

Lukatela, et al., "Crystal Structure of Human Arylsulfatase A: the Aldehyde Function and the Metal ion at the Active Site Suggest a Novel Mechanism for Sulfate Ester Hydrolysis" Biochemistry 37(11), (1998):3654-3664.

Prescher, et al., "Chemistry in Living Systems" Nat. Chem. Biol. 1(1), (2005):13-21.

Takakusaki et al. (2005) "Coexpression of Formylglycine-Generating Enzyme is Essential for Synthesis and Secretion of Functional Arylsulfatase A in a Mouse Model of Metachromatic Leukodystrophy" *Human Gene Ther* 16(8):929-936.

Tirat et al., "Evaluation of Two Novel Tag-Based Labelling Technologies for Site-Specific modification of Proteins" International Journal of Biological Macromolecules 39(1-3), (2006):66-76.

\* cited by examiner

FIG. 1B

```
H. sapiens Arylsulfatase E   (82) AASLCTPSRAAFLTGRYPV
       M. musculus Sulf2     (84) TTPMCCPSRSSILTGKYVH
          C. elegans Sul3    (75) VNQLCTPIRSAFMTGYYPF
     M. tuberculosis AtsG    (54) TAPLCTPSRGSLFTGRYPQ
             E. coli YidJ    (48) CSPVCTPARAGLFTGIYAN
       S. coelicolor SCO7547 (84) PTAICTPARASLLTGQAPF
          M. barkeri A3073   (80) TTALCSPSRSCILTGRNHH
```

6-mer tag
     Consensus         LCTPSRGSLFTG
                       R
                         13-mer tag

FIG. 12

|  | Concentration (ppb) | Standard Deviation (ppb) | Molarity (μM) | Metal / FGE ratio |
|---|---|---|---|---|
| *Strep* FGE[a] | 382,522 | 6,317 | 10.19 | -- |
| Ca | 496.56 | 16.69 | 12.39 | 1.22 ± 0.04 |
| Cu | 3.81 | 1.87 | 0.06 | 0 |
| Fe | 0.52 | 1.60 | 0.01 | 0 |
| Mg | -1.34 | 0.34 | -0.06 | 0 |
| Mn | -1.39 | 1.04 | -0.03 | 0 |
| Zn | 0.97 | 0.43 | 0.01 | 0 |
| | | | | |
| *Mtb* FGE[b] | 214,071 | 6,843 | 6.54 | -- |
| Ca | 37.58 | 39.91 | 0.93 | 0.14 ± 0.15 |
| Cu | 7.67 | 2.93 | 0.12 | 0 |
| Fe | 2.64 | 1.70 | 0.04 | 0 |
| Mg | -1.30 | 0.41 | -0.05 | 0 |
| Mn | -0.95 | 1.16 | -0.02 | 0 |
| Zn | 5.93 | 0.55 | 0.09 | 0 |

[a]His$_6$-tagged *Strep* FGE molecular weight = 37,540.35

[b]His$_6$-tagged *Mtb* FGE molecular weight = 35,015.44

- IFN-Beta: five α-helices (A-E) with a single glycosylation site existing at residue Asn-80

ALDEHYDE TAGS, USES THEREOF IN SITE-SPECIFIC PROTEIN MODIFICATION

CROSS-REFERENCE TO RELATED APPLICATIONS

This application is a continuation of U.S. application Ser. No. 13/163,574, filed Jun. 17, 2011, which is a divisional of U.S. application Ser. No. 11/857,385, filed Sep. 18, 2007, which claims priority benefit of U.S. provisional application Ser. No. 60/846,644, filed Sep. 21, 2006, each of which applications are incorporated herein by reference in their entirety.

GOVERNMENT RIGHTS

This invention was made with government support under federal grant no. R01-AI051622 awarded by National Institutes of Health. The United States Government has certain rights in this invention.

BACKGROUND

Site-specific labeling of proteins is an important as a tool for the dissection of biochemical and cellular networks. A variety of technologies have been developed to address this need. One such technology used for protein localization and tracking is labeling with fluorescent proteins, such as green fluorescent protein (GFP). However, the size of these fluorescent proteins can interfere with the trafficking, localization and protein-protein interactions of the target (Lisenbee et al. Traffic 2003, 4, (7), 491-501).

As a result, many groups have focused their attention on using smaller fusions to direct specific secondary labeling reagents. FlAsH, developed by Roger Tsien and colleagues, utilizes the interaction between specifically arranged tetracysteine motifs and biarsenyl-fluorophores (Chen et al. Science 1998, 281, (5374), 269-272). Despite picomolar affinity between the minimal 8 amino acid sequence and bi-arsenical probes (Adams et al. J. Amer. Chem. Soc. 2002, 124, (21), 6063-6076), background due to native cysteine motifs remains a problem (Stroffekova et al. Pflugers Archiv-Eur. J. Physiol. 2001, 442, (6), 859-866).

To increase specificity, peptide targeting motifs that depend upon secondary labeling by enzymes have been explored. One such strategy depends upon the fusion with $O^6$-alkylguanine-DNA transferase (hAGT), which can ligate a wide variety of small molecules to an internal cysteine. While hAGT fusions allow very specific, covalent attachment of a wide variety of small molecule probes it relies upon a 207 amino acid fusion (George et al. J. Amer. Chem. Soc. 2004, 126, (29), 8896-8897; Guignet et al. Nature Biotechnol 2004, 22, (4), 440-444). In a separate approach, protein fusions with the approximately 80 amino acid acyl carrier protein can be specifically labeled with CoA-derived probes using the enzyme phosphopantetheine transferase. Alternatively, biotin ligase has been used to transfer biotin or a ketone-containing biotin isostere to a 15 amino acid acceptor peptide. Appendage of the ketone isostere allows the formation of hydrazones and oxime conjugates.

There is a need for new approaches for site-specific modification of proteins.

LITERATURE

Adams et al. 2002 J. Amer. Chem. Soc. 2002, 124, (21), 6063-6076; Banghart et al. 2004 Nat. Neurosci. 7(12):1381-6. Epub 2004 Nov. 21; Berteau et al. 2006 J Biol Chem. 281(32):22464-70 (Epub 2006 Jun. 9); Chen et al. 2005 Nature Methods 2005, 2, (2), 99-104; Cosma et al. 2003 Cell 113, (4), 445-56; Dierks et al. 1997 Proc Natl Acad Sci USA 94, (22), 11963-8; Dierks et al. 2003 Cell 113, (4), 435-44; Dierks et al. 2005 Cell 121, (4), 541-52; George et al. 2004 J. Amer. Chem. Soc. 126, (29), 8896-8897; Griffin et al. 1998 Science 281, (5374), 269-272; Guignet et al. 2004 Nature Biotechnol. 22, (4), 440-444; Landgrebe et al. 2003 Gene 316:47-56; Lemieux (1998) *Trends Biotechnol* 16, 506-13; Lisenbee et al. 2003 Traffic 4, (7), 491-501; Mariappan et al. 2005 J. Biol. Chem. 280(15):15173-9 (Epub 2005 Feb. 11); Mougous et al. 2004 Nat. Struc. Mol. Biol. 11, 721-729; Preusser et al. 2005 J. Biol. Chem. 280(15):14900-10 (Epub 2005 Jan. 18); Roeser et al. 2006 Proc Natl Acad Sci USA 103(1):81-6 (Epub 2005 Dec. 20); Rush et al. (Jan. 5 2006) Org Lett. 8(1):131-4; Sardiello et al. 2005 Human Mol. Genet. 14, 3203-3217; Schirmer et al. 1998 Chemistry & Biology 5, R181-R186; Schmidt et al. 1995 Cell 82, (2), 271-8; Stroffekova et al. 2001 Archiv-Europ. J. Physiol. 442, (6), 859-866; Szameit et al. 1999 J Biol Chem 274, (22), 15375-81; Yin, J. et al. 2005 Proc. Natl. Acad. Sci. USA 102, 15815-15820 (2005); US20050026234; US20030186229; and U.S. Pat. No. 6,900,304.

SUMMARY

The invention features compositions and methods for site-specific modification of proteins by incorporation of an aldehyde tag. Enzymatic modification at a sulfatase motif of the aldehyde tag through action of a formylglycine generating enzyme (FGE) generates a formylglycine (FGly) residue. The aldehyde moiety of FGly residue can be exploited as a chemical handle for site-specific attachment of a moiety of interest to a polypeptide.

Accordingly, the present disclosure provides methods for modifying a polypeptide, the method comprising contacting a polypeptide comprising a converted sulfatase motif with a reactive partner comprising a moiety of interest, wherein the converted sulfatase motif comprises:

$$X_1(FGly)X_2Z_2X_3R \qquad (I)$$

where
FGly is a formylglycine residue;
$Z_2$ is a proline or alanine residue;
$X_1$ is present or absent and, when present, is any amino acid, with the proviso that when the heterologous sulfatase motif is at an N-terminus of the polypeptide, $X_1$ is present; and
$X_2$ and $X_3$ are each independently any amino acid;
wherein said contacting is under conditions sufficient for conjugation of the moiety of interest of the reactive partner to FGly of the polypeptide, thereby producing a modified polypeptide.

The sulfatase motif can be a heterologous sulfatase motif. Furthermore, the FGly residue can be positioned at an internal sequence of the polypeptide, and/or positioned at a terminal loop, a C-terminus, or an N-terminus of the polypeptide. Of particular interest are situations in which the FGly residue is present on a solvent-accessible region of the polypeptide when folded. Further of interest are situations in which the FGly residue is present at a site of post-translational modification of the polypeptide, such as a glycosylation site. These sties of post-translation modification can be native to the parent polypeptide, or the polypeptide can be engineered to include one or more non-native sites of post-translational modification, and the heterologous sulfatase motif is positioned at said one or more non-native sites of post-translational modification.

Of particular interest are sulfatase motifs where $X_1$, when present, is L, M, V, S or T. Further sulfatase motifs of particular interest are those where $X_2$ and $X_3$ are each independently an aliphatic amino acid, a polar, uncharged amino acid, or a sulfur containing amino acid (i.e., other than a aromatic amino acid or a charged amino acid), and in certain embodiments are each independently S, T, A, V, G or C.

The present disclosure also provides methods for producing a formylglycine in a polypeptide, the method comprising contacting a polypeptide comprising a heterologous sulfatase motif with a formylglycine generating enzyme (FGE), wherein the heterologous sulfatase motif of the formula

 (I)

where
$Z_1$ is cysteine or serine;
$Z_2$ is a proline or alanine residue;
$X_1$ may be present or absent and, when present, is any amino acid, with the proviso that when the heterologous sulfatase motif is at an N-terminus of the polypeptide, $X_1$ is present;
$X_2$ and $X_3$ are independently any amino acid,
wherein said contacting is under conditions sufficient for conversion of $Z_1$ to a formylglycine (FGly) residue in the polypeptide and produces a converted aldehyde tagged polypeptide.

The polypeptide used in this method can have at least one of the following properties: the heterologous sulfatase motif is less than 16 amino acid residues in length, the heterologous sulfatase motif is positioned at an N-terminus of the polypeptide, the heterologous sulfatase motif is positioned at an internal site of an amino acid sequence native to the polypeptide, the heterologous sulfatase motif is positioned in a terminal loop of the polypeptide, the heterologous sulfatase motif positioned at a site of post-translational modification of the polypeptide; the polypeptide is a full-length polypeptide, the polypeptide is other than a preprolactin polypeptide, a prolactin polypeptide, or a glutathione-S-transferase polypeptide.

The heterologous sulfatase motif can be less than 16 amino acid residues in length and can be positioned at a C-terminus of the polypeptide. The heterologous sulfatase motif can be present at an internal site in a terminal loop of the polypeptide and/or is present at an internal site within an extracellular loop or an intracellular loop. The heterologous sulfatase motif can be present at an internal site or at the N-terminus, and/or can be solvent-accessible when the polypeptide is folded. The heterologous sulfatase motif can be present at a site of post-translational modification, such as a glycosylation site. The site of post-translational modification can be native to the parent target polypeptide or the target polypeptide can be engineered to include one or more non-native sites of post-translational modification, and wherein the heterologous sulfatase motif is positioned at said one or more non-native sites of post-translational modification.

Of particular interest are sulfatase motifs where $X_1$, when present, is an aliphatic amino acid, a sulfur-containing amino acid, or a polar, uncharged amino acid, (i.e., other than a aromatic amino acid or a charged amino acid), and may in certain embodiments be L, M, V, S or T. Further sulfatase motifs of particular interest are those where $X_2$ and $X_3$ are each independently an aliphatic amino acid, a polar, uncharged amino acid, or a sulfur containing amino acid (i.e., other than a aromatic amino acid or a charged amino acid), and in certain embodiments are each independently S, T, A, V G or C. In one embodiments of interest, the polypeptide is expressed in a cell containing the FGE.

In further embodiments, the method further comprises contacting the converted aldehyde tagged polypeptide with a reactive partner comprising a moiety of interest; wherein said contacting is under conditions to provide for production of a reaction product of a modified aldehyde tagged polypeptide having the moiety of interest covalently bound to the FGly residue of the heterologous sulfatase motif. The moiety of interest can be, e.g., a water-soluble polymer, a detectable label, a drug, or a moiety for immobilization of the polypeptide in a membrane or on a surface.

The disclosure also provides a converted aldehyde tagged polypeptide produced by the methods described herein, as well as a modified aldehyde tagged polypeptide produced by the methods described herein.

The disclosure further provides polypeptides comprising a heterologous sulfatase motif having a formylglycine generating enzyme (FGE), wherein the heterologous sulfatase motif comprises

 (I)

where
FGly is a formylglycine residue;
$Z_2$ is a proline or alanine residue;
$X_1$ may be present or absent and, when present, is any amino acid, with the proviso that when the heterologous sulfatase motif is at an N-terminus of the aldehyde tagged polypeptide, $X_1$ is present; and
$X_2$ is any amino acid;

The polypeptide used in this method can have at least one of the following properties: the heterologous sulfatase motif is less than 16 amino acid residues in length, the heterologous sulfatase motif is positioned at an N-terminus of the polypeptide, the heterologous sulfatase motif is positioned at an internal site of an amino acid sequence native to the polypeptide, the heterologous sulfatase motif is positioned in a terminal loop of the polypeptide, the heterologous sulfatase motif is position at a site of post-translational modification of the polypeptide; the polypeptide is a full-length polypeptide, or the polypeptide is other than a preprolactin polypeptide, a prolactin polypeptide, or a glutathione-S-transferase polypeptide.

The heterologous sulfatase motif of such polypeptides can be less than 16 amino acid residues in length and can be positioned at a C-terminus of the polypeptide. The heterologous sulfatase motif can be present in a terminal loop of the polypeptide. The polypeptide can be a transmembrane protein with the heterologous sulfatase motif present at an internal site within an extracellular loop or an intracellular loop. The heterologous sulfatase motif of the polypeptide can be present at an internal site or at the N-terminus of the polypeptide, and is solvent-accessible when the polypeptide is folded. Further, the heterologous sulfatase motif can be present at a site of post-translational modification, such as a glycosylation site. The site of post-translational modification can be native to the parent target polypeptide or the target polypeptide can be engineered to include one or more non-native sites of post-translational modification, and wherein the heterologous sulfatase motif is positioned at said one or more non-native sites of post-translational modification. Of particular interest are sulfatase motifs where $X_1$, when present, is though usually an aliphatic amino acid, a sulfur-containing amino acid, or a polar, uncharged amino acid, (i.e., other than a aromatic amino acid or a charged amino acid), and in certain embodiments is L, M, V, S or T. Further sulfatase motifs of particular interest are those where $X_2$ and $X_3$ are each independently an aliphatic amino acid, a polar, uncharged amino acid, or a sulfur containing amino acid (i.e., other than a aromatic amino acid or a charged amino acid), and in certain embodiments are each independently S, T, A, V, G or C.

The disclosure also contemplates nucleic acid molecules comprising a nucleotide sequence encoding such polypeptides, as well as vectors and recombinant host cells containing such nucleic acid molecules.

The disclosure also provides modified polypeptides comprising a formylglycine residue covalently attached to a moiety of interest, wherein the polypeptide comprises a modified sulfatase motif of the formula:

$$X_1(FGly')X_2Z_2X_3R \tag{I}$$

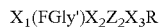

where

FGly' is the formylglycine residue having a heterologous, covalently attached moiety;

$Z_2$ is a proline or alanine residue;

$X_1$ may be present or absent and, when present, is any amino acid, usually an aliphatic amino acid, a sulfur-containing amino acid, or a polar, uncharged amino acid, (i.e., other than a aromatic amino acid or a charged amino acid), with the proviso that when the heterologous sulfatase motif is at an N-terminus of the polypeptide, $X_1$ is present; and $X_2$ is any amino acid.

The moiety of such modified polypeptides can be a water-soluble polymer, a detectable label, a drug, or a moiety for immobilization of the polypeptide in a membrane or on a surface. The modified sulfatase motif of such modified polypeptides can be positioned in the modified polypeptide at a site of post-translational modification of a parent of the modified polypeptide. The site of post-translation modification can be, e.g., a glycosylation site. The site of post-translational modification can be native to the parent target polypeptide or the target polypeptide can be engineered to include one or more non-native sites of post-translational modification, and wherein the heterologous sulfatase motif is positioned at said one or more non-native sites of post-translational modification.

The disclosure also provides recombinant nucleic acids comprising an expression cassette comprising a first nucleic acid comprising an aldehyde tag-encoding sequence; and a restriction site positioned 5' or 3' of the aldehyde tag-encoding sequence, which restriction site provides for insertion of a second nucleic acid encoding a polypeptide of interest; and a promoter operably linked to the expression cassette to provide for expression of an aldehyde tagged-polypeptide produced by insertion of the second nucleic acid encoding the polypeptide of interest into the restriction site.

The present disclosure also identifies the formylglycine generating enzyme (FGE) of *Mycobacterium tuberculosis* (Mtb FGE), and thus encompasses methods of its use and reaction mixtures comprising an isolated *Mycobacterium tuberculosis* formylglycine generating enzyme (FGE); and a polypeptide comprising a heterologous sulfatase motif of the formula:

$$X_1Z_1X_2Z_2X_3R \tag{I}$$

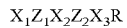

where $Z_1$ is cysteine or serine;

$Z_2$ is a proline or alanine residue;

$X_1$ is present or absent and, when present, is any amino acid, with the proviso that when the heterologous sulfatase motif is at an N-terminus of the polypeptide, $X_1$ is present;

$X_2$ and $X_3$ are each independently any amino acid; wherein the heterologous sulfatase motif of the formula.

The present disclosure also provides reaction mixtures of a polypeptide having a heterologous sulfatase motif as described herein and an FGE, which may further include a converted aldehyde tagged polypeptide in which a heterologous sulfatase motif of the polypeptide contains an FGly residue. The disclosure also provides compositions comprising an FGE and a converted aldehyde tagged polypeptide in which a heterologous sulfatase motif of the polypeptide contains an FGly residue. In related embodiments, such reaction mixtures may further include a reagent to facilitate attachment of a moiety of interest to a FGly residue of a polypeptide.

Other features of the invention and its related disclosure are provided below, and will be readily apparent to the ordinarily skilled artisan upon reading the present disclosure.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 1B is a schematic showing a sequence alignment of the sulfatase motif from a variety of sulfatases found in diverse organisms. The consensus sequence contains the sequence of the two aldehyde tags used in this study. Conserved residues are highlighted. From top to bottom; SEQ NO:85, SEQ ID NO:86, SEQ NO:87, SEQ ID NO:88, SEQ NO:89, SEQ ID NO:90, SEQ NO:91, and SEQ ID NO:55.

(FIG. 11A) Stereo superposition of Strep FGE and human FGE. Strep FGE secondary structure elements indicated. Ca2+ ions are rendered as spheres. Overall root mean square deviation is 0.65 Å. (FIG. 11B) Comparison of the residues surrounding Strep FGE's potential Ca2+ binding site and human FGE's second Ca2+ binding site. Proper coordination geometry is lost with a Glu66Ala mutation in Strep FGE. (FIG. 11C) Surface representation of Strep FGE's putative exosite. The surface, represented in grey scale, was is colored according to residue conservation between all known and putative FGE's (based on amino acid sequence alignment); white represents non-conserved residues, light blue represents weakly conserved residues, medium blue represents conserved residues, and dark blue represents identical residues. The 6-residue peptide substrate is modeled from the human FGE-peptide complex structure24 (PDB entry 2AIK). A hypothetical extended peptide substrate is represented as a ribbon. (FIGS. 11D and 11E) Active site cysteines 272 and 277 appear to exist in a partial disulfide bond. Cys272 is shown in two alternate conformations. Electron density between Cys272 and Ser269 can be modeled as a water molecule (FIG. 11D) or a hydroperoxide with partial occupancy (FIG. 11E). Monomer D is shown. Omit electron density is contoured at 1σ.

FIG. 12 is a table showing ICP-AES analysis of Strep FGE and Mtb FGE.

Cys301 was an additional surface exposed thiol that served as an internal control to assess labeling efficiency.

Figure 15:
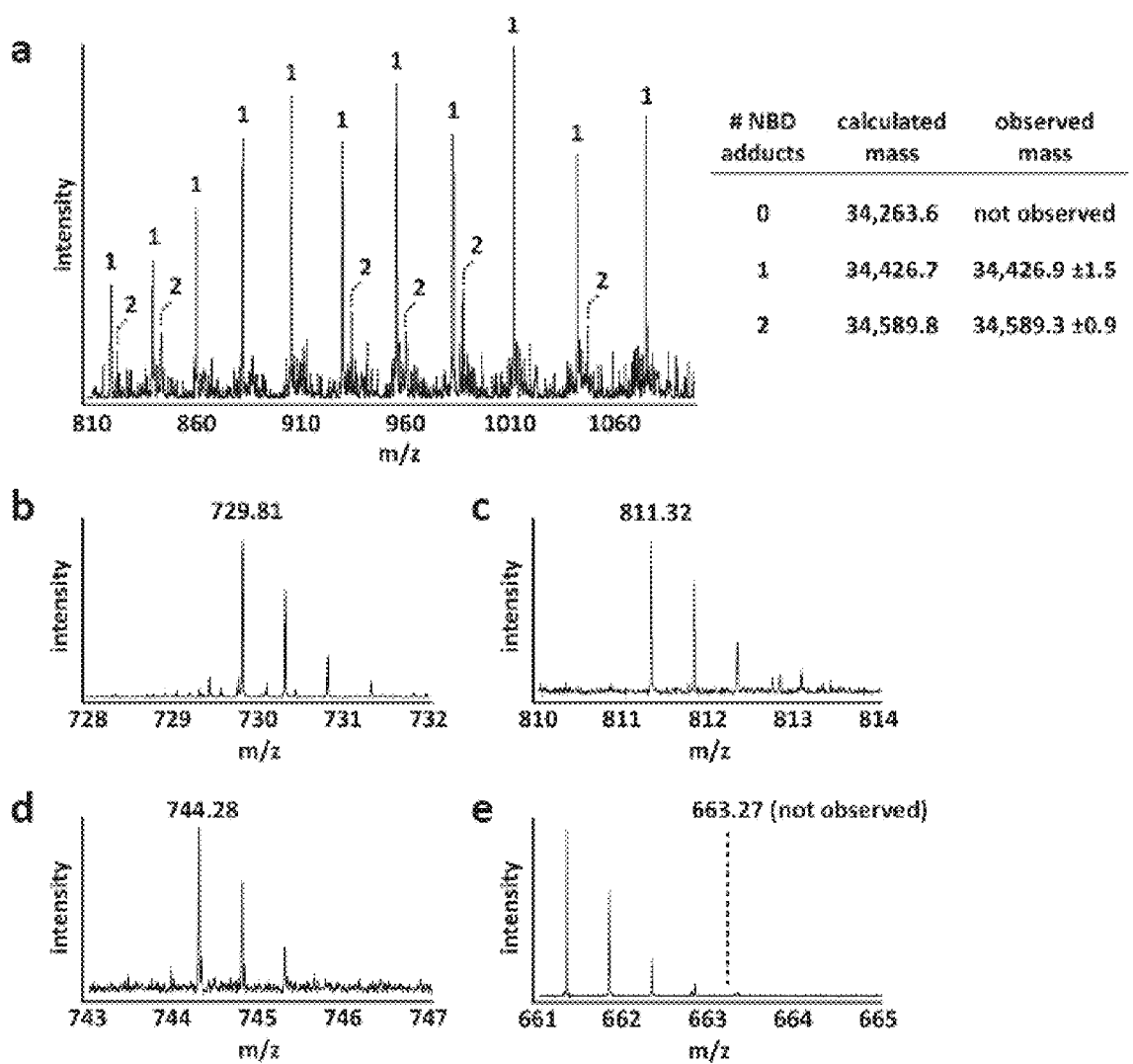

FIG. 15 provides data illustrating that a sub-population of Strep FGE Cys277Ser does not contain a reduced Cys272 residue. (a) Strep FGE Cys277Ser was labeled with NBD and adducts were detected by mass spectrometry. Two populations of NBD-modified Strep FGE Cys277Ser were observed. One population corresponds to Cys272 as a free thiol with a single NBD adduct on Cys301 (see b and d). The other population had NDB adducts at both Cys272 and Cys301 (see c and d). Multiple charge states are shown for both populations. Numbers above each ion peak indicate the number of NBD adducts attributed to each population. (b-d) NBD adducts were mapped to each surface-exposed thiol using mass spectrometry after trypsinolysis. Shown are the +2 charge state ions corresponding to Cys272 as a free thiol (b, calculated mass=1,457.61; observed mass=1,457.60), Cys272 with an NBD adduct (c, calculated mass=1,620.62; observed mass=1,620.60), and Cys301 with an NBD adduct (d, calculated mass=1,486.54; observed mass=1486.54). (e) Cys301 was not observed as a free thiol (expected position of +2 charge state ion shown). Cys301 was an additional surface exposed thiol that served as an internal control to assess labeling efficiency.

Figure 16:
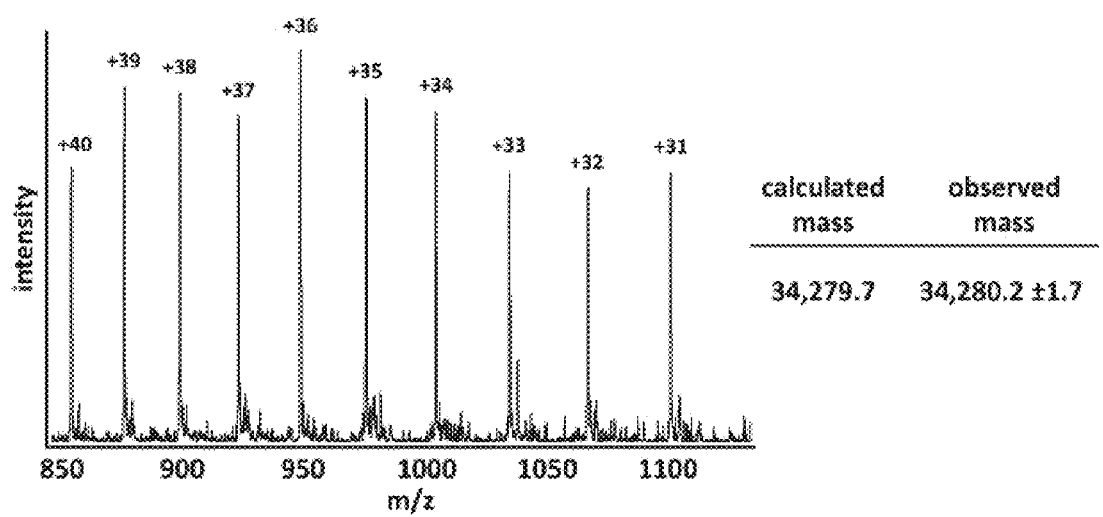

FIG. 16 provides data illustrating that Strep FGE does not exhibit a mass anomaly indicative of a stable, covalent modification of Cys272. The His6-tag was cleaved from Strep FGE and the mass of the enzyme was determined by mass spectrometry. Numbers above each ion peak represent charge states.

Figure 17:
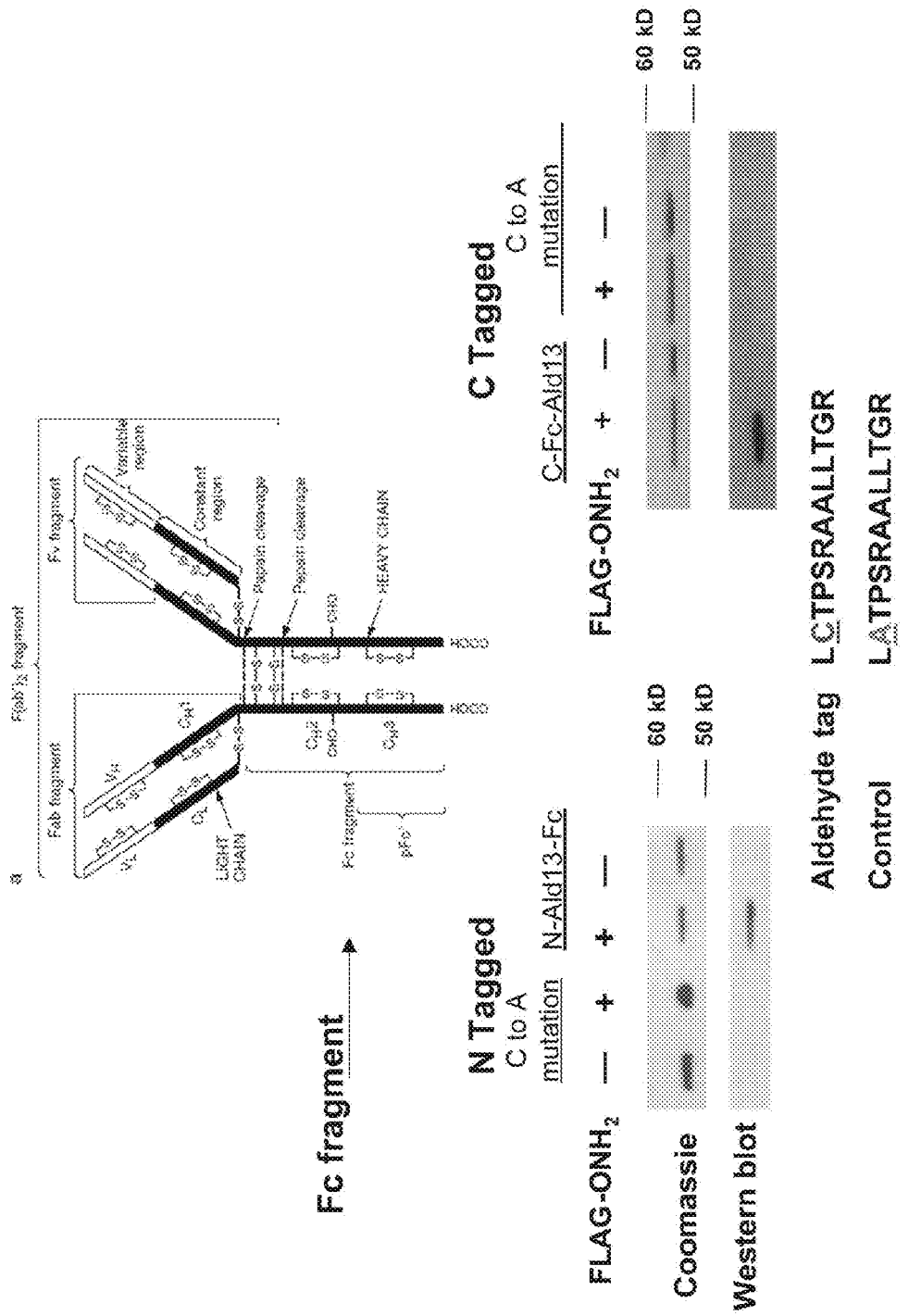

FIG. 17 provides a schematic of site-specific labeling of recombinant IgG Fc, including a schematic of an antibody and results of modification of an Fc fragment that is either N-tagged (N-Ald$_{13}$-Fc) or C-tagged (C-Ald$_{13}$-Fc) with a 13mer aldehyde tag (LCTPSRAALLTGR) (SEQ ID NO: 84) or N- or C-modified with a control tag (LATPSRAALLTGR) (SEQ ID NO: 60).

Figure 18:
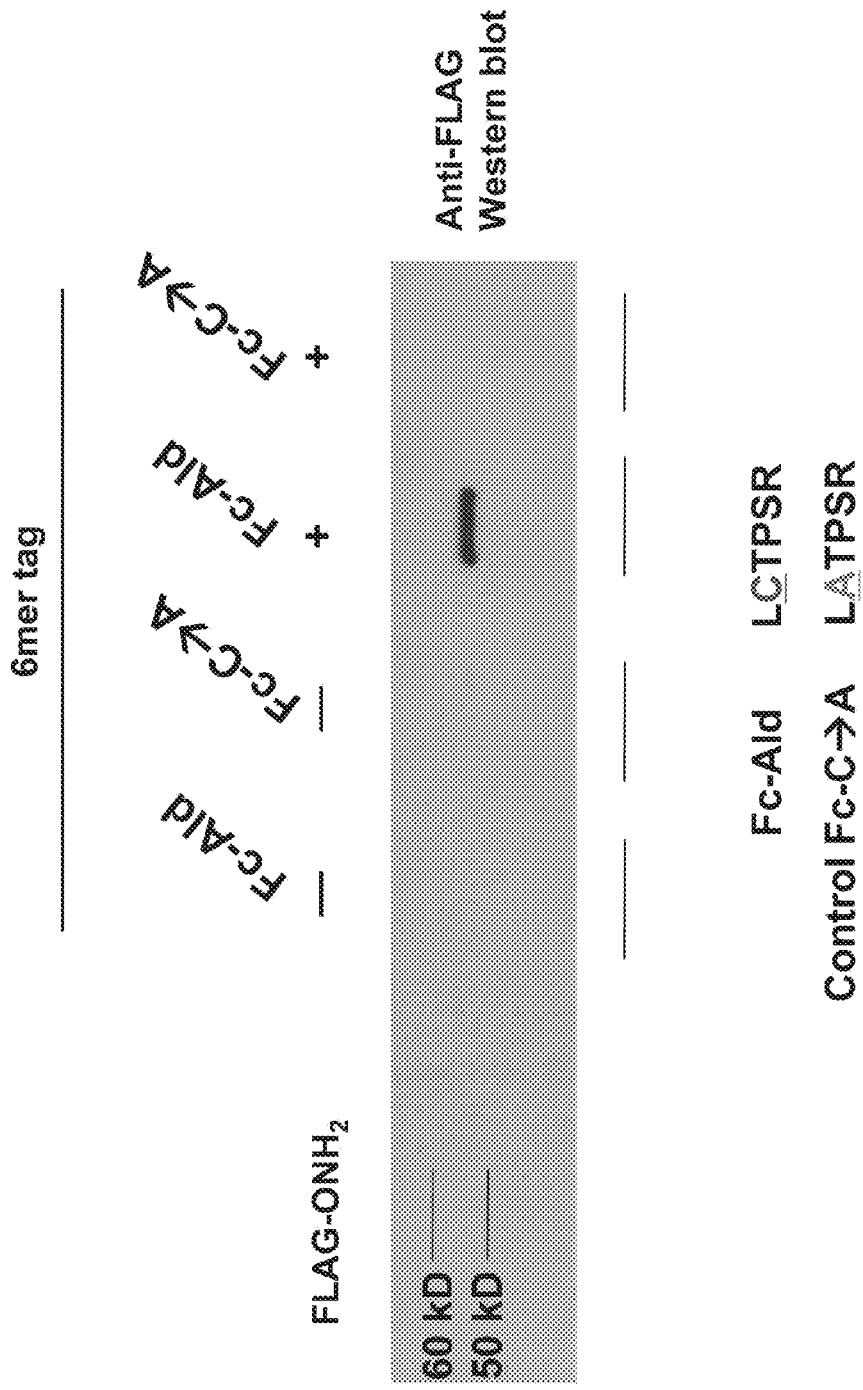

FIG. 18 provides a schematic of site-specific labeling of an IgG Fc fragment using a 6mer aldehyde tag, and includes results of modification of an Fc fragment that is either N-tagged (N-Ald$_6$-Fc) or C-tagged (C-Ald$_6$-Fc) with a 6mer aldehyde tag (LCTPSR) (SEQ ID NO: 1) or N- or C-modified with a control tag (LATPSR) (SEQ ID NO: 95).

Figure 19:
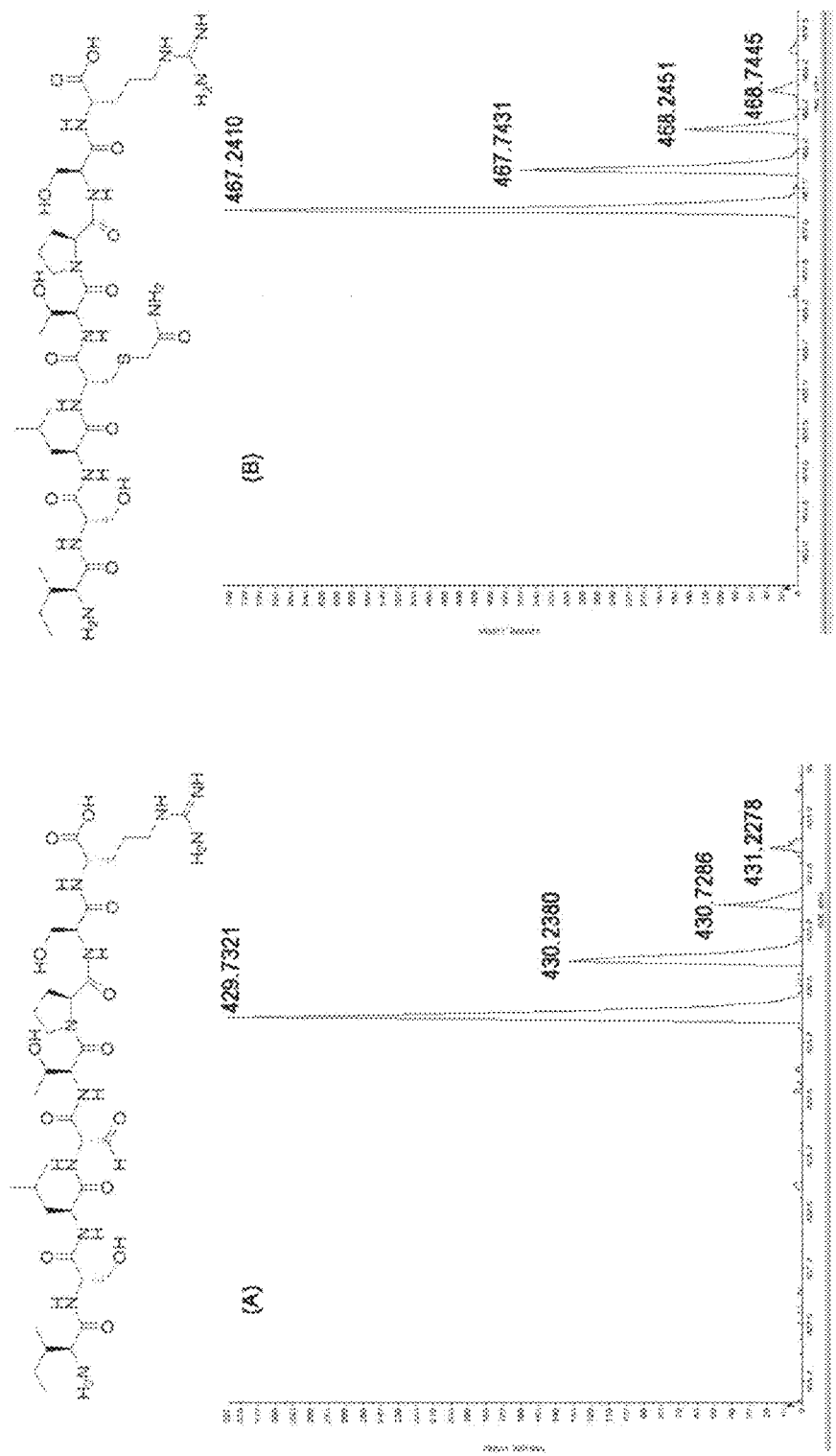

FIG. 19 provides results of identification of formylglycine (FGly)-containing peptides from N-tagged IgG Fc, and includes a set of graphs showing mass spectrum analysis confirming presence of FGly in a tryptic fragments of N-tagged Fc fragment. (Panel a) Mass spectrum of tryptic fragments incorporating FGly. Theoretical: 429.7268 m/z; Observed: 429.7321 m/z. (Panel b) Mass spectrum of tryptic fragment of N-tagged Fc fragment incorporating FGly after treatment with 2-iodoacetamide. Theoretical: 467.2375 m/z Observed: 467.2410 m/z.

Figure 20:
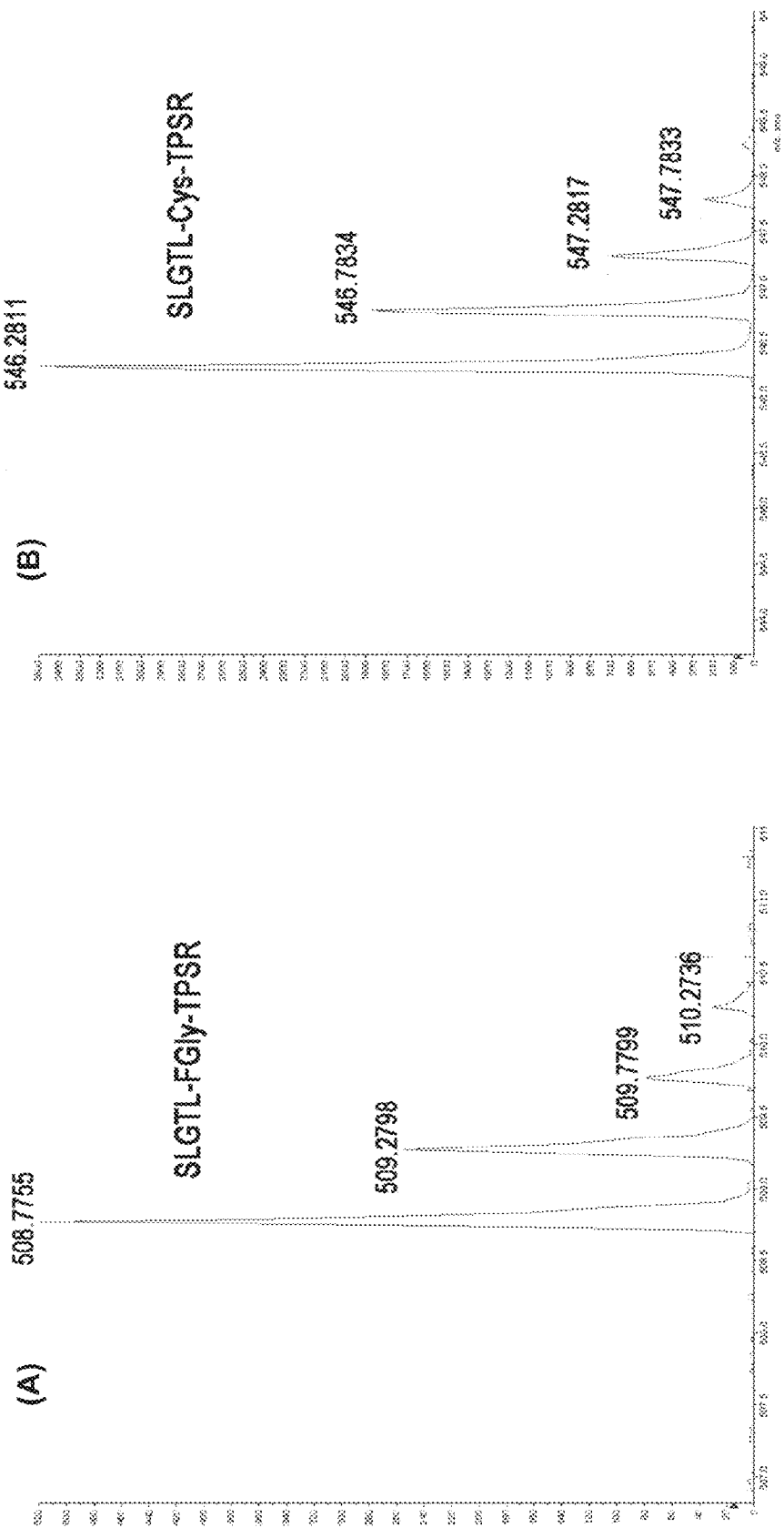

FIG. 20 provides results of identification of formylglycine (FGly)-containing peptides from C-tagged IgG Fc, and a set of graphs showing mass spectrum analysis confirming presence of FGly in a tryptic fragments of C-tagged Fc fragment. (Panel a) Mass spectrum of tryptic fragments incorporating FGly. Theoretical: 508.7613 m/z; Observed: 508.7755m/z. (Panel b) Mass spectrum of tryptic fragment of C-tagged Fc fragment incorporating FGly after treatment with 2-iodoacetamide. Theoretical: 546.2721 m/z; Observed: 546.2811m/z.

Figure 21:
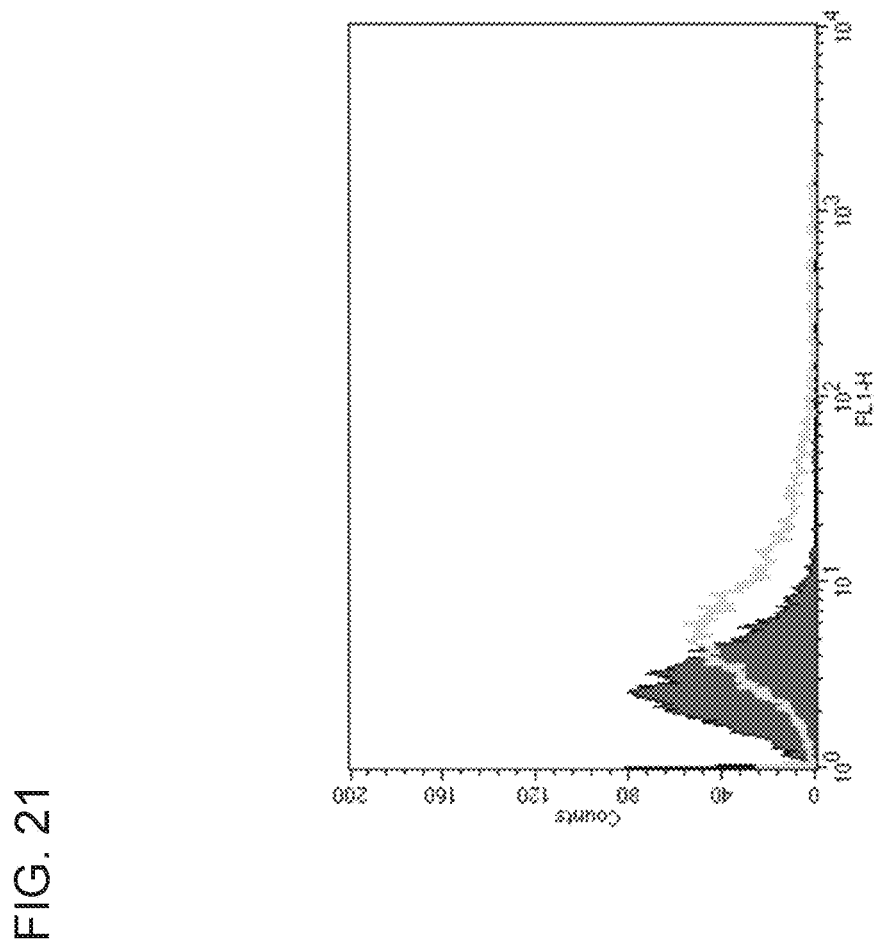
Figure 21:
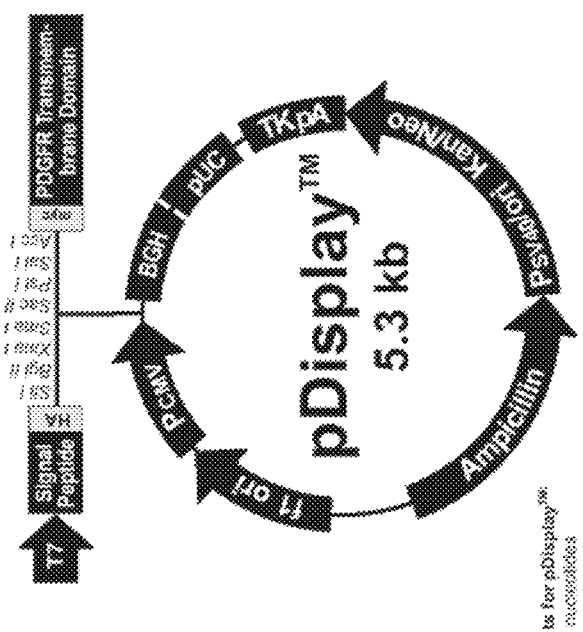

FIG. 21 relates to site-specific labeling of a cell surface protein, and provides a schematic of the pDisplay™ vector used for construction of aldehyde tagged cell surface protein (using a 13mer aldehyde tag of LCTPSRAALTGR) (SEQ ID NO:96) and a graph showing increased mean fluorescence for surface protein tagged with the 13mer (Ald13-TM) as compared to control (LATPSRAALLTGR (SEQ ID NO:60); referred to as C→A-TM).

Figure 22:
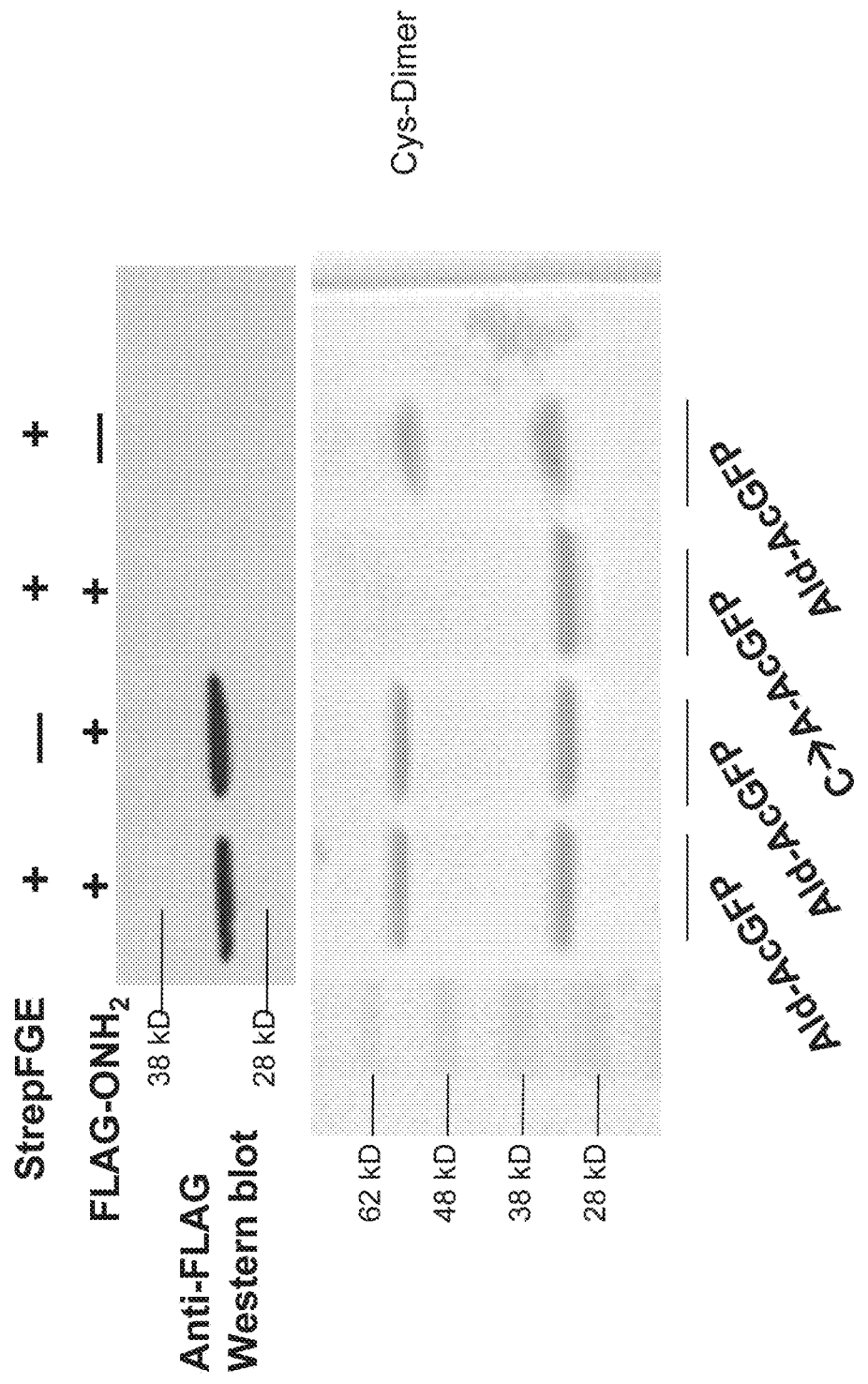

FIG. 22 relates to site-specific labeling a cytosolic protein, exemplified by His$_6$-Ald$_{13}$-AcGFP, and provides the results of modification of green fluorescent protein (GFP) fusion protein containing a His tag and a 13mer aldehyde tag (referred to as His$_6$-Ald$_{13}$-Ac-GFP or Ald-AcGFP) or a GFP fusion protein containing a control tag (LATPSRAALLTGR) (SEQ ID NO:60) (referred to as C→A-AcGFP.

Figure 23:
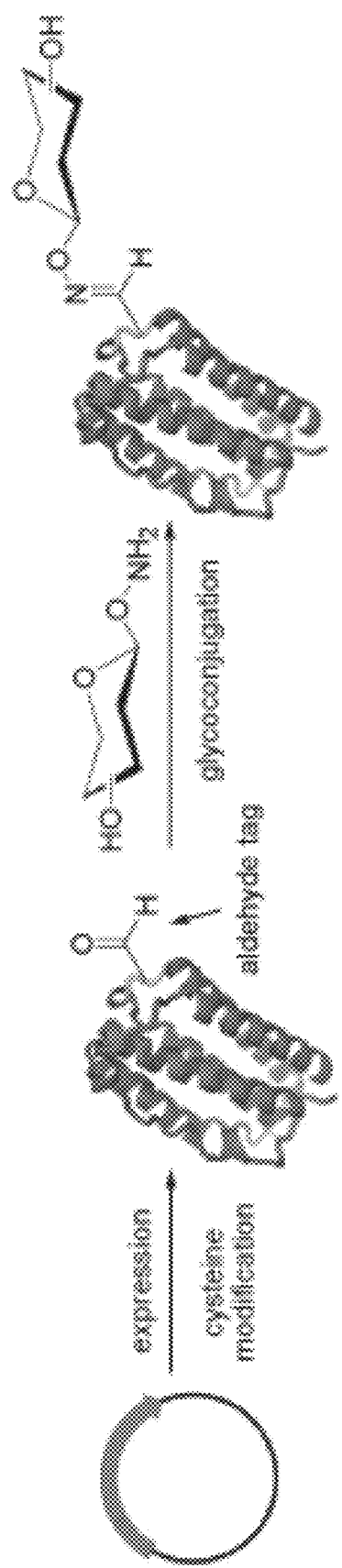

FIG. 23 provides a schematic outlining site-specific glycosylation of interferon beta (IFN-B eta) using the aldehyde tag methodology.

DETAILED DESCRIPTION OF EMBODIMENTS OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "an aldehyde tag" includes a plurality of such tags and reference to "the polypeptide" includes reference to one or more polypeptides and equivalents thereof known to those skilled in the art, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The terms "polypeptide", "peptide" and "protein" are used interchangeably herein to refer to a polymeric form of amino acids of any length. Unless specifically indicated otherwise, "polypeptide", "peptide" and "protein" can include genetically coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, proteins which contain at least one N-terminal methionine residue (e.g., to facilitate production in a recombinant bacterial host cell); immunologically tagged proteins; and the like.

"Target polypeptide" is used herein to refer to a polypeptide that is to be modified by use of an aldehyde tag as described herein.

"Native amino acid sequence" or "parent amino acid sequence" are used interchangeably herein in the context of a target polypeptide to refer to the amino acid sequence of the target polypeptide prior to modification to include a heterologous aldehyde tag.

By "aldehyde tag" or "ald-tag" is meant an amino acid sequence that contains an amino acid sequence derived from a sulfatase motif which is capable of being converted, or which has been converted, by action of a formylglycine generating enzyme (FGE) to contain a 2-formylglycine residue (referred to herein as "FGly"). Although this is technically incorrect, the FGly residue generated by an FGE is often referred to in the literature as a "formylglycine". Stated differently, the term "aldehyde tag" is used herein to refer to an amino acid sequence comprising an "unconverted" sulfatase motif (i.e., a sulfatase motif in which the cysteine or serine residues has not been converted to FGly by an FGE, but is capable of being converted) as well as to an amino acid sequence comprising a "converted" sulfatase motif (i.e., a sulfatase motif in which the cysteine or serine resuides has been converted to FGly by action of an FGE).

By "conversion" as used in the context of action of a formylglycine generating enzyme (FGE) on a sulfatase motif refers to biochemical modification of a cysteine or serine residue in a sulfatase motif to a formylglycine (FGly) residue (e.g., Cys to FGly, or Ser to FGly).

"Modification" encompasses addition, removal, or alteration of a moiety. As used in the context of a polypeptide having a converted sulfatase motif, "modification" is meant to refer to chemical or biochemical modification of an FGly residue of an aldehyde tag of a polypeptide through reaction of the FGly aldehyde moiety with a reactive partner. As discussed above, the term "conversion" refers to a type of biochemical modification of a FGly residue of an aldehyde tag mediated by an FGE.

By "genetically-encodable" as used in reference to an amino acid sequence of polypeptide, peptide or protein means that the amino acid sequence is composed of amino acid residues that are capable of production by transcription and translation of a nucleic acid encoding the amino acid sequence, where transcription and/or translation may occur in a cell or in a cell-free in vitro transcription/translation system.

The term "control sequences" refers to DNA sequences to facilitate expression of an operably linked coding sequence in a particular expression system, e.g. mammalian cell, bacterial cell, cell-free synthesis, etc. The control sequences that are suitable for prokaryote systems, for example, include a promoter, optionally an operator sequence, and a ribosome binding site. Eukaryotic cell systems may utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate the initiation of translation. Generally, "operably linked" means that the DNA sequences being linked are contiguous, and, in the case of a secretory leader, contiguous and in reading frame. Linking is accomplished by ligation or through amplification reactions. Synthetic oligonucleotide adaptors or linkers may be used for linking sequences in accordance with conventional practice.

The term "expression cassette" as used herein refers to a segment of nucleic acid, usually DNA, that can be inserted into a nucleic acid (e.g., by use of restriction sites compatible with ligation into a construct of interest or by homologous recombination into a construct of interest or into a host cell genome). In general, the nucleic acid segment comprises a polynucleotide that encodes a polypeptide of interest (e.g., an aldehyde tag, which can be operably linked to a polynucleotide encoding a target polypeptide of interest), and the cassette and restriction sites are designed to facilitate insertion of the cassette in the proper reading frame for transcription and translation. Expression cassettes can also comprise elements that facilitate expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, usually 75% free, and most usually 90% free from other components with which it is naturally associated.

The term "physiological conditions" is meant to encompass those conditions compatible with living cells, e.g., predominantly aqueous conditions of a temperature, pH, salinity, etc. that are compatible with living cells.

By "heterologous" is meant that a first entity and second entity are provided in an association that is not normally found in nature. For example, a protein containing a "heterologous" sulfatase motif or "heterologous" ald-tag is a protein that does not normally contain a sulfatase motif at that position within its amino acid sequence (e.g., proteins which have a single, native sulfatase motif can contain a second sulfatase motif that is "heterologous"; further proteins which contain a sulfatase motif can be modified so as to reposition the sulfatase motif, rendering the re-positioned sulfatase motif "heterologous" to the protein). In some embodiments, a heterologous sulfatase motif is present in a polypeptide which contains no native sulfatase motif.

By "reactive partner" is meant a molecule or molecular moiety that specifically reacts with another reactive partner to produce a reaction product. Exemplary reactive partners include an cysteine or serine of sulfatase motif and a formylglycine generating enzyme (FGE), which react to form a reaction product of a converted aldehyde tag containing a FGly in lieu of cysteine or serine in the motif. Other exemplary reactive partners include an aldehyde of a formylglycine (FGly) residue of a converted aldehyde tag and a reactive partner reagent comprising a moiety of interest, which react to form a reaction product of a modified aldehyde tagged polypeptide having the moiety of interest conjugated to the aldehyde tagged polypeptide at the FGly residue.

"N-terminus" refers to the terminal amino acid residue of a polypeptide having a free amine group, which amine group in non-N-terminus amino acid residues normally forms part of the covalent backbone of the polypeptide.

"C-terminus" refers to the terminal amino acid residue of a polypeptide having a free carboxyl group, which carboxyl group in non-C-terminus amino acid residues normally forms part of the covalent backbone of the polypeptide.

By "N-terminal" is meant the region of a polypeptide that is closer to the N-terminus than to the C-terminus By "C-terminal" is meant the region of a polypeptide that is closer to the C-terminus than to the N-terminus.

By "internal site" as used in referenced to a polypeptide or an amino acid sequence of a polypeptide means a region of the polypeptide that is not at the N-terminus or at the C-terminus, and includes both N-temrinal and C-terminal regions of the polypeptide.

Introduction

The present invention exploits a naturally-occuring, genetically-encodable sulfatase motif for use as a peptide tag, referred to herein as an "aldehyde tag" or "ald-tag", to direct site-specific modification of a polypeptide. The sulfatase motif of the aldehyde tag, which is based on a motif found in active sites of sulfatases, contains a serine or cysteine residue that is capable of being converted (oxidized) to a formylglycine (FGly) by action of a formylglycine generating enzyme (FGE) either in vivo (e.g., at the time of translation of an aldehyde tag-containing protein in a cell) or in vitro (e.g., by contacting an aldehyde tag-containing protein with an FGE in a cell-free system). The aldehyde moiety of the resulting FGly residue can be used as a "chemical handle" to facilitate site-specific chemical modification of the protein.

Figure 1A:
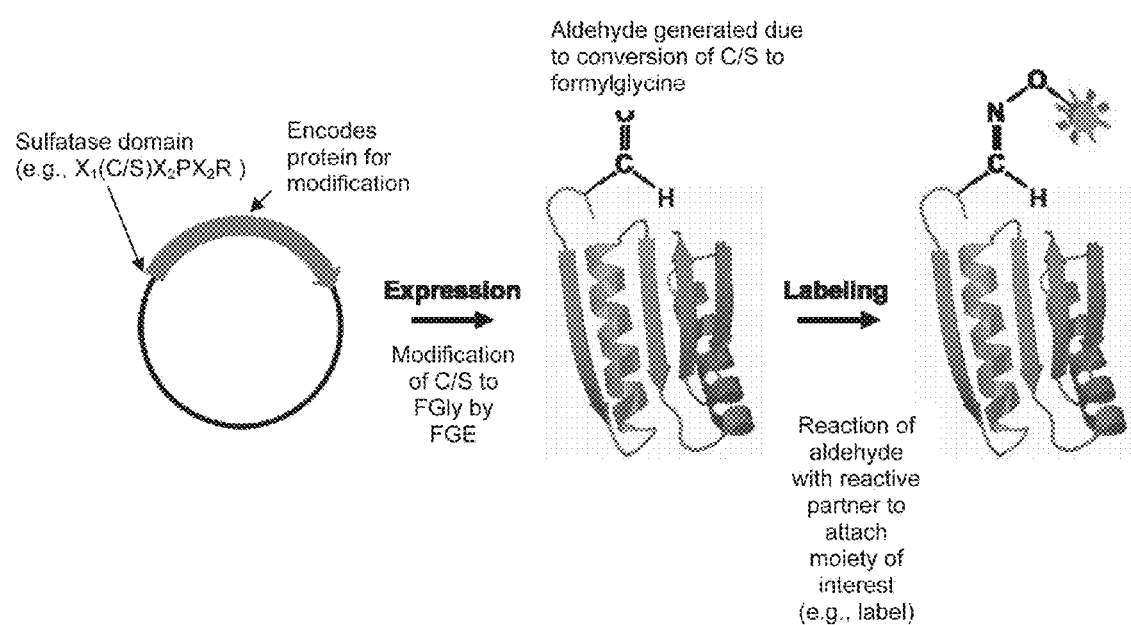
FIG. 1A is a schematic showing an exemplary outline of the methods and compositions of the invention. In this example, an exemplary sulfatase motif ("LCTPSR") (SEQ ID NO:1) is positioned in a construct containing a nucleic acid encoding a protein of interest.

FIG. 1A is a schematic showing an exemplary methods and compositions of the invention. In this example, an exemplary sulfatase motif ("LCTPSR") (SEQ ID NO:1) is positioned in a construct containing a nucleic acid encoding a protein of interest. In this example, the sulfatase motif is positioned at the N-terminus of the encoded protein following expression; however, as described in more detail below, sulfatase motifs can be inserted at one or more desired sites of the polypeptide (e.g., to provide for the motif at the N-terminus, C-terminus and/or internal site of the encoded polypeptide). The sulfatase motif exemplified in FIG. 1A is within a genus of sulfatase motifs as described below in more detail. FIG. 1B is a schematic of a sequence alignment of the sulfatase motif from a variety of sulfatases found in diverse organisms. The consensus sequence contains the sequence of the two aldehyde tags used in this study. Conserved residues are highlighted.

Upon expression in a cell and/or exposure to the appropriate enzyme (e.g., AtsB-type or SUMF1-type FGE), the encoded cysteine of the sulfatase motif is converted to a formylglycine (FGly). The aldehyde of the FGly residue can be used as a "chemical handle" for a variety of applications, e.g., for covalent ligation with a moiety of interest or for applications such as protein immobilization. In FIG. 1A, the exemplary moiety is a detectable label which is attached to the modified cysteine residue of the sulfatase moiety.

Both placement of the aldehyde tag within the target protein to be modified and aldehyde tag-mediated modification as disclosed herein are generalizable with respect to a wide variety of proteins. The ability of FGE to facilitate conversion of the sulfatase motif to generate a FGly residue is independent of the position of the motif within the protein. Because FGE can convert the cysteine/serine of the sulfatase motif in manner that is both sequence context-independent and structural-context independent, aldehyde tags can be positioned at any desired site within a target polypeptide to be modified, with the proviso that the sulfatase motif is accessible to the FGE at the time of enzymatic conversion. Furthermore, the unique reactivity of the aldehyde allows for bioorthongonal and chemoselective modification of recombinant proteins, thus providing a site-specific means for chemical modification of proteins that can be conducted under physiological conditions and in a highly selective manner.

As will be appreciated from the present disclosure, the applications of aldehyde tags are numerous and can provide a number of advantages. For example, the aldehyde tag is smaller than most if not all conventional peptide tags that allow for covalent modification of proteins, thereby requiring minimal changes to the amino acid sequence of a target polypeptide. Second, the aldehyde tag takes advantage of well-characterized secondary labeling chemistries. Third, the aldehyde tag demonstrates reversibility, and through selection of reactive partners that provide for moiety conjugation through covalent bonds of differing stability, allows for sequential modification and replacement of a moiety attached at an aldehyde tag. Further, because the aldehyde tag is formed using biosynthetic machinery already present in most cellular systems, and is independent of the nature of the target or placement within the parent amino acid sequence, the aldehyde tag can be used to facilitate modification of a large number of polypeptides using readily available expression system.

The aldehyde moiety of a converted aldehyde tag can be used for a variety of applications including, but not limited to, visualization using fluorescence or epitope labeling (e.g., electron microscopy using gold particles equipped with aldehyde reactive groups), protein immobilization (e.g., protein microarray production), protein dynamics and localization studies and applications, and conjugation of proteins with a moiety of interest (e.g., moieties that improve a parent protein's therapeutic index (e.g., PEG), targeting moieties (e.g., to enhance bioavailability to a site of action), and biologically active moieties (e.g., a therapeutic moiety).

Of particular interest is the use of aldehyde tags to facilitate site-specific attachment of a water-soluble polymer, such as PEG. Despite advances in protein conjugation chemistries, controlled, site-specific modification of proteins remains a challenge. Many conventional PEGylation methods attach PEG moieties through reaction with, for example, a lysine or cysteine as a target residue. Due to the presence of multiple target residues in a protein, such conventional systems can result in PEGylation at multiple sites, creating a collection of discrete protein-PEG conjugates with different pharmacokinetics. In contrast, use of an FGly residue of an aldehyde tag as a target residue provides a unique site for covalent polymer attachment, and thus increases both specificity and homogeneity of the resulting modified product. These and other features and advantages will be readily apparent to the ordinarily skilled artisan upon reading the present disclosure.

The methods and compositions for practice of the invention will now be described in more detail.

Aldehyde Tags

In general, an aldehyde tag can be based on any amino acid sequence derived from a sulfatase motif (also referred to as a "sulfatase domain") which is capable of being converted by action of a formylglycine generating enzyme (FGE) to contain a formylglycine (FGly). Action of FGE is directed in a sequence-specific manner in that the FGE acts at a sulfatase motif, but this sulfatase motif can be positioned within any region of a target polypeptide. Thus, FGE-mediated conversion of a sulfatase motif is site-specific (i.e., in that FGE acts at the amino acid sequence of a sulfatase motif) but the ability of FGE to act upon the sulfatase motif is sequence context-independent (i.e., the ability of the FGE to convert a cysteine/serine of a sulfatase motif is independent of the sequence context in which the sulfatase motif is presented in the target polypeptide).

Exemplary Aldehyde Tats

A minimal sulfatase motif of an aldehyde tag is usually about 5 or 6 amino acid residues in length, usually no more than 6 amino acid residues in length. In general, it is normally desirable to minimize the extent of modification of the native amino acid sequence of the target polypeptide, so as to minimize the number of amino acid residues that are inserted, deleted, substituted (replaced), or added (e.g., to the N- or C-terminus) Minimizing the extent of amino acid sequence modification of the target polypeptide is usually desirable so as to minimize the impact such modifications may have upon target polypeptide function and/or structure. Thus, aldehyde tags of particular interest include those that require modification (insertion, addition, deletion, substitution/replacement) of less than 16, 15, 14, 13, 12, 11, 10, 9, 8, or 7 amino acid residues of the amino acid sequence of the target polypeptide.

It should be noted that while aldehyde tags of particular interest are those based on a minimal sulfatase motif, it will be readily appreciated that longer aldehyde tags are both contemplated and encompassed by the present disclosure and can find use in the compositions and methods of the invention. Aldehyde tags can thus comprise a minimal sulfatase motif of 5 or 6 residues, or can be longer and comprise a minimsal sulfatase motif which can be flanked at the N- and/or C-terminal sides of the motif by additional amino acid residues. Aldehyde tags of, for example, 5 or 6 amino acid residues are contemplated, as well as longer amino acid sequences of more than 5, 6, 7, 8, 9, 10, 11, 12, 13, 14, 15, 16, 17, 18, 19, 20 or more amino acid residues.

In general, sulfatase motifs useful in aldehyde tags as described herein are of the formula:

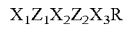  (I)

where $Z_1$ is cysteine or serine (which can also be represented by (C/S));

$Z_2$ is either a proline or alanine residue (which can also be represented by (P/A));

$X_1$ is present or absent and, when present, can be any amino acid, though usually an aliphatic amino acid, a sulfur-containing amino acid, or a polar, uncharged amino acid, (i.e., other than a aromatic amino acid or a charged amino acid), usually L, M, V, S or T, more usually L, M, S or V, with the proviso that when the sulfatase motif is at the N-terminus of the target polypeptide, $X_1$ is present; and $X_2$ and $X_3$ independently can be any amino acid, though usually an aliphatic amino acid, a polar, uncharged amino acid, or a sulfur containing amino acid (i.e., other than a aromatic amino acid or a charged amino acid), usually S, T, A, V, G or C, more usually S, T, A, V or G.

It should be noted that, following action of an FGE on the sulfatase motif, $Z_1$ is oxidized to generate a formylglycine (FGly) residue. Furthermore, following both FGE-mediated conversion and reaction with a reactive partner comprising a moiety of interest, FGly position at $Z_1$ in the formula above is covalently bound to the moiety of interest (e.g., detectable label, water soluble polymer, etc).

Where the aldehyde tag is present at a location other than the N-terminus of the target polypeptide, $X_1$ of the formula above can be provided by an amino acid residue of the native amino acid sequence of the target polypeptide. Therefore, in some embodiments, and when present at a location other than the N-terminus of a target polypeptide, sulfatase motifs are of the formula:

  (II)

where $X_1$ and $X_2$ independently can be any amino acid, though usually an aliphatic amino acid, a polar, uncharged amino acid, or a sulfur-containing amino acid (i.e., other than an aromatic amino acid or a charged amino acid), usually S, T, A, V, or C, more usually S, T, A, or V.

As noted above, the sulfatase motif can contain additional residues at one or both of the N- and C-terminus of the sequence, e.g., such that the aldehyde tag includes both a sulfatase motif and an "auxiliary motif". In one embodiment, the sulfatase motif includes an auxiliary motif at the C-terminus (i.e., following the arginine residue in the formula above) 1, 2, 3, 4, 5, 6, or all 7 of the contiguous residues of an amino acid sequence of AALLTGR (SEQ ID NO:2), SQLLTGR (SEQ ID NO:3), AAFMTGR (SEQ ID NO:4), AAFLTGR (SEQ ID NO:5), SAFLTGR (SEQ ID NO:6), ASILTGK (SEQ ID NO:7), VSFLTGR (SEQ ID NO:8), ASLLTGL (SEQ ID NO:9), ASILITG (SEQ ID NO:10), VSFLTGR (SEQ ID NO:11), SAIMTGR (SEQ ID NO:12), SAIVTGR (SEQ ID NO:13), TNLWRG (SEQ ID NO:14), TNLWRGQ (SEQ ID NO:15), TNLCAAS (SEQ ID NO:16), VSLWTGK (SEQ ID NO:17), SMLLTG (SEQ ID NO:18), SMLLTGN (SEQ ID NO:19), SMLLTGT (SEQ ID NO:20), ASFMAGQ (SEQ ID NO:21), or ASLLTGL (SEQ ID NO:22), (see, e.g., Dierks et al. (1999) EMBO J 18(8): 2084-2091), or of GSLFTGR (SEQ ID NO:23). However, as set out in the Examples below, the present inventors have found that such additional C-terminal amino acid residues are not required for FGE-mediated conversion of the sulfatase motif of the aldehyde tag, and thus are only optional and may be specifically excluded from the aldehyde tags described herein. In some embodiments the aldehyde tag does not contain an amino acid sequence CGPSR(M/A)S (SEQ ID NO:24) or CGPSR(M/A) (SEQ ID NO:25), which may be present as a native amino acid sequence in phosphonate monoester hydrolases.

The sulfatase motif of the aldehyde tag is generally selected so as to be capable of conversion by a selected FGE, e.g., an FGE present in a host cell in which the aldehyde tagged polypeptide is expressed or an FGE which is to be contacted with the aldehyde tagged polypeptide in a cell-free in vitro method.

Selection of aldehyde tags and an FGE that provide for suitable reactive partners to provide for generation of an FGly in the aldehyde tagged target polypeptide can be readily accomplished in light of information available in the art. In general, sulfatase motifs susceptible to conversion by a eukaryotic FGE contain a cysteine and a proline (i.e., a cysteine and proline at $Z_1$ and $Z_2$, respectively, in Formula I above (e.g., $X_1CX_2PX_3R$); $CX_1PX_2R$ in Formula II above) and are modified by the "SUMF1-type" FGE (Cosma et al. Cell 2003, 113, (4), 445-56; Dierks et al. Cell 2003, 113, (4), 435-44). Sulfatase motifs susceptible to conversion by a prokaryotic FGE contain either a cysteine or a serine, and a proline in the sulfatase motif (i.e., a cysteine or serine at $Z_1$, and a proline at $Z_2$, respectively, in Formula I above (e.g., $X_1(C/S)X_2PX_3R$); $(C/S)X_1PX_2R$ in Formula II above) are modified either by the "SUMF1-type" FGE or the "AtsB-type" FGE, respectively (Szameit et al. J Biol Chem 1999, 274, (22), 15375-81). Other sulfatase motifs susceptible to conversion by a prokaryotic FGE contain either a cysteine or a serine, and either a proline or an alanine in the sulfatase motif (i.e., a cysteine or serine at $Z_1$, and a proline or alanine at $Z_2$, respectively, in Formula I above (e.g., $X_1CX_2PX_3R$; $X_1SX_2PX_3R$; $X_1CX_2AX_3R$; $X_1SX_2AX_3R$); $CX_1PX_2R$; $SX_1PX_2R$; $CX_1AX_2R$; $SX_1AX_2R$ in Formula II above), and are susceptible to modification by, for example, can be modified by an FGE of a Firmicutes (e.g., *Clostridium perfringens*) (see Berteau et al. *J. Biol. Chem.* 2006; 281:22464-22470).

Therefore, for example, where the FGE is a eukaryotic FGE (e.g., a mammalian FGE, including a human FGE), the sulfatase motif is usually of the formula:

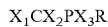

$$X_1CX_2PX_3R$$

where $X_1$ may be present or absent and, when present, can be any amino acid, though usually an aliphatic amino acid, a sulfur-containing amino acid, or a polar, uncharged amino acid, (i.e., other than a aromatic amino acid or a charged amino acid), usually L, M, S or V, with the proviso that when the sulfatase motif is at the N-terminus of the target polypeptide, $X_1$ is present; and $X_2$ and $X_3$ independently can be any amino acid, though usually an aliphatic amino acid, a sulfur-containing amino acid, or a polar, uncharged amino acid, (i.e., other than a aromatic amino acid or a charged amino acid), usually S, T, A, V, G, or C, more usually S, T, A, V or G.

Specific examples of sulfatase motifs include LCTPSR (SEQ ID NO:1), MCTPSR (SEQ ID NO:26), VCTPSR (SEQ ID NO:27), LCSPSR (SEQ ID NO:28), LCAPSR (SEQ ID NO:29), LCVPSR (SEQ ID NO:30), and LCGPSR (SEQ ID NO:31). Other specific sulfatase motifs are readily apparent from the disclosure provided herein.

As described in more detail below, a converted aldehyde tagged polypeptide is reacted with a reactive partner containing a moiety of interest to provide for conjugation of the moiety of interest to the FGly residue of the converted aldehyde tagged polypeptide, and production of a modified polypeptide. Modified polypeptides having a modified aldehyde tag are generally described by comprising a modified sulfatase motif of the formula:

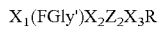

$$X_1(FGly')X_2Z_2X_3R \quad (I)$$

where

FGly' is the formylglycine residue having a covalently attached moiety;

$Z_2$ is either a proline or alanine residue (which can also be represented by (P/A));

$X_1$ may be present or absent and, when present, can be any amino acid, though usually an aliphatic amino acid, a sulfur-containing amino acid, or a polar, uncharged amino acid, (i.e., other than a aromatic amino acid or a charged amino acid), usually L, M, V, S or T, more usually L, M or V, with the proviso that when the sulfatase motif is at the N-terminus of the target polypeptide, $X_1$ is present; and $X_2$ and $X_3$ independently can be any amino acid, though usually an aliphatic amino acid, a sulfur-containing amino acid, or a polar, uncharged amino acid, (i.e., other than a aromatic amino acid or a charged amino acid), usually S, T, A, V, G or C, more usually S, T, A, V or G.

Specific examples of converted sulfatase motifs include L(FGly)TPSR (SEQ ID NO:32), M(FGly)TPSR (SEQ ID NO:33), V(FGly)TPSR (SEQ ID NO:34), L(FGly)SPSR (SEQ ID NO:35), L(FGly)APSR (SEQ ID NO:36), L(FGly)VPSR (SEQ ID NO:37), and L(FGly)GPSR (SEQ ID NO:38).

As described in more detail below, the moiety of interest can be any of a variety of moieties such as a water-soluble polymer, a detectable label, a drug, or a moiety for immobilization of the polypeptide in a membrane or on a surface. As is evident from the above discussion of aldehyde tagged polypeptides, the modified sulfatase motif of the modified polypeptide can be positioned at any desired site of the polypeptide. Thus, the present disclosure provides, for example, a modified polypeptide having a modified sulfatase motif positioned at a site of post-translational modification of a parent of the modified polypeptide (i.e., if the target polypeptide is modified to provide an aldehyde tag at a site of post-translational modification, the later-produced modified polypeptide will contain a moiety at a position corresponding to this site of post-translational modification in the parent polypeptide). For example, then, a modified polypeptide can be produced so as to have a covalently bound, water-soluble polymer at a site corresponding to a site at which glycosylation would normally occur in the parent target polypeptide. Thus, for example, a PEGylated polypeptide can be produced having the PEG moiety positioned at the same or nearly the same location as sugar residues would be positioned in the naturally-occurring parent polypeptide. Similarly, where the parent target polypeptide is engineered to include one or more non-native sites of post-translational modification, the modified polypeptie can contain covalently attached water-soluble polymers at one or more sites of the modified polypeptide corresponding to these non-native sites of post-translational modification in the parent polypeptide.

Modification of a Target Polypeptide to Include an Aldehyde Tag

Aldehyde tags can be positioned at any location within a target polypeptide at which it is desired to provide for conversion and/or modification of the target polypeptide, with the proviso that the site of the aldehyde tag is accessible for conversion by an FGE and subsequent modification at the FGly, or can be rendered accessible (e.g., by denaturing the protein). Target polypeptides can be modified to include one or more aldehyde tags The number of aldehyde tags that can be present in a target polypeptide will vary with the target polypeptide selected, and may include 1, 2, 3, 4, 5, or more aldehyde tags.

In some embodiments it is desirable to position the aldehyde tag(s) in the target polypeptide taking into account its structure when folded (e.g., in a cell-free environment, usually a cell-free physiological environment) and/or presented in or on a cell membrane (e.g., for cell-membrane associated polypeptides, such as transmembrane proteins). For example, an aldehyde tag can be positioned at a solvent accessible site in the folded target polypeptide. The solvent accessible aldehyde tag in a folded unconverted aldehyde tagged polypeptide is thus accessible to an FGE for conversion of the serine or cysteine to an FGly. Likewise, a solvent accessible aldehyde tag of a converted aldehyde tagged polypeptide is accessible to a reactive partner reagent for conjugation to a moiety of interest to provide a modified aldehyde tagged polypeptide. Where an aldehyde tag is positioned at a solvent accessible site, in vitro FGE-mediated conversion and modification with a moiety by reaction with a reactive partner can be performed without the need to denature the protein. Solvent accessible sites can also include target polypeptide regions that are exposed at an extracellular or intracellular cell surface when expressed in a host cell (e.g., other than a transmembrane region of the target polypeptide).

Accordingly, or more aldehyde tags can be provided at sites independently selected from, for example, a solvent accessible N-terminus, a solvent accessible N-terminal region, a solvent accessible C-terminus, a solvent accessible C-terminal region, and/or a loop structure (e.g., an extracellular loop structure and/or an intracellular loop structure). In some embodiments, the aldehyde tag is positioned at a site other than the C-terminus of the polypeptide. In other embodiments, the polypeptide in which the aldehyde tag is positioned is a full-length polypeptide.

In other embodiments, an aldehyde tag site is positioned at a site which is post-translationally modified in the native target polypeptide. For example, an aldehyde tag can be introduced at a site of glycosylation (e.g., N-glycosylation, O-glycosylation), phosphorylation, sulftation, ubiquitination, acylation, methylation, prenylation, hydroxylation, carboxylation, and the like in the native target polypeptide. Consensus sequences of a variety of post-translationally modified sites, and methods for identification of a post-translationally modified site in a polypeptide, are well known in the art. It is understood that the site of post-translational modification can be naturally-occurring or such a site of a polypeptide that has been engineered (e.g., through recombinant techniques) to include a post-translational modification site that is non-native to the polypeptide (e.g., as in a glycosylation site of a hyperglycosylated variant of EPO). In the latter embodiment, polypeptides that have a non-native post-translational modification site and which have been demonstrated to exhibit a biological activity of interest are of particular interest.

The disclosure also provides herein methods for identifying suitable sites for modification of a target polypeptide to include an aldehyde tag. For example, one or more aldehyde tagged-target polypeptides constructs can be produced, and the constructs expressed in a cell expressing an FGE, or exposed to FGE following isolation from the cell (as described in more detail below). The aldehyde tagged-polypeptide can then be contacted with a reactive partner that, if the aldehyde tag is accessible, provides for attachment of a detectable moiety to the FGly of the aldehyde tag. The presence or absence of the detectable moiety is then determined. If the detectable moiety is detected, then positioning of the aldehyde tag in the polypeptide was successful. In this manner, a library of constructs having an aldehyde tag positioned at different sites in the coding sequence of the target polypeptide can be produced and screened to facilitate identification of an optimal position of an aldehyde tag. In addition or alternatively, the aldehyde tagged-polypeptide can be tested for a biological activity normally associated with the target polypeptide, and/or the structure of the aldehyde tagged-polypeptide assessed (e.g., to assess whether an epitope normally present on an extracellular cell surface in the native target polypeptide is also present in the aldehyde tagged-polypeptide).

An aldehyde tag can be provided in a target polypeptide by insertion (e.g., so as to provide a 5 or 6 amino acid residue insertion within the native amino acid sequence) or by addition (e.g., at an N- or C-terminus of the target polypeptide). An aldehyde tag can also be provided by complete or partial substitution of native amino acid residues with the contiguous amino acid sequence of an aldehyde tag. For example, a heterologous aldehyde tag of 5 (or 6) amino acid residues can be provided in a target polypeptide by replacing 1, 2, 3, 4, or 5 (or 1, 2, 3, 4, 5, or 6) amino acid residues of the native amino acid sequence with the corresponding amino acid residues of the aldehyde tag. Although it generally may be of less interest in many applications, target polypeptides having more than one aldehyde tag can be modified so as to provide for attachment of the same moiety or of different moieties at the FGly of the tag.

Modification of a target polypeptide to include one or more aldehyde tags can be accomplished using recombinant molecular genetic techniques, so as produce nucleic acid encoding the desired aldehyde tagged target polypeptide. Such methods are well known in the art, and include cloning methods, site-specific mutation methods, and the like (see, e.g., Sambrook et al., In "Molecular Cloning: A Laboratory Manual" (Cold Spring Harbor Laboratory Press 1989); "Current Protocols in Molecular Biology" (eds., Ausubel et al.; Greene Publishing Associates, Inc., and John Wiley & Sons, Inc. 1990 and supplements). Alternatively, an aldehyde tag can be added using non-recombinant techniques, e.g., using native chemical ligation or pseudo-native chemical ligation, e.g., to add an aldehyde tag to a C-terminus of the target polypeptide (see, e.g., U.S. Pat. No. 6,184,344; U.S. Pat. No. 6,307,018; U.S. Pat. No. 6,451,543; U.S. Pat. No. 6,570,040; US 2006/0173159; US 2006/0149039). See also Rush et al. (Jan. 5, 2006) Org Lett. 8(1):131-4.

Target Polypeptides

Any of a wide variety of polypeptides can be modified to include an aldehyde tag to facilitate modification of the polypeptide. Polypeptides suitable for aldehyde tag-based modification include both proteins having a naturally-occurring amino acid sequence, a native amino acid sequence having an N-terminal methionine, fragments of naturally-occurring polypeptides, and non-naturally occurring polypeptides and fragments thereof. In some embodiments, the target polypeptide is polypeptide other than a sulfatase or fragment thereof, other than a reporter protein, or other than preprolactin or prolactin.

The following are exemplary classes and types of polypeptides which are of interest for modification using the aldehyde tag-based methods described herein.

Therapeutic Polypeptides

In one embodiment, the aldehyde tag-based methods of protein modification are applied to modification of polypeptides that may provide for a therapeutic benefit, particularly those polypeptides for which attachment to a moiety can provide for one or more of, for example, an increase in serum half-life, a decrease in an adverse immune response, additional or alternate biological activity or functionality, and the like. or other benefit or reduction of an adverse side effect. Where the therapeutic polypeptide is an antigen for a vaccine, modification can provide for an enhanced immunogenicity of the polypeptide.

Examples of classes of therapeutic proteins include those that are cytokines, chemokines, growth factors, hormones, antibodies, and antigens. Further examples include erythropoietin (EPO, e.g., native EPO, synthetic EPO (see, e.g., US 2003/0191291), human growth hormone (hGH), bovine growth hormone (bGH), follicle stimulating hormone (FSH), interferon (e.g., IFN-gamma, IFN-beta, IFN-alpha, IFN-omega, consensus interferon, and the like), insulin, insulin-like growth factor (e.g., IGF-I, IGF-II), blood factors (e.g., Factor VIII, Factor IX, Factor X, tissue plasminogen activator (TPA), and the like), colony stimulating factors (e.g., granulocyte-CSF (G-CSF), macrophage-CSF (M-CSF), granulocyte-macrophage-CSF (GM-CSF), and the like), transforming growth factors (e.g., TGF-beta, TGF-alpha), interleukins (e.g., IL-1, IL-2, IL-3, IL-4, IL-5, IL-6, IL-7, IL-8, IL-12, and the like), epidermal growth factor (EGF), platelet-derived growth factor (PDGF), fibroblast growth factors (FGFs, e.g., aFGF, bFGF), glial cell line-derived growth factor (GDNF), nerve growth factor (NGF), RANTES, and the like.

Further examples include antibodies, e.g., polyclonal antibodies, monoclonal antibodies, humanized antibodies, antigen-binding fragments (e.g., F(ab)', Fab, Fv), single chain antibodies, and the like. Of particular interest are antibodies that specifically bind to a tumor antigen, an immune cell antigen (e.g., CD4, CD8, and the like), an antigen of a microorganism, particularly a pathogenic microorganism (e.g., a bacterial, viral, fungal, or parasitic antigen), and the like.

The methods and compositions described herein can be applied to provide for a moiety (e.g., a water-soluble polymer) at a native or engineered site of glycosylation, such as found in hyperglycosylated forms of a protein therapeutic, such as, for example: an interferon (e.g., IFN-γ, IFN-α, IFN-β, IFN-ω; IFN-τ); an insulin (e.g., Novolin, Humulin, Humalog, Lantus, Ultralente, etc.); an erythropoietin (e.g., PROCRIT®, EPREX®, or EPOGEN® (epoetin-α); ARANESP® (darbepoietin-α); NEORECORMON®, EPOGIN® (epoetin-β); and the like); an antibody (e.g., a monoclonal antibody) (e.g., RITUXAN® (rituximab); REMICADE® (infliximab); HERCEPTIN® (trastuzumab); HUMIRA™ (adalimumab); XOLAIR® (omalizumab); BEXXAR® (tositumomab); RAPTIVA™ (efalizumab); ERBITUX™ (cetuximab); and the like), including an antigen-binding fragment of a monoclonal antibody; a blood factor (e.g., ACTIVASE® (alteplase) tissue plasminogen activator; NOVOSEVEN® (recombinant human factor VIIa); Factor VIIa; Factor VIII (e.g., KOGENATE®); Factor IX; β-globin; hemoglobin; and the like); a colony stimulating factor (e.g., NEUPOGEN® (filgrastim; G-CSF); Neulasta (pegfilgrastim); granulocyte colony stimulating factor (G-CSF), granulocyte-monocyte colony stimulating factor, macrophage colony stimulating factor, megakaryocyte colony stimulating factor; and the like); a growth hormone (e.g., a somatotropin, e.g., GENOTROPIN®, NUTROPIN®, NORDITROPIN®, SAIZEN®, SEROSTIM®, HUMATROPE®, etc.; a human growth hormone; and the like); an interleukin (e.g., IL-1; IL-2, including, e.g., Proleukin®; IL-3, IL-4, IL-5, IL-6, IL-7, IL-8, IL-9; etc.); a growth factor (e.g., REGRANEX® (beclapermin; PDGF); FIBLAST® (trafermin; bFGF); STEMGEN® (ancestim; stem cell factor); keratinocyte growth factor; an acidic fibroblast growth factor, a stem cell factor, a basic fibroblast growth factor, a hepatocyte growth factor; and the like); a soluble receptor (e.g., a TNF-α-binding soluble receptor such as ENBREL® (etanercept); a soluble VEGF receptor; a soluble interleukin receptor; a soluble γ/δ T cell receptor; and the like); an enzyme (e.g., α-glucosidase; CERAZYME® (imiglucarase; β-glucocerebrosidase, CEREDASE® (alglucerase;); an enzyme activator (e.g., tissue plasminogen activator); a chemokine (e.g., IP-10; Mig; Groa/IL-8, RANTES; MIP-1α; MIP-1β; MCP-1; PF-4; and the like); an angiogenic agent (e.g., vascular endothelial growth factor (VEGF); an anti-angiogenic agent (e.g., a soluble VEGF receptor); a protein vaccine; a neuroactive peptide such as bradykinin, cholecystokinin, gastin, secretin, oxytocin, gonadotropin-releasing hormone, beta-endorphin, enkephalin, substance P, somatostatin, galanin, growth hormone-releasing hormone, bombesin, warfarin, dynorphin, neurotensin, motilin, thyrotropin, neuropeptide Y, luteinizing hormone, calcitonin, insulin, glucagon, vasopressin, angiotensin II, thyrotropin-releasing hormone, vasoactive intestinal peptide, a sleep peptide, etc.; other proteins such as a thrombolytic agent, an atrial natriuretic peptide, bone morphogenic protein, thrombopoietin, relaxin, glial fibrillary acidic protein, follicle stimulating hormone, a human alpha-1 antitrypsin, a leukemia inhibitory factor, a transforming growth factor, a tissue factor, an insulin-like growth factor, a luteinizing hormone, a follicle stimulating hormone, a macrophage activating factor, tumor necrosis factor, a neutrophil chemotactic factor, a nerve growth factor, a tissue inhibitor of metalloproteinases; a vasoactive intestinal peptide, angiogenin, angiotropin, fibrin; hirudin; a leukemia inhibitory factor; an IL-1 receptor antagonist (e.g., Kineret® (anakinra)); and the like. It will be readily appreciated that native forms of the above therapeutic proteins are also of interest as target polypeptides in the present invention.

The biological activity of a modified target polypeptide can be assayed according to methods known in the art. Modified aldehyde tagged-polypeptides that retain at least one desired pharmacologic activity of the corresponding parent protein are of interest. Examples of useful assays for particular therapeutic proteins include, but are not limited to, GMCSF (Eaves, A. C. and Eaves C. J., Erythropoiesis in culture. In: McCullock E A (edt) Cell culture techniques—Clinics in hematology. W B Saunders, Eastbourne, pp 371-91 (1984); Metcalf, D., International Journal of Cell Cloning 10: 116-25 (1992); Testa, N. G., et al., Assays for hematopoietic growth factors. In: Balkwill F R (edt) Cytokines A practical Approach, pp 229-44; IRL Press Oxford 1991) EPO (bioassay: Kitamura et al., J. Cell. Physiol. 140 p 323 (1989)); Hirudin (platelet aggregation assay: Blood Coagul Fibrinolysis 7(2):259-61 (1996)); IFNα (anti-viral assay: Rubinstein et al., J. Virol. 37(2):755-8 (1981); anti-proliferative assay: Gao Y, et al Mol Cell Biol. 19(11):7305-13 (1999); and bioassay: Czarniecki et al., J. Virol. 49 p 490 (1984)); GCSF (bioassay: Shirafuji et al., Exp. Hematol. 17 p 116 (1989); proliferation of murine NFS-60 cells (Weinstein et al, Proc Natl Acad Sci 83:5010-4 (1986)); insulin ($^3$H-glucose uptake assay: Steppan et al., Nature 409(6818):307-12 (2001)); hGH (Ba/F3-hGHR proliferation assay: J Clin Endocrinol Metab 85(11): 4274-9 (2000); International standard for growth hormone: Horm Res, 51 Suppl 1:7-12 (1999)); factor X (factor X activity assay: Van Wijk et al. Thromb Res 22:681-686 (1981)); factor VII (coagulation assay using prothrombin clotting time: Belaaouaj et al., J. Biol. Chem. 275:27123-8(2000); Diaz-Collier et al., Thromb Haemost 71:339-46 (1994)).

Immunogenic Compositions

The aldehyde tag-based technology disclosed herein also finds application in production of components of immunogenic compositions (e.g., therapeutic vaccines). For example, an aldehyde tag can be used to facilitate attachment of moieties that increase serum half-life of a polypeptide antigen, that increase immunogenicity of the polypeptide, or that link a non-amino acid antigen to a polypeptide carrier. In this regard, aldehyde tags can be used to facilitate modification of microbial antigens (e.g., a bacterial, viral, fungal, or parasitic antigen), tumor antigens, and other antigens which are of interest for administration to a subject to elicit an immune response in the subject. Also of interest is modification of antigens that are useful in eliciting antibodies which can be useful as research tools.

Further exemplary polypeptides of interest for modification using aldehyde tag(s) include those that are of interest for detection or functional monitoring in an assay (e.g., as a research tool, in a drug screening assay, and the like). Exemplary polypeptides of this type include receptors (e.g., G-protein coupled receptors (GPCRs, including orphan GPCRs)), receptor ligands (including naturally-occurring and synthetic), protein channels (e.g., ion channels (e.g., potassium channels, calcium channels, sodium channels, and the like), and other polypeptides. In one embodiment, modification of cell surface-associated polypeptides, such as transmembrane polypeptides) is of particular interest, particularly where such modification is accomplished while the polypeptide is present in a membrane. Methods for modification of an aldehyde tagged-polypeptide under physiological conditions is described further below.

Formylglycine Generating Enzymes (FGEs)

The enzyme that oxidizes cysteine or serine in a sulfatase motif to FGly is referred to herein as a formylglycine generating enzyme (FGE). As discussed above, "FGE" is used herein to refer to FGly-generating enzymes that mediate conversion of a cysteine (C) of a sulfatase motif to FGly as well as FGly-generating enzymes that mediate conversion of serine (S) of a sulfatase motif to FGly. It should be noted that in general, the literature refers to FGly-generating enzymes that convert a C to FGly in a sulfatase motif as FGEs, and refers to enzymes that convert S to FGly in a sulfatase motif as Ats-B-like. However, for purposes of the present disclosure "FGE" is used generically to refer to both types of FGly-generating enzymes, with the understanding that an appropriate FGE will be selected according to the target reactive partner containing the appropriate sulfatase motif (i.e., C-containing or S-containing).

As evidenced by the ubiquitous presence of sulfatases having an FGly at the active site, FGEs are found in a wide variety of cell types, including both eukaryotes and prokaryotes. There are at least two forms of FGEs. Eukaryotic sulfatases contain a cysteine in their sulfatase motif and are modified by the "SUMF1-type" FGE (Cosma et al. Cell 2003, 113, (4), 445-56; Dierks et al. Cell 2003, 113, (4), 435-44). the FGly-generating enzyme (FGE) is encoded by the SUMF1 gene Prokaryotic sulfatases can contain either a cysteine or a serine in their sulfatase motif and are modified either by the "SUMF1-type" FGE or the "AtsB-type" FGE, respectively (Szameit et al. J Biol Chem 1999, 274, (22), 15375-81). In eukaryotes, it is believed that this modification happens co-translationally or shortly after translation in the endoplasmic reticulum (ER) (Dierks et al. Proc Natl Acad Sci USA 1997, 94(22):11963-8). Without being held to theory, in prokaryotes it is thought that SUMF1-type FGE functions in the cytosol and AtsB-type FGE functions near or at the cell membrane. A SUMF2 FGE has also been described in deuterostomia, including vertebrates and echinodermata (see, e.g., Pepe et al. (2003) *Cell* 113, 445-456, Dierks et al. (2003) *Cell* 113, 435-444; Cosma et al. (2004) *Hum. Mutat.* 23, 576-581).

In general, the FGE used to facilitate conversion of cysteine or serine to FGly in a sulfatase motif of an aldehyde tag of a target polypeptide is selected according to the sulfatase motif present in the aldehyde tag. The FGE can be native to the host cell in which the aldehyde tagged polypeptide is expressed, or the host cell can be genetically modified to express an appropriate FGE. In some embodiments it may be desired to use a sulfatase motif compatible with a human FGE (e.g., the SUMF1-type FGE, see, e.g., Cosma et al. Cell 113, 445-56 (2003); Dierks et al. Cell 113, 435-44 (2003)), and express the aldehyde tagged protein in a human cell that expresses the FGE or in a host cell, usually a mammalian cell, genetically modified to express a human FGE.

In general, an FGE for use in the methods disclosed herein can be obtained from naturally occurring sources or synthetically produced. For example, an appropriate FGE can be derived from biological sources which naturally produce an FGE or which are genetically modified to express a recombinant gene encoding an FGE. Nucleic acids encoding a number of FGEs are known in the art and readily available (see, e.g., Preusser et al. 2005 J. Biol. Chem. 280(15):14900-10 (Epub 2005 Jan. 18); Fang et al. 2004 J Biol Chem. 79(15):14570-8 (Epub 2004 Jan. 28); Landgrebe et al. Gene. 2003 Oct. 16; 316:47-56; Dierks et al. 1998 FEBS Lett. 423(1):61-5; Dierks et al. Cell. 2003 May 16; 113(4):435-44; Cosma et al. (2003 May 16) Cell 113(4):445-56; Baenziger (2003 May 16) Cell 113(4):421-2 (review); Dierks et al. Cell. 2005 May 20; 121(4):541-52; Roeser et al. (2006 Jan. 3) Proc Natl Acad Sci USA 103(1):81-6; Sardiello et al. (2005 Nov. 1) Hum Mol Genet. 14(21):3203-17; WO 2004/072275; and GenBank Accession No. NM_182760. Accordingly, the disclosure here provides for recombinant host cells genetically modified to express an FGE that is compatible for use with an aldehyde tag of a tagged target polypeptide.

In one embodiment, an FGE obtained from *Mycobacterium tuberculosis* (Mtb) is used in the methods disclosed herein. An exemplary Mtb FGE is described in detail in the Examples below. An exemplary Mtb FGE is one having the amino acid sequence provide at GenBank Acc. No. NP_215226 (gi:15607852):

```
                                              (SEQ ID NO: 39)
mltelvdlpg gsfrmgstrf ypeeapihtv tvrafaverh pvtnaqfaef vsatgyvtva eqpldpglyp gvdaadlcpg amvfcptagp vdlrdwrqww dwvpgacwrh pfgrdsdiad raghpvvqva ypdavayarw agrrlpteae weyaarggtt atyawgdqek pggmlmantw qgrfpyrndg algwvgtspv grfpangfgl ldmignvwew tttefyphhr idppstacca pvklataadp tisqtlkggs hlcapeychr yrpaarspqs qdtatthigf rcvadpvsg
```

Thus Mtb FGE, and nucleic acid encoding Mtb FGE, are contemplated of use in the present methods. In addition, the methods used to identify and characterize the Mtb FGE are applicable to the identification and characterization of other FGEs useful in the methods disclosed herein.

Provided with the extensive amino acid sequence information and characterization of FGEs provided herein as well as in the art, it will be readily apparent to the ordinarily skilled artisan that FGEs includes naturally-occurring FGEs as well as modified FGEs sharing sequence identity with a known FGE (e.g., a naturally-occurring FGE) and which retain function in specific modification of a serine or cysteine of a sulfatase motif.

In general, FGEs of interest include those having at least 60%, usually 75%, usually 80%, more usually 90%-95% nucleotide or amino acid residue identity, when compared and aligned for maximum correspondence with a nucleotide sequence or amino acid sequence of a parent FGE, as measured using a sequence comparison algorithm available in the art or by visual inspection. Usually a recited sequence identity exists over a region of the sequences that is at least about 50 residues in length, more usually over a region of at least about 100 residues, and more usually over at least about 150 residues up to the full-length of the coding region or protein, with the proviso that the region of comparison includes an active site of the FGE required for enzymatic activity.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschuel et al. (1977) Nucleic Acids Res. 25: 3389-3402, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra).

These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more usually less than about 0.01, and most usually less than about 0.001.

Residue positions that are not identical may differ by conservative amino acid substitutions, which will be readily apparent from analysis of the alignments as discussed above. Conservative amino acid substitutions refer to the interchangeability of residues having similar side chains. For example, amino acid groups defining residues which can be interchanged for another residue within the group and constitute a conservative amino acid substitution include a group of amino acids having aliphatic side chains is glycine, alanine, valine, leucine, proline, and isoleucine ("aliphatic amino acid"); a group of amino acids having aliphatic-hydroxyl side chains is serine, and threonine ("aliphatic, hydroxyl amino acid", which are also encompassed within "polar, uncharged amino acid"); a group of amino acids having amide-containing side chains is asparagine and glutamine ("amide-containing amino acid",", which are also encompassed within "polar, uncharged amino acid"); a group of amino acids having aromatic side chains is phenylalanine, tyrosine, and tryptophan ("aromatic amino acid"); a group of amino acids having basic side chains (at physiological pH) is lysine, arginine, and histidine ("basic amino acid"); a group of amino acids having sulfur-containing side chains is cysteine and methionine ("sulfur-containing amino acid"); a group of amino acids that are polar and uncharged (at physiological pH) include serine, threonine, asparagine, and glutamine ("polar, uncharged amino acid"); and a group of amino acids have charged side chains (at physiological pH) is aspartic acid, glutamic acid, histidine, lysine, and arginine ("charged amino acid"). Conservative amino acids substitution groups are exemplified by: valine-leucine-isoleucine, phenylalanine-tyrosine, lysine-arginine, alanine-valine, and asparagine-glutamine.

Where a cell-free methods is used to convert a sulfatase motif-containing polypeptide, an isolated FGE can be used. Any convenient protein purification procedures may be used to isolate an FGE, see, e.g., Guide to Protein Purification, (Deuthser ed.) (Academic Press, 1990). For example, a lysate may prepared from a cell the produces a desired FGE, and purified using HPLC, exclusion chromatography, gel electrophoresis, affinity chromatography, and the like.

Expression Vectors and Host Cells for Production of Aldehyde Tagged-Polypeptides The disclosure provides a nucleic acid encoding aldehyde tags and aldehyde tagged polypeptides, as well as constructs and host cells containing nucleic acid. Such nucleic acids comprise a sequence of DNA having an open reading frame that encodes an aldehyde tag or aldehyde tagged polypeptide and, in most embodiments, is capable, under appropriate conditions, of being expressed. "Nucleic acid" encompasses DNA, cDNA, mRNA, and vectors comprising such nucleic acids.

Nucleic acids encoding aldehyde tags, as well as aldehyde tagged polypeptides, are provided herein. Such nucleic acids include genomic DNAs modified by insertion of an aldehyde tag-encoding sequence and cDNAs of aldehyde tagged polypeptides. The term "cDNA" as used herein is intended to include all nucleic acids that share the arrangement of sequence elements found in a native mature mRNA species (including splice variants), where sequence elements are exons and 3' and 5' non-coding regions. Normally mRNA species have contiguous exons, with the intervening introns, when present, being removed by nuclear RNA splicing, to create a continuous open reading frame encoding a protein according to the subject invention.

The term "gene" intends a nucleic acid having an open reading frame encoding a polypeptide (e.g., an aldehyde tagged polypeptide), and, optionally, any introns, and can further include adjacent 5' and 3' non-coding nucleotide sequences involved in the regulation of expression (e.g., regulators of transcription and/or translation, e.g., promoters, enhancers, translational regulatory signals, and the like), up to about 20 kb beyond the coding region, but possibly further in either direction, which adjacent 5' and 3' non-coding nucleotide sequences may be endogenous or heterologous to the coding sequence. Transcriptional and translational regulatory sequences, such as promoters, enhancers, etc., may be included. including about 1 kb, but possibly more, of flanking genomic DNA at either the 5' or 3' end of the transcribed region.

Nucleic acids contemplated herein can be provided as part of a vector (also referred to as a construct), a wide variety of which are known in the art and need not be elaborated upon herein. Exemplary vectors include, but are not limited to, plasmids; cosmids; viral vectors (e.g., retroviral vectors); non-viral vectors; artificial chromosomes (YAC's, BAC's, etc.); mini-chromosomes; and the like.

The choice of vector will depend upon a variety of factors such as the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal. The choice of appropriate vector is well within the skill of the art. Many such vectors are available commercially.

To prepare the constructs, a polynucleotide is inserted into a vector, typically by means of DNA ligase attachment to a cleaved restriction enzyme site in the vector. Alternatively, the desired nucleotide sequence can be inserted by homologous recombination or site-specific recombination. Typically homologous recombination is accomplished by attaching regions of homology to the vector on the flanks of the desired nucleotide sequence, while site-specific recombination can be accomplished through use of sequences that facilitate site-specific recombination (e.g., cre-lox, att sites, etc.). Nucleic acid containing such sequences can be added by, for example, ligation of oligonucleotides, or by polymerase chain reaction using primers comprising both the region of homology and a portion of the desired nucleotide sequence.

Vectors can provide for extrachromosomal maintenance in a host cell or can provide for integration into the host cell genome. Vectors are amply described in numerous publications well known to those in the art, including, e.g., Short Protocols in Molecular Biology, (1999) F. Ausubel, et al., eds., Wiley & Sons. Vectors may provide for expression of the nucleic acids encoding a polypeptide of interest (e.g., an aldehyde tagged polypeptide, an FGE, etc.), may provide for propagating the subject nucleic acids, or both.

Exemplary vectors that may be used include but are not limited to those derived from recombinant bacteriophage DNA, plasmid DNA or cosmid DNA. For example, plasmid vectors such as pBR322, pUC 19/18, pUC 118, 119 and the M13 mp series of vectors may be used. Bacteriophage vectors may include λt10, λgt11, λt18-23, λZAP/R and the EMBL series of bacteriophage vectors. Cosmid vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors. Alternatively, recombinant virus vectors may be engineered, including but not limited to those derived from viruses such as herpes virus, retroviruses, vaccinia virus, poxviruses, adenoviruses, adeno-associated viruses or bovine papilloma virus.

For expression of a polypeptide of interest, an expression cassette may be employed. Thus, the present invention provides a recombinant expression vector comprising a subject nucleic acid. The expression vector provides a transcriptional and translational regulatory sequences, and may provide for inducible or constitutive expression, where the coding region is operably linked under the transcriptional control of the transcriptional initiation region, and a transcriptional and translational termination region. These control regions may be native to the gene encoding the polypeptide (e.g., the target polypeptide or the FGE), or may be derived from exogenous sources. In general, the transcriptional and translational regulatory sequences may include, but are not limited to, promoter sequences, ribosomal binding sites, transcriptional start and stop sequences, translational start and stop sequences, and enhancer or activator sequences. In addition to constitutive and inducible promoters, strong promoters (e.g., T7, CMV, and the like) find use in the constructs described herein, particularly where high expression levels are desired in an in vivo (cell-based) or in an in vitro expression system. Further exemplary promoters include mouse mammary tumor virus (MMTV) promoters, Rous sarcoma virus (RSV) promoters, adenovirus promoters, the promoter from the immediate early gene of human CMV (Boshart et al., *Cell* 41:521-530, 1985), and the promoter from the long terminal repeat (LTR) of RSV (Gorman et al., *Proc. Natl. Acad. Sci. USA* 79:6777-6781, 1982). The promoter can also be provided by, for example, a 5'UTR of a retrovirus.

Expression vectors generally have convenient restriction sites located near the promoter sequence to provide for the insertion of nucleic acid sequences encoding proteins of interest. A selectable marker operative in the expression host may be present to facilitate selection of cells containing the vector. In addition, the expression construct may include additional elements. For example, the expression vector may have one or two replication systems, thus allowing it to be maintained in organisms, for example in mammalian or insect cells for expression and in a prokaryotic host for cloning and amplification. In addition the expression construct may contain a selectable marker gene to allow the selection of transformed host cells. Selection genes are well known in the art and will vary with the host cell used.

An aldehyde tag cassette is also provided herein, which includes a nucleic acid encoding an aldehyde tag, and suitable restriction sites flanking the tag-encoding sequence for in-frame insertion of a nucleic acid encoding a target polypeptide. Such an expression construct can provide for addition of an aldehyde tag at the N-terminus or C-terminus of a target polypeptide. The aldehyde tag cassette can be operably linked to a promoter sequence to provide for expression of the resulting aldehyde tagged polypeptide, and may further include one or more selectable markers.

The present disclosure also provides expression cassettes for production of aldehyde tagged-polypeptides (e.g., having an aldehyde tag positioned at a N-terminus, at a C-terminus). Such expression cassettes generally include a first nucleic acid comprising an aldehyde tag-encoding sequence, and at least one restriction site for insertion of a second nucleic acid encoding a polypeptide of interest. The restriction sites can be positioned 5' and/or 3' of the aldehyde tag-encoding sequence. Insertion of the polypeptide-encoding sequence in-frame with the aldehyde tag-encoding sequence provides for production of a recombinant nucleic acid encoding a fusion protein that is an aldehyde tagged polypeptide as described herein. Constructs containing such an expression cassette generally also include a promoter operably linked to the expression cassette to provide for expression of the aldehyde tagged-polypeptide produced. Other components of the expression construction can include selectable markers and other suitable elements.

Expression constructs encoding aldehyde tagged polypeptides can also be generated using amplification methods (e.g., polymerase chain reaction (PCR)), where at least one amplification primer (i.e., at least one of a forward or reverse primer) includes a nucleic acid sequence encoding an aldehyde tag. For example, an amplification primer having an aldehyde tag-encoding sequence is designed to provide for amplification of a nucleic acid encoding a target polypeptide of interest. The extension product that results from polymerase-mediated synthesis from the aldehyde tag-containing forward primer produces a nucleic acid amplification product encoding a fusion protein composed of an aldehyde tagged-target polypeptide. The amplification product is then inserted into an expression construct of choice to provide an aldehyde tagged polypeptide expression construct.

Host Cells

Any of a number of suitable host cells can be used in the production of an aldehyde tagged polypeptide. The host cell used for production of an aldehyde tagged-polypeptide can optionally provide for FGE-mediated conversion, so that the polypeptide produced contains an FGly-containing aldehyde tag following expression and post-translational modification by FGE. Alternatively the host cell can provide for production of an unconverted aldehyde tagged polypeptide (e.g., due to lack of expression of an FGE that facilitates conversion of the aldehyde tag).

In general, the polypeptides described herein may be expressed in prokaryotes or eukaryotes in accordance with conventional ways, depending upon the purpose for expression. Thus, the present invention further provides a host cell, e.g., a genetically modified host cell, that comprises a nucleic acid encoding an aldehyde tagged polypeptide. The host cell can further optionally comprise a recombinant FGE, which may be endogenous or heterologous to the host cell.

Host cells for production (including large scale production) of an unconverted or (where the host cell expresses a suitable FGE) converted aldehyde tagged polypeptide, or for production of an FGE (e.g., for use in a cell-free method) can be selected from any of a variety of available host cells. Exemplary host cells include those of a prokaryotic or eukaryotic unicellular organism, such as bacteria (e.g., *Escherichia coli* strains, *Bacillus* spp. (e.g., *B. subtilis*), and the like) yeast or fungi (e.g., *S. cerevisiae, Pichia* spp., and the like), and other such host cells can be used. Exemplary host cells originally derived from a higher organism such as insects, vertebrates, particularly mammals, (e.g. CHO, HEK, and the like), may be used as the expression host cells.

Specific expression systems of interest include bacterial, yeast, insect cell and mammalian cell derived expression systems. Representative systems from each of these categories are provided below.

Bacteria. Expression systems in bacteria include those described in Chang et al., *Nature* (1978) 275:615; Goeddel et al., *Nature* (1979) 281:544; Goeddel et al., *Nucleic Acids Res.* (1980) 8:4057; EP 0 036,776; U.S. Pat. No. 4,551,433; DeBoer et al., *Proc. Natl. Acad. Sci.* (*USA*) (1983) 80:21-25; and Siebenlist et al., *Cell* (1980) 20:269.

Yeast. Expression systems in yeast include those described in Hinnen et al., *Proc. Natl. Acad. Sci.* (*USA*) (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459; Roggenkamp et al., *Mol. Gen. Genet.* (1986) 202:302; Das et al., *J. Bacteriol.* (1984) 158:1165; De Louvencourt et al., *J. Bacteriol.* (1983) 154:737; Van den Berg et al., *Bio/Technology* (1990) 8:135; Kunze et al., *J. Basic Microbiol.* (1985) 25:141; Cregg et al., *Mol. Cell. Biol.* (1985) 5:3376; U.S. Pat. Nos. 4,837,148 and 4,929,555; Beach and Nurse, *Nature* (1981) 300:706; Davidow et al., *Curr. Genet.* (1985)10:380; Gaillardin et al., *Curr. Genet.* (1985) 10:49; Ballance et al., *Biochem. Biophys. Res. Commun.* (1983) 112:284-289; Tilburn et al., *Gene* (1983) 26:205-221; Yelton et al., *Proc. Natl. Acad. Sci.* (*USA*) (1984) 81:1470-1474; Kelly and Hynes, *EMBO J.* (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol.* (1988) 69:765-776; Miller et al., *Ann. Rev. Microbiol.* (1988) 42:177; Carbonell et al., *Gene* (1988) 73:409; Maeda et al., *Nature* (1985) 315:592-594; Lebacq-Verheyden et al., *Mol. Cell. Biol.* (1988) 8:3129; Smith et al., *Proc. Natl. Acad. Sci.* (*USA*) (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47-55, Miller et al., *Generic Engineering* (1986) 8:277-279, and Maeda et al., *Nature* (1985) 315:592-594.

Mammalian Cells. Mammalian expression is accomplished as described in Dijkema et al., *EMBO J.* (1985) 4:761, Gorman et al., *Proc. Natl. Acad. Sci.* (*USA*) (1982) 79:6777, Boshart et al., *Cell* (1985) 41:521 and U.S. Pat. No. 4,399, 216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. RE 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism.

The product can be recovered by any appropriate means known in the art. Further, any convenient protein purification procedures may be employed, where suitable protein purification methodologies are described in Guide to Protein Purification, (Deuthser ed.) (Academic Press, 1990). For example, a lysate may prepared from a cell comprising the expression vector expressing a polypeptide of interest, and purified using HPLC, exclusion chromatography, gel electrophoresis, affinity chromatography, and the like.

Moieties for Modification of Polypeptides

The aldehyde tagged, FGly-containing polypeptides can be subjected to modification to provide for attachment of a wide variety of moieties. Exemplary molecules of interest include, but are not necessarily limited to, a detectable label, a small molecule, a peptide, and the like.

The moiety of interest is provided as component of a reactive partner for reaction with an aldehyde of the FGly residue of a converted aldehyde tag of the tagged polypeptide. Since the methods of tagged polypeptide modification are compatible with conventional chemical processes, the methods of the invention can exploit a wide range of commercially available reagents to accomplish attachment of a moiety of interest to a FGly residue of an aldehyde tagged polypeptide. For example, aminooxy, hydrazide, hydrazine, or thiosemicarbazide derivatives of a number of moieties of interest are suitable reactive partners, and are readily available or can be generated using standard chemical methods.

For example, an aminooxy-PEG can be generated from monoamino-PEGs and aminooxyglycine using standard protocols. The aminooxy-PEG can then be reacted with a converted aldehyde tagged polypeptide to provide for attachment of the PEG moiety. Delivery of a biotin moiety to a converted aldehyde tagged polypeptide can be accomplished using aminooxy biotin, biotin hydrazide or 2,4 dinitrophenylhydrazine.

Provided the present disclosure, the ordinarily skilled artisan can readily adapt any of a variety of moieties to provide a reactive partner for conjugation to an aldehyde tagged polypeptide as contemplated herein. The ordinarily skilled artisan will appreciate that factors such as pH and steric hindrance (i.e., the accessibility of the aldehyde tag to reaction with a reactive partner of interest) are of importance, Modifying reaction conditions to provide for optimal conjugation conditions is well within the skill of the ordinary artisan, and is routine in the art. In general, it is normally desirable to conduction conjugation reactions at a pH below 7, with a pH of about 5.5, about 6, about 6.5, usually about 5.5 being optimal. Where conjugation is conducted with an aldehyde tagged polypeptide present in or on a living cell, the conditions are selected so as to be physiologically compatible. For example, the pH can be dropped temporarily for a time sufficient to allow for the reaction to occur but within a period tolerated by the cell having an aldehyde tag (e.g., from about 30 min to 1 hour). Physiological conditions for conducting modification of aldehyde tagged polypeptides on a cell surface can be similar to those used in a ketone-azide reaction in modification of cells bearing cell-surface azides (see, e.g., U.S. Pat. No. 6,570,040).

In general, the moiety or moieties can provide for one or more of a wide variety of functions or features. Exemplary moieties include detectable labels (e.g., dye labels (e.g., chromophores, fluorophores), biophysical probes (spin labels, NMR probes), FRET-type labels (e.g., at least one member of a FRET pair, including at least one member of a fluorophore/quencher pair), BRET-type labels (e.g., at least one member of a BRET pair), immunodetectable tags (e.g., FLAG, His(6), and the like), localization tags (e.g., to identify association of a tagged polypeptide at the tissue or molecular cell level (e.g., association with a tissue type, or particular cell membrane)), and the like); light-activated dynamic moieties (e.g., azobenzene mediated pore closing, azobenzene mediated structural changes, photodecaging recognition motifs); water soluble polymers (e.g., PEGylation); purification tags (e.g., to facilitate isolation by affinity chromatography (e.g., attachment of a FLAG epitope)); membrane localization domains (e.g., lipids or GPI-type anchors); immobilization tags (e.g., to facilitate attachment of the polypeptide to a surface, including selective attachment); drugs (e.g., to facilitate drug targeting, e.g., through attachment of the drug to an antibody); targeted delivery moieties, (e.g., ligands for binding to a target receptor (e.g., to facilitate viral attachment, attachment of a targeting protein present on a liposome, etc.)), and the like.

Specific, non-limiting examples are provided below.

Detectable Labels.

The compositions and methods of the invention can be used to deliver a detectable label to an aldehyde tagged polypeptide. Exemplary detectable labels include, but are not necessarily limited to, fluorescent molecules (e.g., autofluorescent molecules, molecules that fluoresce upon contact with a reagent, etc.), radioactive labels (e.g., $^{111}$In, $^{125}$I, $^{131}$I, $^{212}$B, $^{90}$Y, $^{186}$Rh, and the like); biotin (e.g., to be detected through reaction of biotin and avidin); fluorescent tags; imaging reagents, and the like. Detectable labels also include peptides or polypeptides that can be detected by antibody binding, e.g., by binding of a detectably labeled antibody or by detection of bound antibody through a sandwich-type assay.

Attachment of Target Molecules to a Support.

The methods can provide for conjugation of an aldehyde tagged polypeptide to a moiety to facilitate attachment of the polypeptide to a solid substratum (e.g., to facilitate assays), or to a moiety to facilitate easy separation (e.g., a hapten recognized by an antibody bound to a magnetic bead). In one embodiment, the methods of the invention are used to provide for attachment of a protein to an array (e.g., chip) in a defined orientation. For example, a polypeptide having an aldehyde tag at a selected site (e.g., at or near the N-terminus) can be generated, and the methods and compositions of the invention used to deliver a moiety to the converted aldehyde tag. The moiety can then be used as the attachment site for affixing the polypeptide to a support (e.g., solid or semi-solid support, particularly a support suitable for use as a microchip in high-throughput assays).

Attachment of Molecules for Delivery to a Target Site.

The reactive partner for the aldehyde tagged polypeptide can comprise a small molecule drug, toxin, or other molecule for delivery to the cell and which can provide for a pharmacological activity or can serve as a target for delivery of other molecules.

Also contemplated is use of a reactive partner that comprises one of a pair of binding partners (e.g., a ligand, a ligand-binding portion of a receptor, a receptor-binding portion of a ligand, etc.). For example, the reactive partner can comprise a polypeptide that serves as a viral receptor and, upon binding with a viral envelope protein or viral capsid protein, facilitates attachment of virus to the cell surface on which the modified aldehyde tagged protein is expressed. Alternatively, the reactive partner comprises an antigen that is specifically bound by an antibody (e.g., monoclonal antibody), to facilitate detection and/or separation of host cells expressing the modified aldehyde tagged polypeptide.

Water-Soluble Polymers

A moiety of particular interest is a water-soluble polymer. A "water-soluble polymer" refers to a polymer that is soluble in water and is usually substantially non-immunogenic, and usually has an atomic molecular weight greater than about 1,000 Daltons. The methods and compositions described herein can be used to attach one or more water-soluble polymers to an aldehyde tagged polypeptide. Attachment of a water-soluble polymer (e.g., PEG) of a polypeptide, particularly a pharmaceutically active (therapeutic) polypeptide can be desirable as such modification can increase therapeutic index by increasing serum half-life as a result of increased proteolytic stability and/or decreased renal clearance. Additionally, attachment of one or more polymers (e.g., PEGylation) can reduce immunogenicity of protein pharmaceuticals.

In some embodiments, the water-soluble polymer has an effective hydrodynamic molecular weight of greater than about 10,000 Da, greater than about 20,000 to 500,000 Da, greater than about 40,000 Da to 300,000 Da, greater than about 50,000 Da to 70,000 Da, usually greater than about 60,000 Da. By "effective hydrodynamic molecular weight" is intended the effective water-solvated size of a polymer chain as determined by aqueous-based size exclusion chromatography (SEC). When the water-soluble polymer contains polymer chains having polyalkylene oxide repeat units, such as ethylene oxide repeat units, each chain can have an atomic molecular weight of between about 200 Da and about 80,000

Da, or between about 1,500 Da and about 42,000 Da, with 2,000 to about 20,000 Da being of particular interest. Unless referred to specifically, molecular weight is intended to refer to atomic molecular weight. Linear, branched, and terminally charged water soluble polymers (e.g., PEG) are of particular interest.

Polymers useful as moieties to be attached to an aldehyde tagged polypeptide can have a wide range of molecular weights, and polymer subunits. These subunits may include a biological polymer, a synthetic polymer, or a combination thereof. Examples of such water-soluble polymers include: dextran and dextran derivatives, including dextran sulfate, P-amino cross linked dextrin, and carboxymethyl dextrin, cellulose and cellulose derivatives, including methylcellulose and carboxymethyl cellulose, starch and dextrines, and derivatives and hydroylactes of starch, polyalklyene glycol and derivatives thereof, including polyethylene glycol, methoxypolyethylene glycol, polyethylene glycol homopolymers, polypropylene glycol homopolymers, copolymers of ethylene glycol with propylene glycol, wherein said homopolymers and copolymers are unsubstituted or substituted at one end with an alkyl group, heparin and fragments of heparin, polyvinyl alcohol and polyvinyl ethyl ethers, polyvinylpyrrolidone, aspartamide, and polyoxyethylated polyols, with the dextran and dextran derivatives, dextrine and dextrine derivatives. It will be appreciated that various derivatives of the specifically recited water-soluble polymers are also contemplated.

Water-soluble polymers such as those described above are well known, particularly the polyalkylene oxide based polymers such as polyethylene glycol "PEG" (See. e.g., "Poly (ethylene glycol) Chemistry: Biotechnical and Biomedical Applications", J. M. Harris, Ed., Plenum Press, New York, N.Y. (1992); and "Poly(ethylene glycol) Chemistry and Biological Applications", J. M. Harris and S. Zalipsky, Eds., ACS (1997); and International Patent Applications: WO 90/13540, WO 92/00748, WO 92/16555, WO 94/04193, WO 94/14758, WO 94/17039, WO 94/18247, WO 94/28937, WO 95/11924, WO 96/00080, WO 96/23794, WO 98/07713, WO 98/41562, WO 98/48837, WO 99/30727, WO 99/32134, WO 99/33483, WO 99/53951, WO 01/26692, WO 95/13312, WO 96/21469, WO 97/03106, WO 99/45964, and U.S. Pat. Nos. 4,179,337; 5,075,046; 5,089,261; 5,100,992; 5,134,192; 5,166,309; 5,171,264; 5,213,891; 5,219,564; 5,275,838; 5,281,698; 5,298,643; 5,312,808; 5,321,095; 5,324,844; 5,349,001; 5,352,756; 5,405,877; 5,455,027; 5,446,090; 5,470,829; 5,478,805; 5,567,422; 5,605,976; 5,612,460; 5,614,549; 5,618,528; 5,672,662; 5,637,749; 5,643,575; 5,650,388; 5,681,567; 5,686,110; 5,730,990; 5,739,208; 5,756,593; 5,808,096; 5,824,778; 5,824,784; 5,840,900; 5,874,500; 5,880,131; 5,900,461; 5,902,588; 5,919,442; 5,919,455; 5,932,462; 5,965,119; 5,965,566; 5,985,263; 5,990,237; 6,011,042; 6,013,283; 6,077,939; 6,113,906; 6,127,355; 6,177,087; 6,180,095; 6,194,580; 6,214,966).

Exemplary polymers of interest include those containing a polyalkylene oxide, polyamide alkylene oxide, or derivatives thereof, including polyalkylene oxide and polyamide alkylene oxide comprising an ethylene oxide repeat unit of the formula —($CH_2$—$CH_2$—O)—. Further exemplary polymers of interest include a polyamide having a molecular weight greater than about 1,000 Daltons of the formula —[C(O)—X—C(O)—NH—Y—NH]n- or —[NH—Y—NH—C(O)—X—C(O)]$_n$—, where X and Y are divalent radicals that may be the same or different and may be branched or linear, and n is a discrete integer from 2-100, usually from 2 to 50, and where either or both of X and Y comprises a biocompatible, substantially non-antigenic water-soluble repeat unit that may be linear or branched. Further exemplary water-soluble repeat units comprise an ethylene oxide of the formula —($CH_2$—$CH_2$—O)— or —($CH_2$—$CH_2$—O)—. The number of such water-soluble repeat units can vary significantly, with the usual number of such units being from 2 to 500, 2 to 400, 2 to 300, 2 to 200, 2 to 100, and most usually 2 to 50. An exemplary embodiment is one in which one or both of X and Y is selected from: —(($CH_2$)$_{n1}$—($CH_2$—$CH_2$—O)$_{n2}$—($CH_2$)— or —(($CH_2$)$_{n1}$—(O—$CH_2$—$CH_2$)$_{n2}$—($CH_2$)$_{n-1}$—), where n1 is 1 to 6, 1 to 5, 1 to 4 and most usually 1 to 3, and where n2 is 2 to 50, 2 to 25, 2 to 15, 2 to 10, 2 to 8, and most usually 2 to 5. A further exemplary embodiment is one in which X is —($CH_2$—$CH_2$)—, and where Y is —($CH_2$—($CH_2$—$CH_2$—O)$_3$—$CH_2$—$CH_2$—$CH_2$)— or —($CH_2$—$CH_2$—$CH_2$—(O—$CH_2$—$CH_2$)$_3$—$CH_2$)—.

The polymer can include one or more spacers or linkers. Exemplary spacers or linkers include linear or branched moieties comprising one or more repeat units employed in a water-soluble polymer, diamino and or diacid units, natural or unnatural amino acids or derivatives thereof, as well as aliphatic moieties, including alkyl, aryl, heteroalkyl, heteroaryl, alkoxy, and the like, which can contain, for example, up to 18 carbon atoms or even an additional polymer chain.

The polymer moiety, or one or more of the spacers or linkers of the polymer moiety when present, may include polymer chains or units that are biostable or biodegradable. For example, Polymers with repeat linkages have varying degrees of stability under physiological conditions depending on bond lability. Polymers with such bonds can be categorized by their relative rates of hydrolysis under physiological conditions based on known hydrolysis rates of low molecular weight analogs, e.g., from less stable to more stable, e.g., polyurethanes (—NH—C(O)—O—)>polyorthoesters (—O—C((OR)(R))—O—)>polyamides (—C(O)—NH—). Similarly, the linkage systems attaching a water-soluble polymer to a target molecule may be biostable or biodegradable, e.g., from less stable to more stable: carbonate (—O—C(O)—O—)>ester (—C(O)—O—)>urethane (—NH—C(O)—O—)>orthoester (—O—C((OR)(R'))—O—)>amide (—C(O)—NH—). In general, it may be desirable to avoid use of sulfated polysaccharide, depending on the lability of the sulfate group. In addition, it may be less desirable to use polycarbonates and polyesters. These bonds are provided by way of example, and are not intended to limit the types of bonds employable in the polymer chains or linkage systems of the water-soluble polymers useful in the modified aldehyde tagged polypeptides disclosed herein.

Methods for Conversion and Modification of an Aldehyde Tag

Conversion of an aldehyde tag present in an aldehyde tagged polypeptide accomplished by cell-based (in vivo) or cell-free methods (in vitro). Similarly, modification of a converted aldehyde tag of an aldehyde tagged polypeptide can be accomplished by cell-based (in vivo) or cell-free methods (in vitro). These are described in more detail below.

"In Vivo" Host Cells Conversion and Modification

Conversion of an aldehyde tag of an aldehyde tagged polypeptide can be accomplished by expression of the aldehyde tagged polypeptide in a cell that contains a suitable FGE. In this embodiment, conversion of the cysteine or serine of the aldehyde tag is occurs during or following translation in the host cell. In this embodiment, the FGE of the host cell can be endogenous to the host cell, or the host cell can be recombinant for a suitable FGE that is heterologous to the host cell. FGE expression can be provided by an expression system endogenous to the FGE gene (e.g., expression is provided by a promoter and other control elements present in the native FGE gene of the host cell), or can be provided by from a recombinant expression system in which the FGE coding sequence is operably linked to a heterologous promoter to provide for constitutive or inducible expression. Use of a strong promoter to provide high levels of FGE expression may be of particular interest in some embodiment.

Depending on the nature of the target polypeptide containing the aldehyde tag, following conversion the converted aldehyde tagged polypeptide is either retained in the host cell intracellularly, is secreted, or is associated with the host cell extracellular membrane. Where the aldehyde tag of the aldehyde tagged polypeptide is present at the cell surface, modification of the converted aldehyde tag can be accomplished by use of a reactive partner to attach a moiety of the reactive partner to a FGly residue of a surface accessible aldehyde tag under physiological conditions. Conditions suitable for use to accomplish conjugation of a reactive partner moiety to an aldehyde tagged polypeptide are similar to those described in Mahal et al. (1997 May 16) Science 276(5315):1125-8.

"In Vitro" (Cell-Free) Conversion and Modification

In vitro (cell-free) conversion of an aldehyde tag of an aldehyde tagged polypeptide can be accomplished by contacting an aldehyde tagged polypeptide with an FGE under conditions suitable for conversion of a cysteine or serine of a sulfatase motif of the aldehyde tag to a FGly. For example, nucleic acid encoding an aldehyde tagged polypeptide can be expression in an in vitro transcription/translation system in the presence of a suitable FGE to provide for production of converted aldehyde tagged polypeptides.

Alternatively, isolated, unconverted aldehyde tagged polypeptide can be isolated following recombinant production in a host cell lacking a suitable FGE or by synthetic production. The isolated aldehyde tagged polypeptide is then contacted with a suitable FGE under conditions to provide for aldehyde tag conversion. In this embodiment, if the aldehyde tag may not be readily solvent accessible in the isolated polypeptide, the aldehyde tagged polypeptide can be unfolded by methods known in the art (e.g., using heat, adjustment of pH, chaotropic agents, (e.g., urea, and the like), organic solvents (e.g., hydrocarbons: octane, benzene, chloroform), etc.) and the denatured protein contacted with a suitable FGE. The converted aldehyde tagged polypeptide can then be refolded under suitable conditions.

With respect to modification of converted aldehyde tagged, modification is normally carried out in vitro. Converted aldehyde tagged polypeptide is isolated from a production source (e.g., recombinant host cell production, synthetic production), and contacted with a reactive partner under conditions suitable to provide for conjugation of a moiety of the reactive partner to the FGly of the aldehyde tag. If the aldehyde tag is not solvent accessible, the aldehyde tagged polypeptide can be unfolded by methods known in the art prior to reaction with a reactive partner.

Switchable Moieties Attached to Aldehyde Tag

In some embodiments, aldehyde tagged polypeptides can be modified in a manner so as to facilitate removal of a conjugated moiety at the FGly residue of the aldehyde tag and replacement with a different moiety. This aspect of the invention exploits the relative thermodynamic stability of conjugates formed with different reactive partners.

Figure 6:
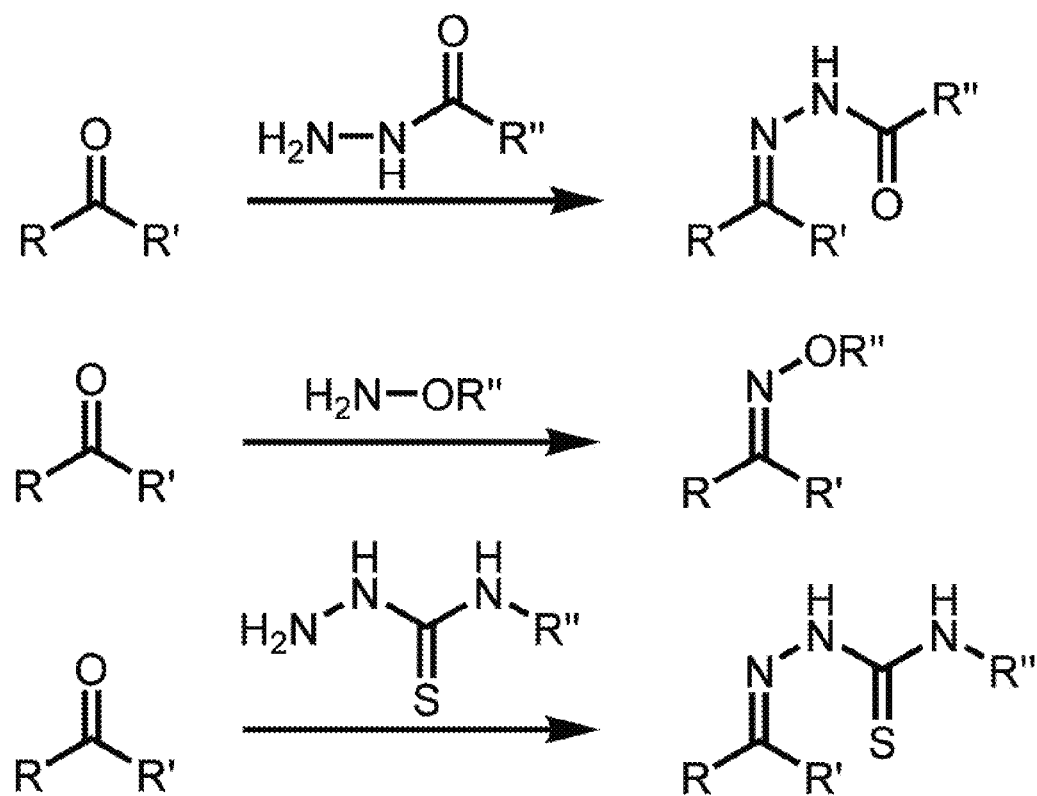
FIG. 6 illustrates generation of hydrazone, oxime and semicarbazone linkages. R and R' refer to suitable substituents which appear in the aldehyde tagged polypeptide as disclosed herein. R" refers to a substituent of the reagent which is transferred to the aldehyde tagged polypeptide in the reaction product.

For example, as illustrated in FIG. 6, aldehydes readily react with hydrazide and aminooxy moieties to yield hydrazones and oximes, respectively. Although both of these conjugates are robust under physiological conditions, oximes are more thermodynamically stable. Moreover, thiosemicarbazides also readily react with aldehydes to form thiosemicarbazone conjugates, which are less thermodynamically stable than oximes. These differences in thermodynamic stability can be exploited for switching the lower stability hydrazone conjugate to a more stable oxime conjugate, and for switching the lower stability oxime conjugate to a more stable semicarbazone conjugate. This feature of the aldehyde tag allows the modification of the target protein with two reagents in sequence (i.e., sequentially), as illustrated in the Example below.

Modified Aldehyde Tagged Polypeptides

The reaction products produced by reaction of an aldehyde tagged polypeptide with a reactive partner comprising a moiety of interest are generally modified in a site-specific manner (i.e., at the FGly residue), providing for a substantially homogenous population modified aldehyde tagged polypeptides. Heterogenous populations of such reaction products can be generated by use of two or more reactive partners comprising different moieties, where desired.

For example, where the target polypeptide is modified by PEGylation, the methods can be adapted to provide for production of a homogenous population of PEGylated polypeptides (in which the polypeptides are modified with the same PEG moieties) or a heterogenous population of PEGylated polypeptides (in which the polypeptides in the composition are modified with different types of PEG molecules).

Kits and Systems

Kits and systems are provided to facilitate and, where desired, standardize the compositions of the invention and the uses thereof. Kits contemplated herein can include one or more of a construct encoding an aldehyde tag for insertion into a target polypeptide; a construct encoding an aldehyde tagged polypeptide for expression in a host cell (e.g., as an expression cassette to provide for insertion of a coding sequence of a target polypeptide as a N-terminal or C-terminal fusion with the aldehyde tag); a host cell that produces an FGE compatible with an aldehyde tag of the kit, where the FGE may be endogenous, recombinant, or heterologous; a host cell genetically modified to express an aldehyde tagged polypeptide of interest, which host cell can further express an endogenous, recombinant, or heterologous FGE compatible for conversion of the aldehyde tag of the tagged polypeptide; and a reactive partner for chemical modification of the converted aldehyde tag of the tagged polypeptide.

In addition, the kit can contain instructions for using the components of the kit, particularly the compositions of the invention that are contained in the kit.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials:

The following materials and methods were used in Examples 1-6 set out below.

Plasmid Construction.

The following oligonucleotides were used in the Examples below:

| Primer | Sequence (5' → 3')[a] |
|---|---|
| ald$_6$-stf0 start[b] | CCA<u>CTGTGCACACCATCGCGG</u>ATGTCCGACCACCCCACCGCC (SEQ ID NO: 40) |
| ald$_{13}$-stf0 sense | CATGGCACC<u>ACTGTGCACACCATCGCGGG</u>GCTCGCTGTTCACCGGCCG CGACGTCCA (SEQ ID NO: 41) |
| ald$_{13}$-stf0 antisense | TATGGACGTCGCGGCCGGTGAACAGCGAGCCCCGCGATGGTGTGCACA GTGGTGC (SEQ ID NO: 42) |
| ald-stf0 end | GCACCACCACCACCACCACTGAGATCCGGCTGC (SEQ ID NO: 43) |
| ald-stf0 Cys5Ala[b] | CCATGGCACCACTGG<u>CCACACCATCGCGG</u> (SEQ ID NO: 44) |
| stf0 end[b] | CGGCCGCGATGTGCGCCTTGAAGATCTGC (SEQ ID NO: 45) |
| mbp sense | GATCC<u>CTGTGCACACCATCGCGG</u>GTGAGC (SEQ ID NO: 46) |
| mbp nonsense | GGCCGCTCA<u>CCGCGATGGTGTGCACAG</u>G (SEQ ID NO: 47) |
| ald-mbp Cys5Ala[b] | CCGCGTGGATCCCTGG<u>CCACACCATCGCGG</u> (SEQ ID NO: 48) |
| ald$_6$-hGH start | CTATGCTACCATGG<u>CGCTGTGCACACCATCGCGG</u>ACCATTCCCTTATCC AGGC (SEQ ID NO: 49) |
| hGH end | CTATGCTAGCGGCCGCGAAGCCACAGCTGCCCTCCAC (SEQ ID NO: 50) |
| ald$_6$-hGH Cys5Ala[b] | TATACCATGGCGCTGG<u>CCACACCATCGCGG</u>ACC (SEQ ID NO: 51) |
| fge start | CTATGCTACCATGGCTGACCGAGTTGGTTGACCTGC (SEQ ID NO: 52) |
| fge end | TAGCATAGCTCGAGCTACCCGGACACCGGGTCG (SEQ ID NO: 53) |
| fge in-frame[b] | GAGGAATTAACCATGCTGACCGAGTTGGTTG (SEQ ID NO: 54) |

[a]Aldehyde-encoding bases are underlined.
[b]Site-directed mutagenesis primer. Where appropriate, numbered from the beginning of the respective protein start codon. A pair of complementary primers was used for each mutant. The reverse complements are not shown.

The sulfatase motifs of the constructs are provided below:

ald$_{13}$-Stf0: LCTPSRGSLFTGR-(mycobacterial sulfotransferase)
(SEQ ID NO:55)

ald$_{13}$-Stf0 (C5A): LATPSRGSLFTGR-(mycobacterial sulfotransferase)
(SEQ ID NO:56)

ald$_6$-Stf0: LCTPSR-(mycobacterial sulfotransferase) (SEQ ID NO:1)

ald$_6$-MBP: LCTPSR-(maltose binding protein) (SEQ ID NO:1)

ald$_6$-hGH: LCTPSR-(human growth hormone) (SEQ ID NO:1)

The nucleic acid encoding ald$_{13}$-Stf0 was constructed by ligating annealed oligonucleotides into a previously constructed pET28-Stf0 vector[19] between NcoI and NdeI restriction sites. The stf0 stop codon was removed by Quikchange™ (Stratagene) mutagenesis to allow for a C-terminal His$_6$ tag. ald$_6$Stf0 was constructed using QUICKCHANGE™ (Stratagene) to eliminate the nucleotides that encode the last 7 residues of the 13 amino acid aldehyde tag. The gene encoding ald$_6$-MBP was constructed by ligating annealed oligonucleotides into the pMALc-H vector[19] between XhoI and HindIII restriction sites. The gene encoding hGH (human growth hormone 1 transcript variant 1, encoding residues 29-217) was amplified from pCMV-SPORT6.1.ccdb (Open Biosystems) using a 5' primer that encoded the 6 amino acid aldehyde tag and ligated into pET28b between NcoI and NotI restriction sites. The gene encoding *Mycobacterium tuberculosis* FGE (Rv0712, encoding residues 2-299) was amplified from a previously prepared pET14b plasmid containing FGE[14] and ligated into pBAD/myc-his A (Invitrogen) between NcoI and XhoI restriction sites. The FGE gene was placed in frame with the start codon using QuikChange PCR mutagenesis kit (Stratagene). Cys→Ala mutants of ald-Sft0, ald-MBP, and ald-hGH were produced using QuikChange™ mutagenesis. DNA sequencing was performed to confirm the fidelity of each gene product. Protein-encoding plasmids were transformed into BL21(DE3) *E. coli* cells (Invitrogen).

Protein Expression and Purification.

Clonal populations of BL21(DE3) *E. coli* cells harboring only an aldehyde-tagged protein-encoding plasmid were incubated in LB media with kanamycin with shaking at 37° C. until OD$_{600}$=0.5, at which time the temperature was lowered to 18° C. and 100 μM IPTG was added. BL21(DE3) *E. coli* cells harboring an aldehyde-tagged protein-encoding plasmid and an FGE-encoding plasmid were incubated in LB media with kanamycin and ampicillin with shaking at 37° C. until OD$_{600}$=0.5, at which time the FGE expression was induced with 0.02% arabinose. After 30 min, the temperature was lowered to 18° C. and 100 μM IPTG was added to induce expression of the aldehyde-tagged protein. After 12-16 h, cells were harvested and resuspended in 20 ml of lysis buffer (50 mM Tris, 500 mM NaCl, 10% glycerol, 20 mM imidazole, 1 mM DTT, 1 mM TCEP, 1 mM methionine, pH 7.5, for ald$_6$-hGH or 50 mM NaH$_2$PO$_4$, 300 mM NaCl, 10 mM imidazole, pH 7.4, for ald-Stf0 and ald$_6$-MBP) per liter of culture and lysed by sonication.

Cell lysates were treated with DNase (10 μg/ml), cleared by centrifugation and applied to a 1 ml HisTrap column (GE Healthcare). The column was washed with lysis buffer with 35 mM imidazole and His$_6$-tagged protein was eluted using lysis buffer with 250 mM imidazole. ald$_6$-hGH was further purified on a Sephadex 16/60 S300 column (GE Healthcare).

Tryptic Digestion and Standard Addition Assay.

10 µg of protein was digested with 0.4 µg trypsin (Promega) at 37° C. for 16 hours in 50 mM NH$_4$HCO$_3$ pH 8. This protocol was deemed sufficient for complete digestion as no peptides containing missed cleavage sites were detected by MALDI-TOF mass spectrometry after 3 hours of digestion under identical conditions. Standard addition assays were run in water with about 0.6 µg protein digest per run. Synthetic peptides containing either the cysteine or aldehyde (FGly) were added in equimolar amounts followed by addition of 100 mM DTT. This solution was allowed to incubate at RT for 1 hour prior to mass spectrometry analysis (Agilent MSD). Blank runs were added between randomly selected runs and no residual signal was detected. Cysteine oxidation was not observed.

Small Molecule Labeling.

Fluorescent labeling reactions were run with 10 µg target protein with 300 µM aminooxy dye (Alexa Fluor 647 C5-aminooxyacetamide, Invitrogen) in labeling buffer (100 mM MES pH 5.5, 1% SDS) at 37° C. for 2 hours. 166 mM methoxylamine was added to control reactions. Reaction mixtures were separated by SDS-PAGE and fluorescence was detected using a Typhoon 9410 scanner (GE Healthcare). Protein loading was determined by Sypro Ruby (Sigma) staining. Biotinylation was afforded by incubating 10 µg of target protein with 30 µM biotin hydrazide (Sigma) in labeling buffer for 2 hours at 37° C. Subsequent displacement of biotin hydrazide was afforded by addition of either 166 mM methoxlamine or 1 mM aminooxyFLAG at 37° C. for 2 hours. The α-biotin western blot was performed using standard protocol. The α-FLAG blot was obtained by stripping the membrane and reprobing with α-FLAG M2 (Sigma) Aminooxy-FLAG was synthesized using standard FMOC-based solid phase peptide synthesis protocols. The final residue added, C-terminal, was (t-Boc-aminooxy)acetic acid followed by cleavage under standard conditions.

PEGylation.

Aminooxy-PEGs were created from monoamino-PEGs and aminooxyglycine using standard protocols. More specifically, aminooxyPEGs were produced by adding aminoPEGs (Shearwater Polymers) to activated (t-Boc-aminooxy)acetic acid using standard peptide coupling conditions. Briefly, amide bond formation was accomplished by adding aminoPEG to the preformed 8-hydroxybenzotriazole ester of (t-Boc-aminooxy)acetic acid (5 equivalents) in acetonitrile. Purification of the product was afforded by precipitation from ether, followed by trituration. Deprotection was accomplished by treatment with an aqueous triflouroacetic acid solution (95% TFA, 5% H$_2$O) for 3 hours at RT. Precipitation into ether and trituration afforded a pure product as judged by $^1$H NMR. Conjugation to aldehyde-tagged proteins was afforded by incubation of 10 µg target protein and 10 mM aminooxyPEG in coupling solution (49.95% CH$_3$CN, 49.95% H$_2$O, 0.1% TFA) for 1 hour followed by lyophilization.

Conjugation to aldehyde-tagged proteins was afforded by incubation of 10 µg target protein and 10 mM aminooxyPEG in coupling solution (49.95% CH$_3$CN, 49.95% H$_2$O, 0.1% TFA) for 1 hour followed by lyophilization. Reaction mixtures were resuspended in water, separated by SDS-PAGE, stained with Sypro Orange (Invitrogen) and detected using a Typhoon 9410 scanner (GE Healthcare).

Example 1

Site-Specific Modification of a Sulfatase Motif in Protein Expressed in E. Coli

Protein constructs with either N- or C-terminal aldehyde tags were expressed in E. coli. Three protein targets were explored, a C-terminally tagged maltose binding protein (MBP), an N-terminally tagged human growth hormone (hGH), and an N-terminally tagged mycobacterial sulfotransferase (Stf0). Additionally, two variants of the aldehyde tag were tested—a 13 residue tag (ald$_{13}$-Stf0) that included the entire sulfatase consensus motif, and a 6 residue tag (ald$_6$-Stf0) that included a shorter sequence containing a sulfatase consensus motif:

LCTPSRGSLFTGR-Stf0 (ald$_{13}$-Stf0) (SEQ ID NO:55)
LCTPSR-Stf0 (ald$_6$-Stf0). (SEQ ID NO:1)

In order to ensure efficient formation of FGly, tagged proteins were co-expressed with a prokaryotic FGE from Mycobacterium tuberculosis (Mtb) (described in the Examples below).

Figure 2:
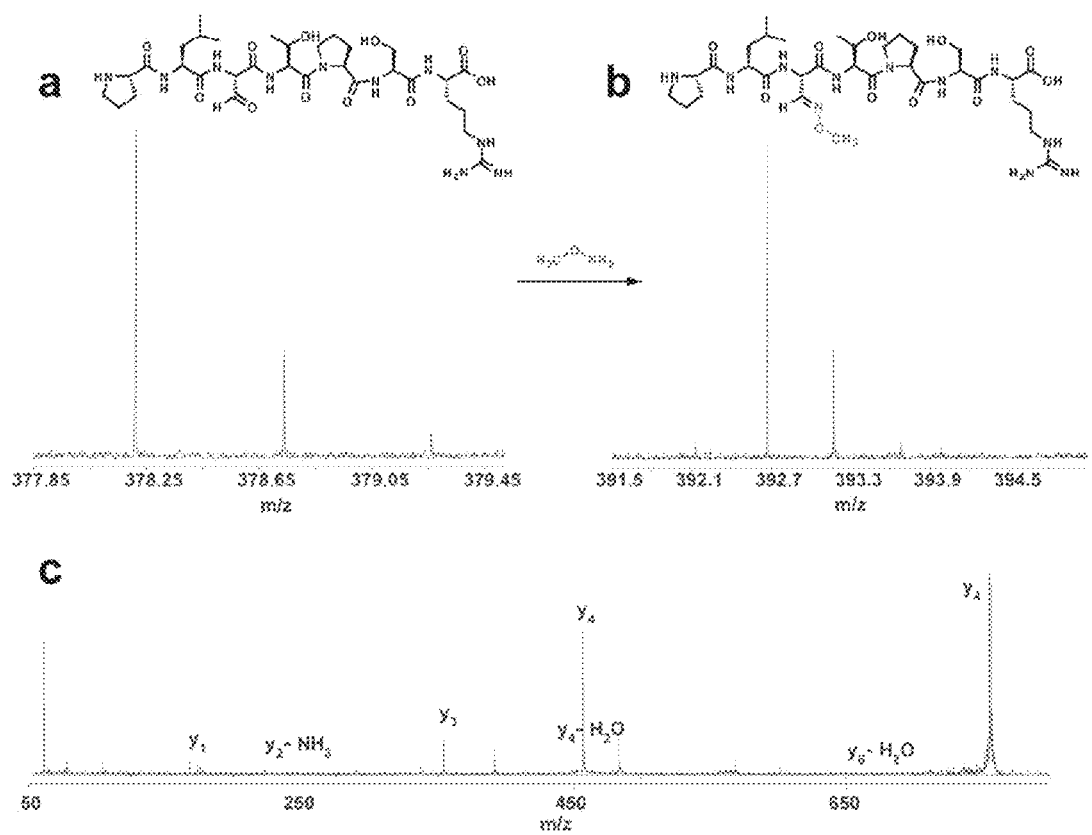
FIG. 2 is a set of graphs showing mass spectrum analysis confirming presence of FGly in a tryptic peptide from mycobacterial sulfotransferase with a 13 residue sulfatase consensus motif (ald13-Stf0). Mass spectra confirming the presence of FGly in a tryptic peptide from $ald_{13}$-Stf0. (Panel a) Mass spectrum of tryptic fragments incorporating FGly (M+2/2). Theoretical: 378.2066 m/z Observed: 378.2065. (Panel b) M+2/2 FT-ICR spectrum of tryptic fragment incorporating FGly after treatment with methoxylamine. Theoretical: 392.7198 m/z Observed: 392.7201. (Panel c) MALDI-TOF/TOF sequencing of the tryptic fragment incorporating FGly.

Tryptic digestion of the peptide containing the 13 residue sulfatase consensus motif (ald$_{13}$-Stf0) allowed direct mass spectral identification of FGly (FIG. 2). While the FGly-containing peptide could be easily identified, the cysteine containing peptide was not observed—indicating efficient oxidation of the aldehyde tag.

Example 2

Figure 3:
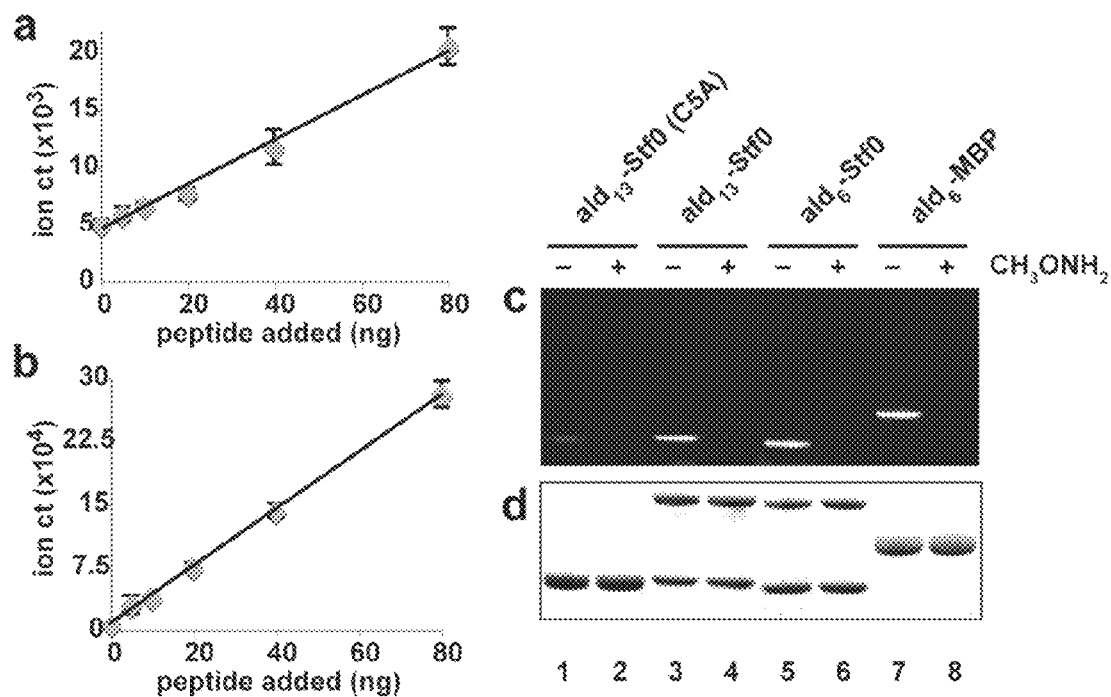
FIG. 3 illustrates results of quantitation of FGly production and selective fluorescent labeling of aldehyde tagged constructs. (Panel a) Standard addition of synthetic PL(FGly)TPSR (SEQ ID NO:92) to $ald_6$-Stf0 tryptic digest. (Panel b) Standard addition of synthetic PLCTPSR (SEQ ID NO:93) to $ald_6$-Stf0 tryptic digest. (Panel c) Selective fluorescent labeling of $ald_{13}$-Stf0, $ald_6$-Stf0 and $ald_6$-MBP with aminooxy-AlexaFluor 647 imaged directly on a fluorescent gel scanner. (Panel d) Protein loading was assessed by Sypro Ruby staining.

Peptides Containing the 6 Residue Sulfatase Consensus Motif Demonstrate High Rates of Conversion To quantify the extent of conversion from Cys to FGly, a standard addition assay was performed. The relative levels of cysteine and FGly within tryptically derived peptides from target proteins were compared to a standard addition curve, which was produced by doping synthetic peptides into tryptic digests at various concentrations (FIG. 3, panel a).

Unexpectedly, the Stf0 peptide containing the 6 residue sulfatase consensus motif (ald$_6$-Stf0), demonstrated slightly higher conversion than that of the Stf0 peptide containing the conserved 13 amino acid sequence (ald$_{13}$-Stf0), with conversion levels of 92±3% and 86±5%, respectively. This result is in contrast to previous sulfatase studies that indicated the distal threonine-glycine-arginine (TGR) sequence to be important for efficient cysteine oxidation (Dierks et al. (1999) EMBO J. 18(8):2084-91). The hGH peptide containing the 6 residue sulfatase consensus motif (ald$_6$-hGH) demonstrated significantly higher conversion at 99±5%.

Example 3

Conversion of Sulfatase Motifs by FGE is Independent of the Primary Sequence Context, Thus Allowing for Positioning of Aldehyde Tags at Either N-Terminal or C-Terminal Positions within a Polypeptide Previous sulfatase studies have indicated the distal threonine-glycine-arginine (TGR) sequence in the 13 residue sulfatase consensus motif (underlined below) to be important for high-level cysteine oxidation:

LCTPSRGSL<u>FTGR</u> (SEQ ID NO:55)

Because formation of FGly is thought to occur co-translationally (Dierks et al. Proc Natl Acad Sci USA. 1997 Oct. 28;

94(22):11963-8), it was reasoned that C-terminal constructs might experience lower FGly formation due to inaccessibility of the aldehyde tag. This was tested by generating a C-terminally tagged polypeptide containing maltose-binding protein and the 6 residue sulfatase consensus motif (ald$_6$-MBP):

LCTPSR-(maltose binding protein) (SEQ ID NO:1)

Surprisingly, the C-terminally tagged ald$_6$-MBP also demonstrated nearly quantitative conversion at 99±2%. Considering that the sulfatase motif is natively found within the interior of sulfatases, these results indicate that aldehyde formation is not limited with respect to the tag's primary sequence position.

Example 4

Selective Flourescent Labeling of Aldehyde Tagged Proteins

To demonstrate the specificity afforded by FGly introduction, a panel of aldehyde tagged proteins was labeled with ALEXA FLUOR® 647 aminooxyacetamide dye (Invitrogen):

ald$_{13}$-Stf0 (C5A): LATPSRGSLFTGR-(mycobacterial sulfotransferase)
(SEQ ID NO:56)
ald$_{13}$-Stf0: LCTPSRGSLFTGR-(mycobacterial sulfotransferase)
(SEQ ID NO:55)
ald$_6$-Stf0: LCTPSR-(mycobacterial sulfotransferase) (SEQ ID NO:1)
ald$_6$-MBP: LCTPSR-(maltose binding protein) (SEQ ID NO:1)

Aldehyde-tagged proteins demonstrated robust fluorophore labeling (FIG. 3, panel b): ald$_{13}$-Stf0 (−), ald$_6$-Stf0 (−), and ald$_6$-MBP (−)). In contrast, control proteins in which the critical cysteine in the aldehyde tag motif was mutated to alanine demonstrated only a small amount of background labeling (FIG. 3, panels c and d: ald$_{13}$-Stf0 (C5A) (−)). Aldehyde-tagged proteins incubated with an excess of methoxylamine, a competing nucleophile, demonstrated no labeling (FIG. 3, panels c and d, ald$_{13}$-Stf0 (C5A) (+), ald$_{13}$-Stf0 (+), ald$_6$-Stf0 (+), and ald$_6$-MBP (+)). Interestingly, although *E. coil*'s genome does not contain an annotated FGE, aldehyde-tagged protein expressed without exogenous FGE still demonstrated fluorescent labeling, albeit with lower intensity. This indicates that *E. coli* must natively express an enzyme or enzymes that are capable of oxidation of the sulfatase motif.

Example 5

Modification of an Aldehyde Tagged Proteins can Provide for "Switchable" Moieties Aldehydes readily react with hydrazide and aminooxy moieties to yield hydrazones and oximes, respectively. Although both of these conjugates are robust under physiological conditions, oximes are more thermodynamically stable. This difference can be exploited for switching the lower stability hydrazone conjugate to the more stable oxime conjugate. This feature of the aldehyde tag allows the modification of the target protein with two reagents in sequence (i.e., sequentially), as exemplified by conjugation of a purification tag followed by replacement of the conjugated purification tag to provide a conjugated fluorophore.

Figure 4:
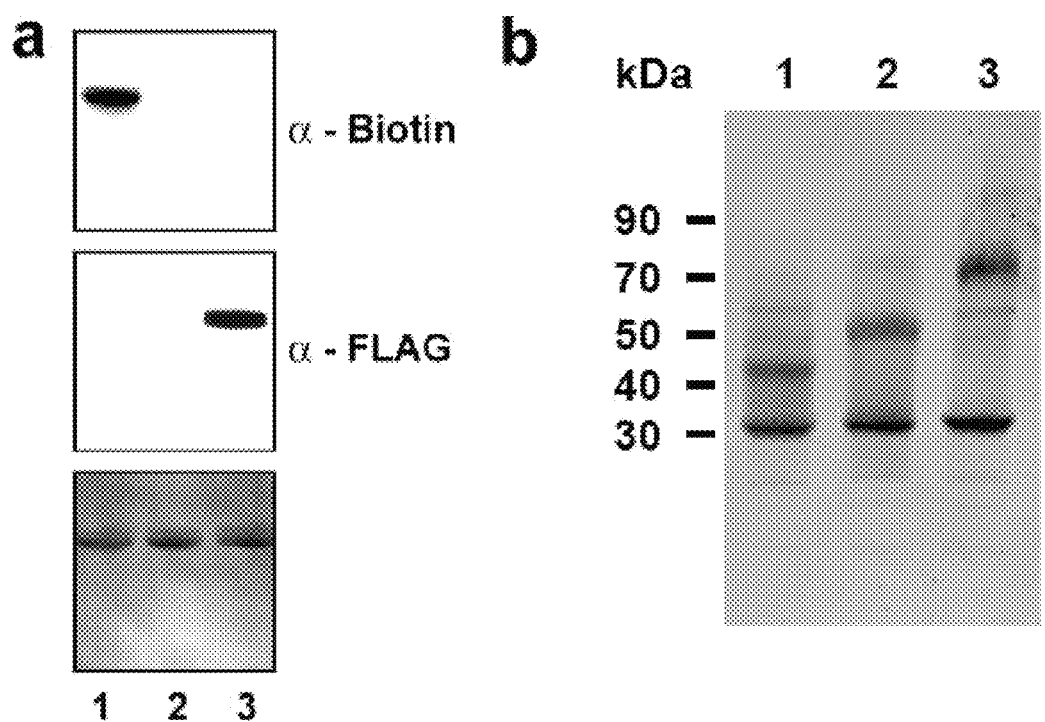
FIG. 4 is a set of images illustrating selective modification of aldehyde-tagged proteins. (Panel a) Switch assay of ald6-MBP. Lane 1: protein incubated with biotin hydrazide. Lane 2: protein incubated with biotin hydrazide and subsequently modified with methoxylamine. Lane 3: protein incubated with biotin hydrazide and subsequently modified with aminooxyFLAG. Protein loading (bottom box) was assessed by ponceau staining. (Panel b) PEGylation of ald6-Stf0 with 5,000 Da aminooxyPEG (lane 1), 10,000 Da aminooxyPEG (lane 2) and 20,000 Da aminooxyPEG (lane 3). Due to the PEG chains' lack of charge, the PEGylated proteins migrate slower than non-PEGylated proteins of similar molecular weight.

To assess the feasibility of this technique, a polypeptide containing maltose binding protein and the 6 residue sulfatase consensus motif (ald$_6$-MBP) was first labeled with biotin hydrazide and subsequently incubated with methoxylamine or an aminooxy epitope tag (aminooxy-FLAG). Labeling with biotin hydrazide led to a robust signal by α-biotin in a western blot (FIG. 4, panel a, lane 1). Subsequent incubation with methoxylamine or aminooxy-FLAG led to a complete loss of α-biotin signal (FIG. 4, panel a, lane 2) or a robust α-FLAG signal (FIG. 4, panel a, lane 3), respectively.

When the aminooxy-FLAG labeled protein was subsequently exposed to methoxylamine, only partial loss of signal was observed (data not shown), presumably due to the similar stabilities of the conjugates. These results indicate that sequential conjugation to an aldehyde-tagged protein can be programmed based on stability of the linkage chemistry.

Example 6

Creation of Site-Specific Pegylation to Produce PEG-Protein Conjugates in a Therapeutic Target Protein To illustrate the use of aldehyde tags in mediating site-specific PEGylation, aldehyde tags were used to site-specifically attach polyethylene glycol (PEG) chains to recombinantly expressed ald$_6$-Stf0. ald$_6$-Stf0 was recombinantly expressed and modified it with a series of aminooxy-PEGs with varying chain lengths. SDS-PAGE analysis of the Stf0-PEG conjugates demonstrated unambiguous mass shifts consistent with the molecular weight and charge of the appended PEG molecules (FIG. 4, Panel b). These results demonstrate the ease of obtaining site-specific PEG-protein conjugates regardless of the number of native cysteines or lysines.

The above provides proof of principle for application of aldehyde tags to mediate site-specific PEGylation of, for example, therapeutic proteins. PEGylation of pharmaceutical proteins is desirable as it can increase therapeutic index by increasing proteolytic stability and decreasing renal clearance. Additionally, PEGylation can be exploited to reduce immunogenicity of protein pharmaceuticals. Despite advances in protein conjugation chemistries, site-specific modification of proteins remains problematic. Derivatization of cysteine or lysine residues is currently the most utilized method to PEGylate proteins, but this non-specific labeling method results in PEGylation of multiple sites, creating an undesirable collection of discrete protein-PEG conjugates with different pharmacokinetics. The aldehyde tag technology described herein can be used to address needs such as these.

Example 7

Use of Aldehyde Tags to Modify Cell Surface Accessible Residues of a Polypeptide Expressed in Mammalian Cells To demonstrate the introduction of FGly into a protein integral to the cell membrane, an aldehyde-tagged synthetic photoisomerizable azobenzene-regulated K+ (SPARK) channel protein was produced. SPARK channel proteins, which are light-activated K+ ion channels, were developed for non-invasive control of neuronal activity (Banghart et al. Nat. Neurosci. 2004).

The 6 residue aldehyde tag described above (ald$_6$ (LCTPSR)) (SEQ ID NO:1) was introduced into a construct encoding a SPARK channel protein. Three strategies were used: 1) adding the 6 residue sulfatase consensus motif of the ald-tag within one of the protein's extracellular loops (referred to as "I" in FIG. 5); 2) deleting 6 residues from the loop and then replacing these residues with the 6 residue ald-tag (referred to as "C" in FIG. 5), and 3) deleting 3 residues from the loop and then adding the 6 residue ald-tag (referred to as "P" in FIG. 5). A vector-only negative control was also run ("V" in FIG. 5).

Plasmids encoding each of the three variants of the recombinant, aldehyde-tagged SPARK channel were transfected into Chinese hamster ovary (CHO) cells and into human embryonic kidney (HEK) cells. Both CHO and HEK cells express an endogenous FGE. However, in order to increase conversion of the Cys of the aldehyde tag, a plasmid encoding the aldehyde tagged SPARK was co-transfected with a pcDNA3.1 construct encoding human FGE. The human FGE used has the amino acid sequence:

```
                                        (SEQ ID NO: 57)
maapalglvc grcpelglvl lllllsllcg aagsqeagtg agagslagsc gcgtpqrpga hgssaaahry sreanapgpv pgerqlahsk mvpipagvft mgtddpqikq dgeaparrvt idafymdaye vsntefekfv nstgylteae kfgdsfvfeg mlseqvktni qqavaaapww lpvkganwrh pegpdstilh rpdhpvlhvs wndavayctw agkrlpteae weyscrgglh nrlfpwgnkl qpkgqhyani wqgefpvtnt gedgfqgtap vdafppngyg lynivgnawe wtsdwwtvhh sveetlnpkg ppsgkdrvkk ggsymchrsy cyryrcaars qntpdssasn lgfrcaadrl ptmd
```

After one day, the cells were lysed and the lysate was probed by Western blot for presence of a myc epitope (which is present in the SPARK channel protein, and thus demonstrates successful transfection and translation) and for the presence of the aldehyde by reaction with using aminooxy-FLAG, followed by probing with an anti-FLAG antibody. A ponceau blot demonstrated equal loading of samples from the same cell type on the blot.

Figure 5:
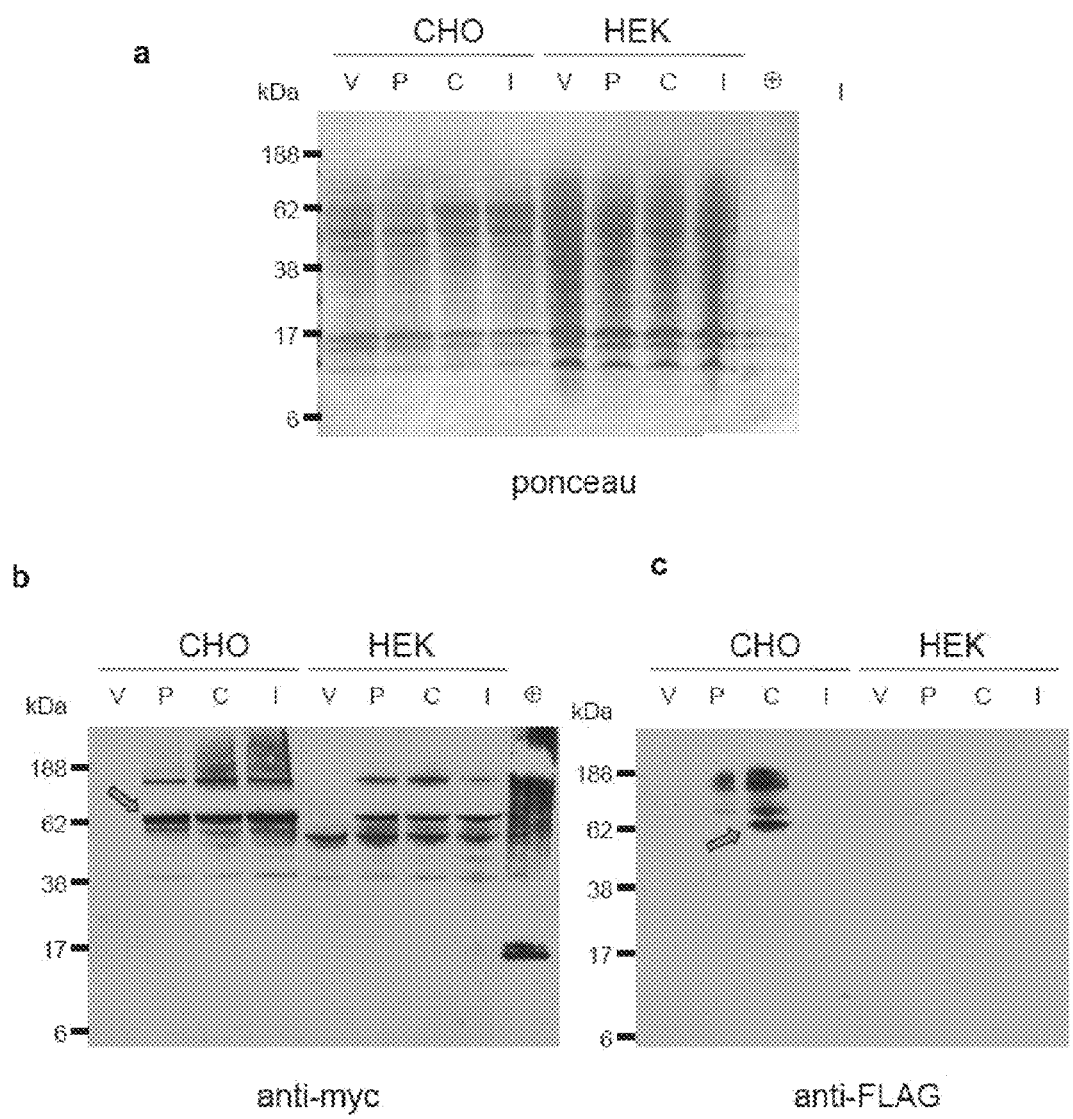
FIG. 5 is a set of gels images showing production of an ald-tagged synthetic photoisomerizable azobenzene-reguluted K+ (SPARK) channel protein in CHO (Chinese hamster ovary) and HEK (human embryonic kidney) cells. (Panel a) SDS-PAGE gel stained for protein using Ponceau S. (Panel b) Detection of binding of anti-myc antibody. (Panel c) Detection of binding of anti-FLAG antibody. V indicates the sample is a vector only negative control; P, C, and I represent three strategies for inserting an exemplary 6 residue ald-tag, namely adding the ald-tag within one of the extracellular loops (I), deletion of 6 residues from the loop and replacement with the ald-tag (C), or deleting 3 residues from the loop and then adding the 6 residue tag (P). (+) refers to a positive control sample, which is a CHO cell lysate containing a 17 kDa myc-tagged protein.

As shown in FIG. 5, the strategy involving deletion of 6 residues of the SPARK extracellular loop and replacement with the 6-residue ald-tag was successful (see the arrow on the anti-FLAG blot in FIG. 5, panel c). This result demonstrates the ability to modify cell surface residues of an aldehyde-tagged protein in mammalian cells.

The presence of the FLAG of the aldehyde tagged SPARK on the surface of the cell can be confirmed using flow cytometry.

Example 8

Use of Aldehyde Tags to Modify Fc Antibody Fragment

In order to further demonstrate applications of aldehyde tags, a soluble IgG Fc fragment was modified to contain an aldehyde tag at either the N- or C-terminus. Briefly, a 13-residue aldehyde tag ($ald_{13}$) (LCTPSRAALLTGR) (SEQ ID NO:58) was introduced so as to position the aldehyde tag at either the N-terminus of the C-terminus of the soluble IgG Fc fragment encoded in the commercially available pFuse-Fc vector (Invitrogen). In order to increase conversion of the Cys of the aldehyde tag, CHO cells were co-transfected with the Fc encoding construct and a pcDNA3.1 construct encoding human FGE.

Fc fragments were isolated from cell supernatant, and detection of the aldehyde-tagged IgG Fc fragment in which the Cys was converted to FGly was accomplished by reacting the isolated protein with an aminooxy-FLAG (DYKD-DDDK) (SEQ ID NO:59) probe (FLAG-$ONH_2$), followed by SDS-PAGE and Western-blot analysis. Proteins that were not reacted with the FLAG-$ONH_2$ probe served as an additional control.

Whereas Fc fusions containing the aldehyde tag 12mer gave robust labeling when present at either the N-terminus (N-Fc-Ald13) or C-terminus (C-Fc-Ald13), the control protein, in which the critical cysteine had been mutated to alanine (C to A mutation), gave no detectable signal (FIG. 17).

In order to assess whether a 6mer aldehyde tag is sufficient to mediate modification of a protein, IgG Fc fragments having a 6mer aldehyde tag (Fc-Ald) or a control tag (Fc-C→A) at the C-terminus were generated using the pFuse-Fc vector. Aldehyde tagged IgG Fc fragments were detected by reacting the isolated protein with an aminooxy-FLAG probe (FLAG-$ONH_2$), followed by SDS-PAGE and Western blot. Proteins that were not reacted with the FLAG-$ONH_2$ probe served as an additional control. As shown in FIG. 18, the 6mer aldehyde tag facilitated robust labeling of the Fc-Ald, while no detectable labeling was observed with Fc fragments modified to include the control tag. Constructs encoding IgG Fc fragments having the 6mer aldehyde tag position at the N-terminus yielded similar results (data not shown).

In order to confirm formylglycine (FGly) modification of the Fc fragments, N- or C-terminally tagged ald13-Fc fragments were subjected to tryptic digestion to allow for direct mass spectral identification of FGly. As shown in FIGS. 19 and 20, the FGly-containing peptide and the cysteine containing peptide could be easily identified from both N-terminally and C-terminally modified Fc fragments.

Specific labeling of the aldehyde-tagged Fc was also realized by subjecting the serum-free medium directly to the aminooxy-FLAG probe (data not shown).

Example 9

Efficiency of Conversion of Cys To FGly in Aldehyde Tagged Proteins

In order to quantify the extent of conversion from Cys to FGly, an assay was developed to analyze conversion efficiency of trypsin-digested target proteins. The quantity of the unmodified peptide containing cysteine was determined from a standard curve, which was produced by doping synthetic peptides into tryptic digests at various concentrations. The quantity of the FGly-containing peptide was calculated by subtracting the quantity of the cysteine-containing peptide from the total protein quantity, determined using BCA protein assay.

When this assay was applied to the N- and C-terminally tagged Fc fragment described in the Example above, it was found that in the presence of exogenous human FGE (hFGE) the efficiency of conversion from Cys to FGly was 86±1% for the N-terminally tagged ald13-Fc and 58±2% for C-terminally tagged Fc-ald13. In contrast, in the absence of exogenous hFGE, the efficiency of conversion was only about 25% and about 23% for N- and C-terminally tagged Fc fragment, respectively. C-terminally modified Fc fragment containing a 6mer aldehyde tag exhibited a conversion efficiency of about 92% in the presence of exogenous hFGE.

Example 10

Aldehyde Tag-Mediated Modification of Cell Surface Proteins

This example demonstrates that aldehyde tags can be used to facilitate site-specific modification of cell surface proteins, the platelet derived growth factor receptor (PDGFR) transmembrane domain (encoded by pDisplay vector from Invitrogen), in live HEK cells using the same approach.

The 13mer aldehyde tag (LCTPSRAALLTGR) (SEQ ID NO:58) or a control tag (LATPSRAALLTGR) (SEQ ID NO:60) was introduced into a pDisplay™ expression construct (Invitrogen; FIG. 21) between Bgl II and Sal I Sites. The resulting fusion proteins are referred to here as Ald13-TM (containing the 13mer aldehyde tag) and C→A-TM (containing the control tag). This expression construct and a construed expressing human FGE (hFGE) were transiently transfected into HEK293-T cells to provide for expression.

Labeling of cells was accomplished by reacting with an oxyamino biotin and probed by streptavidin Alex fluro 488 conjugates. The cells were then subjected to analysis by flow cytometry.

As illustrated in FIG. 21, the mean fluorescence of cells expressing the Ald13-TM surface protein was significantly higher (mean fluorescence about 24.42) than cells expressing the C→A-TM control (mean fluorescence about 3.31).

Example 11

Aldehyde Tag Modification for Labeling of Cytosolic Protein

To illustrate the use of the aldehyde tag in specific labeling of cytosolic proteins, constructs encoding aldehyde tagged or control tagged green fluorescent protein derived from *Aequorea coerulescens* (AcGFP) were generated. Using the commercially available pAcGFP1-N1 vector (Clontech), an expression construct encoding an AcGFP fusion protein composed of a His tag (six histidine residues, represented by $His_6$) followed by 13mer aldehyde tag (LCTPSRAALLTGR) (SEQ ID NO:58) or a control tag (LATPSRAALLTGR) (SEQ ID NO:60) positioned at the N terminus of AcGFP was generated by insertion of the His tag and 13mer aldehyde tag coding sequences between the Kpn I and Xma I restriction sites.

A bacterial FGE homolog derived from *Streptomyces coelicolor* (StrepFGE) was cloned into a mammalian expression vector (pcDNA 3.1, Invitrogen) for cotransfection of HEK cells with a plasmid encoding aldehyde tagged GFP (Ald-AcGFP) or control tagged GFP (C→A-AcGFP). Cells lacking expression of StrepFGE were used as a further control.

Detection of the aldehyde-tagged AcGFP that contained FGly was accomplished by reacting the isolated protein with an aminooxy-FLAG (DYKDDDDK) (SEQ ID NO:59) probe (FLAG-ONH2), followed by SDS-PAGE and Western-blot analysis. Proteins that were not reacted with the FLAG-ONH$_2$ probe served as an additional control.

In the presence of the cytosolic FGE homolog, the cysteine residue within the consensus sequence was efficiently converted to a formylglycine (FGly) (FIG. 22), while control tagged AcGFP did not exhibit detectable labeling indicating no detectable FGly. In addition, Ald-GFP produced in HEK cells that did not express StrepFGE also produced a strong signal (FIG. 22). This may be due to the method of protein isolation used in which the HEK cells are lysed, and thus may free the hFGE from the ER of these cells, thus allowing for contact between the hFGE and the aldehyde tag resulting in cysteine conversion to the aldehyde.

Example 12

Aldehyde Tag Modification of IFN-Beta

Aldehyde tags can be used to facilitate modification of a variety of proteins. Exemplary proteins of interest for modification include interferon beta (IFN-beta). IFN-beta is composed of five alpha-helices (A-E) with a single glycosylation site existing at residue Asn-80. IFN-beta can be modified to provide for modification at the glycosylation site and/or at other solvent accessible sites of the protein. For example, the amino acid sequence of IFN-beta that facilitates glycosylation can be modified so as to provide an aldehyde tag. For example, using recombinant techniques, the IFN-beta sequence DSSSTGWNE (SEQ ID NO:61) present in a loop of IFN-beta can be replaced with the aldehyde tag-containing sequence GSLCTPSRG (SEQ ID NO:62). The aldehyde tag can then be exploited to attach a moiety of interest, as exemplified in FIG. 23.

Examples 13-14

Identification and Characterization of an FGE from *M. Tuberculosis*

Figure 7:
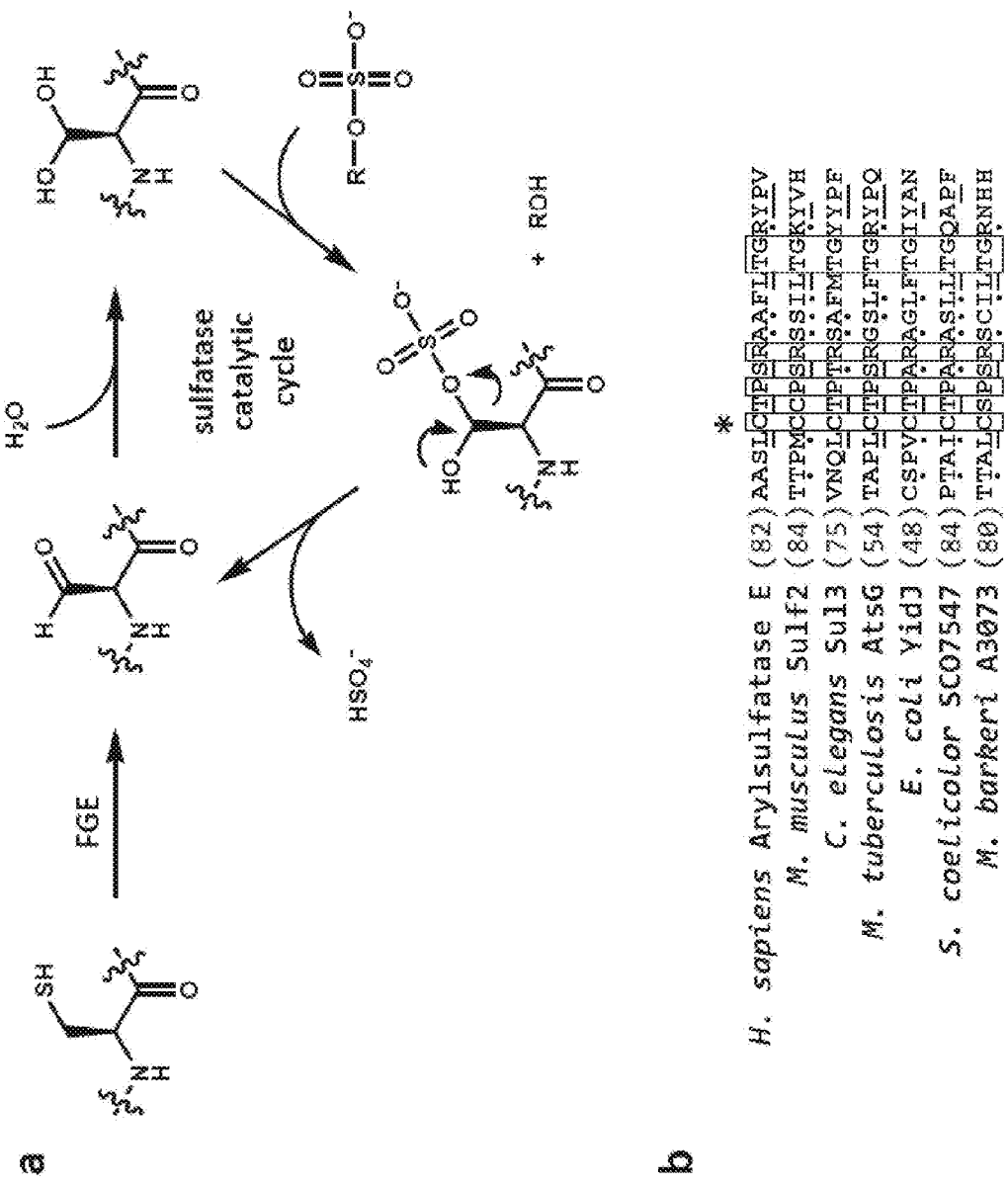
FIG. 7 illustrates activation of sulfatases by formylglycine generating enzyme (FGE) and proposed sulfatase mechanism. (Panel a) FGE activates sulfatases by oxidizing an active site cysteine to a 2-formylglycyl residue (FGly). Previously determined sulfatase crystal structures indicate that the active site FGly is hydrated, suggesting that sulfate ester cleavage is mediated by a transesterification-elimination mechanism$_6$. (Panel b) The sulfatase motif is located towards the N-terminus of sulfatases and targets the appropriate cysteine (*) for modification by FGE. Boxed residues indicate an exact residue match; underlined residues indicates conserved residues; residues with a dot (•) indicates similar residues. From top to bottom; SEQ NO:85, SEQ ID NO:86, SEQ NO:87, SEQ ID NO:88, SEQ NO:89, SEQ ID NO:90, SEQ NO:91, and SEQ ID NO:55.
Figure 8:
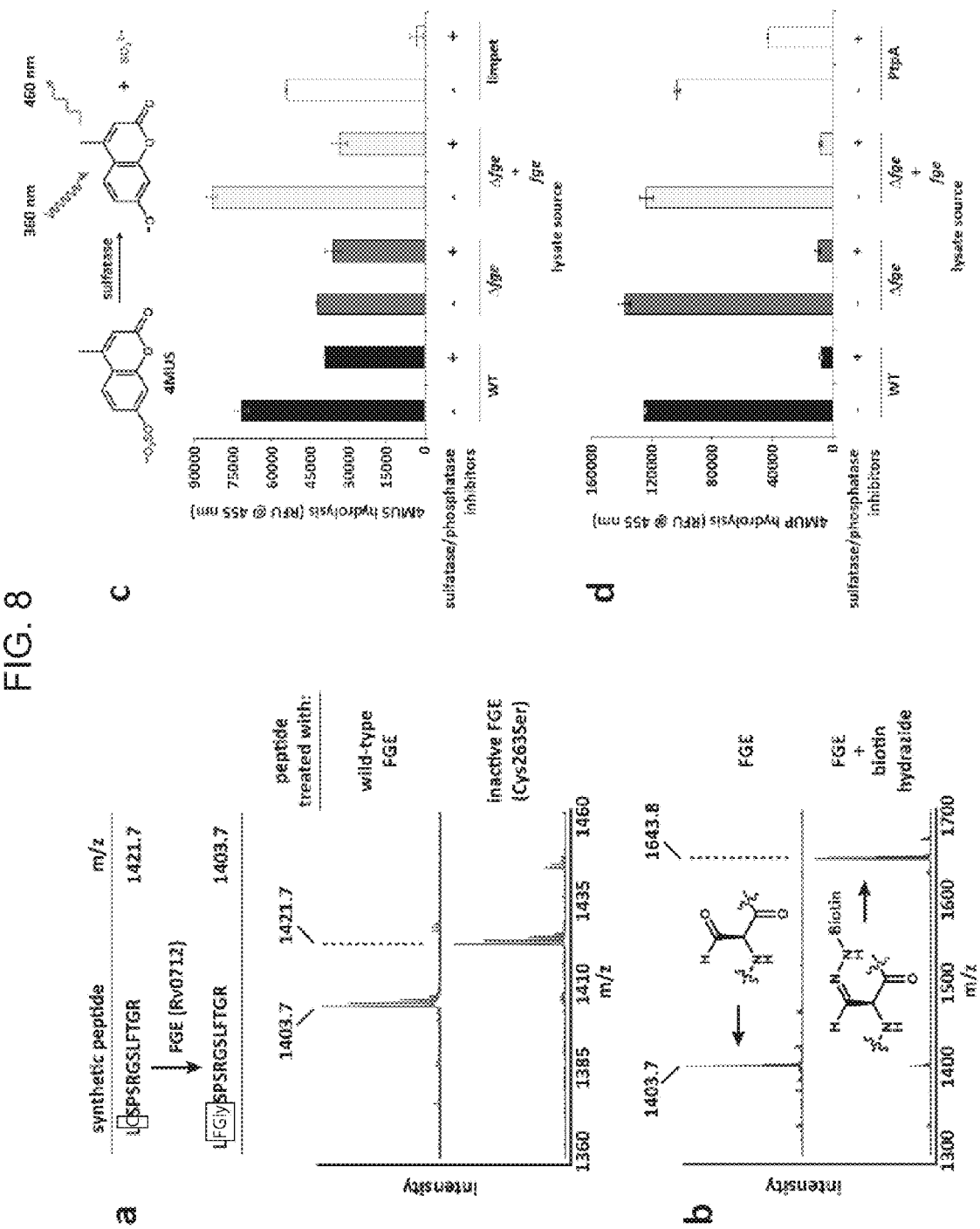
FIG. 8 provides results showing function of Mtb FGE (Rv0712) in vitro and in vivo. (Panel a) A synthetic peptide resembling a sulfatase motif was treated with recombinant Mtb FGE and the resulting oxidation of cysteine to FGly was monitored by mass spectrometry. The Cys263Ser FGE mutant was inactive on the peptide substrate. The ions at m/z 1427 and 1445 are sodium adducts of the modified and unmodified peptide, respectively. (Top to bottom; SEQ ID NO: 84, SEQ ID NO:94) (Panel b) Upon treatment with biotin hydrazide, the FGly-containing peptide forms a hydrazone adduct with biotin, resulting in a mass shift of +240 Da. (Panel c) Lysates from wild-type (WT), Δfge, and complemented (Δfge+fge) strains of Mtb H37Rv were tested for sulfatase activity using the fluorogenic substrate 4-methylumbelliferyl sulfate (4MUS) with and without sulfatase/phosphatase inhibitors. Limpet sulfatase was used as a positive control. (Panel d) Lysates from WT, Δfge, and Δfge+fge strains of Mtb H37Rv were tested for phosphatase activity using the fluorogenic substrate 4-methylumbelliferyl phosphate with and without sulfatase/phosphatase inhibitors. The recombinant Mtb phosphatase PtpA was used as a positive control.
Figure 9:
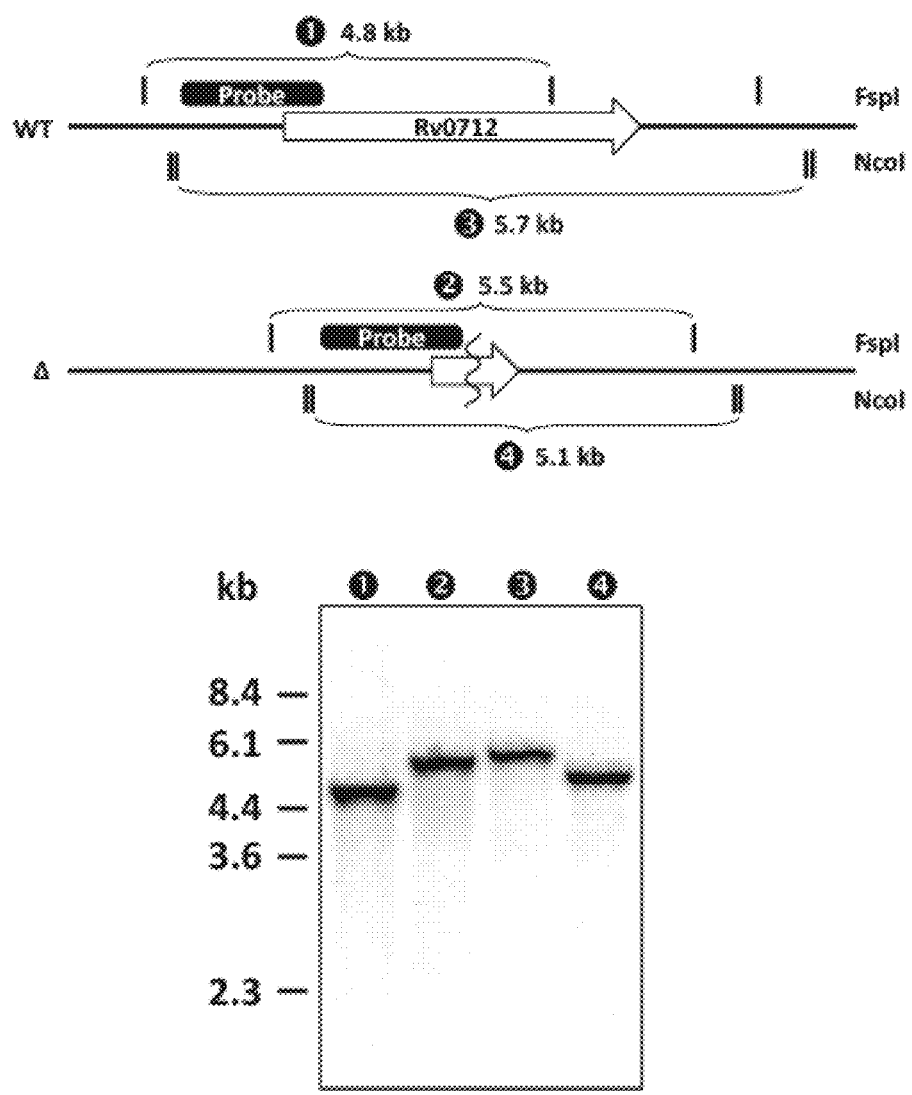
FIG. 9 provides results of Southern blot analysis of Mtb Δfge mutant. Genomic DNA was digested with FspI or NcoI, separated by agarose gel electrophoresis, and transferred to a nylon blot. The blot was probed with a 474 bp digoxigenin-labeled DNA fragment, identifying a 4.8 kb FspI fragment and 5.7 kb NcoI fragment for wild-type and 5.5 kb FspI fragment and 5.1 kb NcoI fragment for the mutant.

In the following Examples, a prokaryotic FGE is functionally identified in *Mycobacterium tuberculosis* (Mtb). As discussed above, sulfatases are members of an expanding family of enzymes that employ novel co- or post-translationally derived cofactors to facilitate catalysis, and contain an active site FGly residue. The FGly residue is thought to undergo hydration to the gem-diol, after which one of the hydroxyl groups acts as a catalytic nucleophile to initiate sulfate ester cleavage (FIG. 7, Panel a). The FGly residue is located within a sulfatase consensus sequence, which defines the sulfatase family of enzymes and is highly conserved throughout all domains of life (FIG. 7, Panel b). Whereas FGly is formed from cysteine residues in eukaryotic sulfatases, either cysteine (within the core motif CXPXR) or serine (SXPXR) can be oxidized to FGly in prokaryotic sulfatases. Some prokaryotes, such as Mtb, encode only cysteine-type sulfatases, whereas other species have only serine-type sulfatases or a combination of both.

Examples 8-9 describe characterization of a prokaryotic FGE from Mtb and solved the structure of the ortholog from Strep. Our studies indicate that FGE-activated sulfatases account for approximately half of the total sulfatase activity in Mtb lysate, suggesting that this organism possesses FGE-independent sulfatases that have yet to be identified. Defining the complete repertoire of sulfatases from Mtb (and other prokaryotes) is an important future goal and will provide the platform for defining these enzymes' role in the organism's lifecycle and pathogenesis.

Methods and Materials

The following methods and materials were used in the Examples relating to identification of an FGE in *Mycobacterium tuberculosis* (Mtb), and production of an FGE-deficient Mtb strain.

Preparation of Protein Expression Vectors.

The table below lists the oligonucleotides used in the examples below. The gene encoding Mtb FGE (Rv0712, encoding residues 2-299) was amplified from Mtb H37Rv genomic DNA and cloned into pET14b Novagen) using NdeI and XhoI restriction sites. The gene encoding Strep FGE (SCO7548, encoding residues 2-314) was amplified from Strep A3(2) genomic DNA and cloned into pET151/D-TOPO (Invitrogen). Open reading frames Rv2407 (encoding residues 2-273), Rv3406 (encoding residues 2-295), and Rv3762c (encoding residues 2-626) were amplified from Mtb H37Rv genomic DNA. Rv2407 was ligated into pMAL-C2X (New England Biolabs) using BamHI and PstI restriction sites, and both Rv3406 and Rv3762c were ligated into pET28b (Novagen) using NdeI and XhoI restriction sites. DNA sequencing was performed to confirm the fidelity of each gene product. Protein-encoding plasmids were transformed into BL21(DE3) cells (Invitrogen).

Site Directed Mutagenesis.

Site-specific mutations in Mtb FGE and Strep FGE were produced using QuikChange PCR mutagenesis kit (Stratagene). pET14b Mtb FGE and pET151 Strep FGE plasmids and the appropriate oligonucleotides from the table above were used in the mutagenesis reactions. Mutations were confirmed by DNA sequencing and plasmids were transformed into BL21(DE3) cells for protein expression as described below.

Protein Expression and Purification.

Clonal populations of BL21(DE3) cells harboring a $His_6$-tagged protein-encoding plasmid were incubated in LB media with ampicillin or kanamycin with shaking at 37° C. until $OD_{600}=0.5$, at which time the temperature was lowered

| Oligonucleotide primers | |
|---|---|
| Primer | Sequence (5' -> 3') |
| Mtb fge Start | CTATGCTACATATGCTGACCGAGTTGGTTGACCTGC (SEQ ID NO: 63). |
| Mtb fge End | TAGCATAGCTCGAGCTACCCGGACACCGGGTCG (SEQ ID NO: 64). |
| Strep fge Start | CACCGCCGTGGCCGCCCCGTCCCC (SEQ ID NO: 65). |
| Strep fge End | TCACTCAGCGGCTGATCCGG (SEQ ID NO: 66). |
| Mtb Rv2407 Start | CTATGCTAGGATCCCTTGAGATCACGTTGCTCGG (SEQ ID NO: 67). |
| Mtb Rv2407 End | CTATGCTACTGCAGCTAGCGCCGCGGGTGCACCTC (SEQ ID NO: 68). |
| Mtb Rv3406 Start | CTATGCTACATATGACAGATCTGATTACCGTGAAG (SEQ ID NO: 69). |
| Mtb Rv3406 End | CTATGCTACTCGAGTCAGCCAGCGATCTCCATCG (SEQ ID NO: 70). |
| Mtb Rv3762c Start | CTATGCTACATATGCCGATGGAACACAAACCTCC (SEQ ID NO: 71). |
| Mtb Rv3762c End | CTATGCTACTCGAGCTACGGCGTCACGATGTTGAAG (SEQ ID NO: 72). |
| Mtb fge Ser260Ala[a] | GACCCTCAAGGGCGGCGCACACCTGTGCGCGCCG (SEQ ID NO: 73). |
| Mtb fge Cys263Ser[a] | TCGCACCTGAGCGCGCCGGAGTACTGC (SEQ ID NO: 74). |
| Mtb fge Cys268Ser[a] | GCGCCGGAGTACAGCCACCGCTACCGC (SEQ ID NO: 75). |
| Strep fge Trp234Ala[a] | CACCGCGGGCAACGTGGCGGAATGGTGCTCCGAC (SEQ ID NO: 76). |
| Strep fge Trp234Phe[a] | CACCGCGGGCAACGTGTTTGAATGGTGCTCCGAC (SEQ ID NO: 77). |
| Strep fge Cys272Ser[a] | GGCGGCTCCTACCTGTCCCACGACTCCTACTGC (SEQ ID NO: 78). |
| Strep fge Cys277Ser[a] | GTGCCACGACTCCTACTCCAACCGCTACCGGGTCG (SEQ ID NO: 79). |
| Mtb Δfge upstream 5' | CTATGCTAAAGCTTGAATCGAGTGAGATATTGCC (SEQ ID NO: 80). |
| Mtb Δfge upstream 3' | TAGCATAGTCTAGAATGACGCTCGATCGAGAACG (SEQ ID NO: 81). |
| Mtb Δfge downstream 5' | CTATGCTATCTAGATCCTCACAGTCGCAGGACAGC (SEQ ID NO: 82). |
| Mtb Δfge downstream 3' | TAGCATAGTTAATTAATGCACCATCTCGTTGCTCTCG (SEQ ID NO: 83). |

[a]Numbered from the beginning of the respective FGE start codon. A pair of complementary primers was used for each mutant. Reverse complements are not shown; changes to the sequence are underlined.

to 18° C. and 250 μM IPTG was added. After 12-16 h, cells were harvested and resuspended in 20 ml of lysis buffer (50 mM Tris, 500 mM NaCl, 10% glycerol, 20 mM imidazole, 1 mM DTT, 1 mM TCEP, 1 mM methionine, pH 7.5) per liter of culture and lysed by sonication. Cell lysate was treated with DNase (10 μg/ml), cleared by centrifugation and applied to a 1 ml HisTrap column (GE Healthcare). The column was washed with lysis buffer with 35 mM imidazole and $His_6$-tagged protein was eluted using lysis buffer with 250 mM imidazole. The elution volume was concentrated to less than 2 ml if necessary and further purified on a Sephadex 16/60 S300 column (GE Healthcare). Purified recombinant protein was subsequently concentrated to about 20 mg/ml.

The identity and purity of Mtb and Strep FGE was assessed by electrospray ionization mass spectrometry (Bruker/Agilent Esquire). Rv2407 was not soluble in $His_6$-tagged form and was alternatively fused to maltose binding protein (MBP). Growth and lysis conditions for MBP-Rv2407 producing cells were the same as above except with the absence of imidazole in the lysis buffer. Cleared lysate was applied to amylose resin (New England Biolabs) in lysis buffer, washed in additional lysis buffer, and MBP-Rv2407 was eluted in lysis buffer with 10 mM maltose and subsequently concentrated. MBP was cleaved and removed from Rv2407 using Factor Xa (New England Biolabs) and amylose resin, respectively.

Strep FGE Crystallization.

Attempts to crystallize FGE homologs from Mtb, *Mycobacterium smegmatis* and *Mycobacterium avium* were not successful due to protein instability. Strep FGE was dialyzed into 10 mM Tris pH 7.5, 150 mM NaCl, and 1 mM TCEP. Crystals of $His_6$-tagged Strep FGE were obtained using vapor diffusion by mixing 1 μl of dialyzed protein with 1 μl of crystallization solution (100 mM Tris pH 8.0, 2.4 M ammonium formate, 0.3% β-octylglucoside, 3.2% 2-butanol) at room temperature (RT). Crystals grew over a period of two weeks and were subsequently transferred to cryoprotectant consisting of crystallization solution with 20% glycerol.

Strep FGE Structure Determination.

Data were collected at beamline 8.2.2 at the Advanced Light Source using an ADSC Quantum-Q315 CCD detector. Diffraction data were processed using HKL2000 (Otwinowski et al. (1997) Methods Enzymol: Macromol Crystallogr Part A 276, 307-326) Initial phases were determined by molecular replacement using the human FGE (PDB entry 1Y1E) as a search model in PHASER (Storoni et al. (2004) Acta Crystallogr D Biol Crystallogr 60, 432-8). The asymmetric unit contained five Strep FGE monomers in space group $P3_12_1$. Initial stages of model refinement included cycles of simulated annealing with torsion angle dynamics and restrained B-factor refinement using CNS (Brunger et al. (1998) Acta Crystallogr D Biol Crystallogr 54, 905-21), followed by manual model rebuilding using O (Jones et al. (1991) Acta Crystallogr A 47 (Pt 2), 110-9). The final cycles of refinement were carried out with TLS (Winn et al. (2001) Acta Crystallogr D Biol Crystallogr 57, 122-33) restraints as implemented in REFMAC5 (Murshudov (1997) Acta Crystallogr D Biol Crystallogr 53, 240-55) using 5 TLS groups (corresponding to each FGE monomer in the asymmetric unit). Water molecules were added with ARP/WARP (Lamzin et al. (1993) Acta Crystallogr D Biol Crystallogr 49, 129-47). The final model contained residues 18-305 in monomer A, residues 19-306 in monomer B, residues 20-306 in monomer C, residues 19-305 in monomer D, and residues 19-307 in monomer E. Final $R_{work}$ and $R_{free}$ values were 19.5% and 23.3%, respectively. Data collection and processing statistics are summarized in the table below. All figures were generated with PyMOL (www.pymol.org).

| Data collection | |
|---|---|
| Resolution (Å)[a] | 20-2.1 (2.1-2.17) |
| Wavelength (eV) | 12,398.4 |
| Space group | P3121 |
| Unit cell dimensions (a = b, c) (Å) | 142.444, 217.067 |
| Measured reflections | 123276 |
| Completeness (%) | 83.4 (88.2) |
| Redundancy | 2.6 (2.6) |
| Mosaicity (°) | 0.32 |
| I/σ | 15.8 (1.9) |
| Rsym (%)b | 5.7 (23.3) |
| Refinement | |
| Rwork (%)c | 19.5 |
| Rfree (%)c | 23.3 |
| Number of residues/waters | 1438/1017 |
| Rms bonds (Å)/angles (°) | 0.008/1.062 |
| Ramachandran plot (%)d | 87.9/11.2/0.5/0.6e |
| Average B values | 41.5 |

[a]Values in parentheses correspond to the highest resolution bin.
bRsym = 100 * ΣhΣi|Ii(h) − <I(h)>|/ΣhΣiIi(h), where Ii(h) is the ith, measurement of reflection h and <I(h)> is the average value of the reflection intensity.
cRwork = 100 * Σ||Fobs| − |Fcalc||/|Fobs|, where Fobs and Fcalc are the structure factor amplitudes from the data and the model, respectively. Rfree is Rwork with 5% of the reflections set aside throughout refinement.
dNumbers correspond to the percentage of amino acid residues in the favored, allowed, generously allowed and disallowed regions, respectively. Calculated using PROCHECK39.
eSeven residues were observed in stereochemically strained conformations either due to crystal packing contacts (Tyr219 in monomers A and C) or hydrogen bonding interactions (Asn232 in monomers A-E).

FGE Activity Assay.

Wild-type and mutant FGE from Mtb and Strep were purified as described above. The peptide substrate was synthesized by standard Fmoc solid-phase synthesis methods and consisted of the 13-residue sequence LCSPSRGSLFTGR (SEQ ID NO:84), a sulfatase consensus motif. The N-terminus was acetylated, the C-terminus was amidated and the sequence was confirmed by mass spectrometry. Assay conditions were similar to those reported previously by Dierks et al. in studies of human FGE (Dierks et al. (2003) Cell 113, 435-4). Anaerobic experiments were performed in the same manner except solutions were made anaerobic using an oxygen-scavenged gas manifold and reactions were started by mixing enzyme with substrate in an anaerobic glovebox. EDTA was added to the appropriate reactions at a concentration of 100 mM. Confirmation of FGly formation was performed by incubating 1 μl of desalted product with 1 μl of 5 mM biotin hydrazide (Sigma) for 30 min at RT. Samples were mixed 1:1 (v/v) with matrix solution (10 mg/ml α-cyano-4-hydroxy-cinnamic acid with 2 mM ammonium citrate) and analyzed by matrix-assisted laser desorption/ionization-time of flight mass spectrometry (Applied Biosystems Voyager DE Pro).

Metal Detection.

A multi-element standard solution was prepared by appropriate dilution of ICP standards of Ca, Cu, Fe, Mn, Mg, and Zn (Sigma). Metal content of Mtb and Strep FGE were analyzed by ICP-AES using a Perkin Elmer Optima 3000 DV. Absence of Fe, Cu and Zn in Strep FGE was confirmed at beamline 8.3.1 at the Advanced Light Source. Absorption edges of these metals were examined using a double crystal monochrometer and the beamline's x-ray fluorescence detector.

Mtb FGE-Deficient Strain Production.

Figure 10:
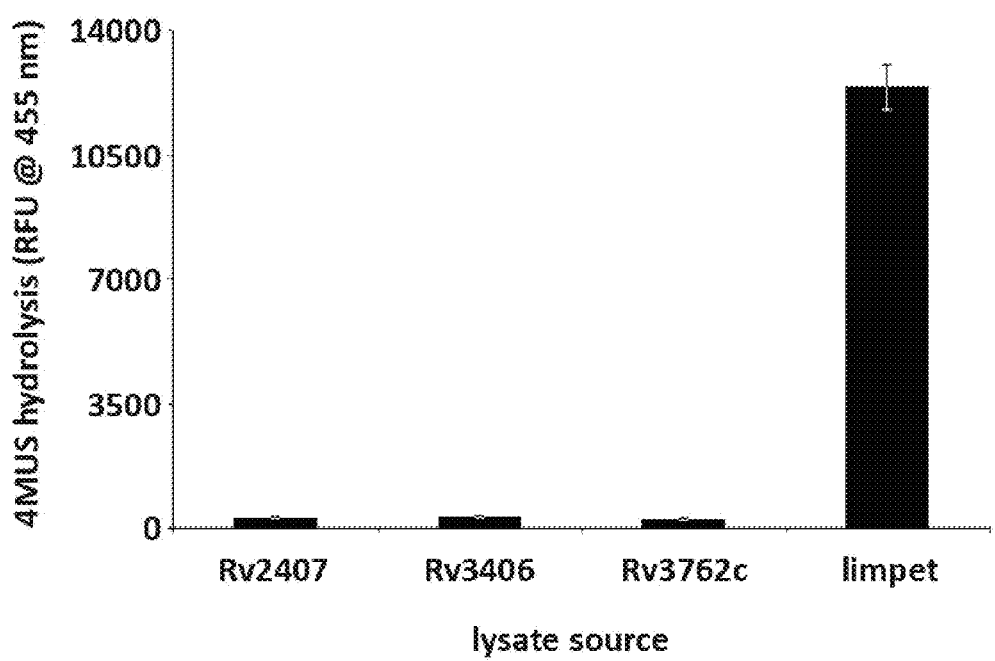
FIG. 10 shows data illustrating that recombinant Rv2407, Rv3406 and Rv3762c do not exhibit activity in the 4MUS assay. Limpet sulfatase was used as a positive control.
Figure 11A:
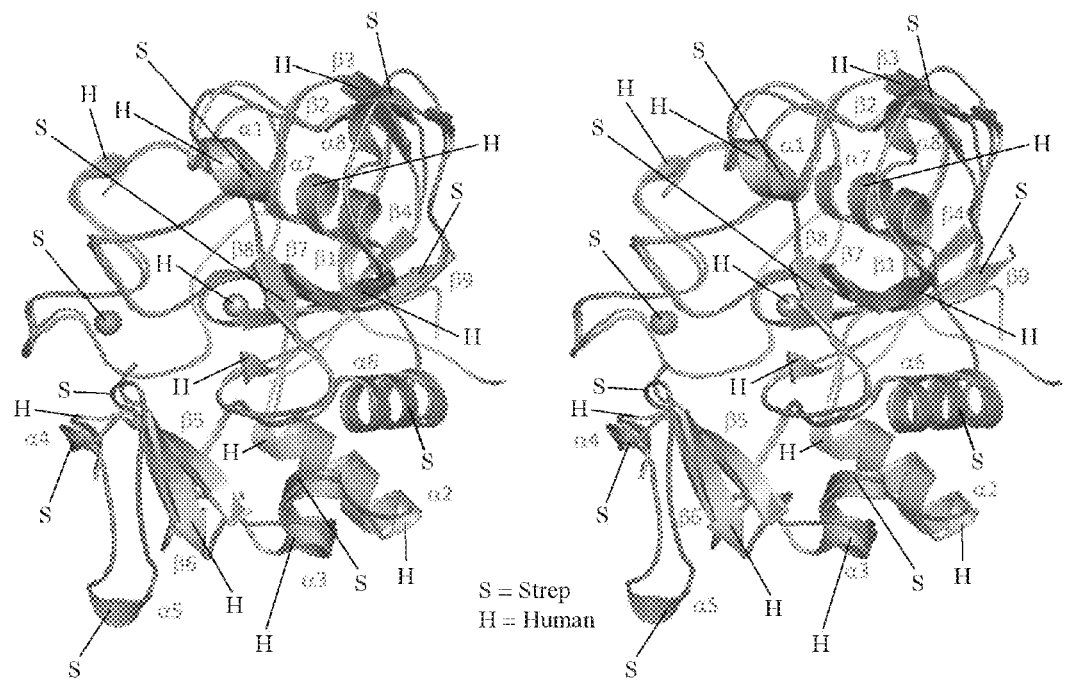
FIGS. 11A-E are schematics showing the structure of Strep FGE.
Figure 11B:
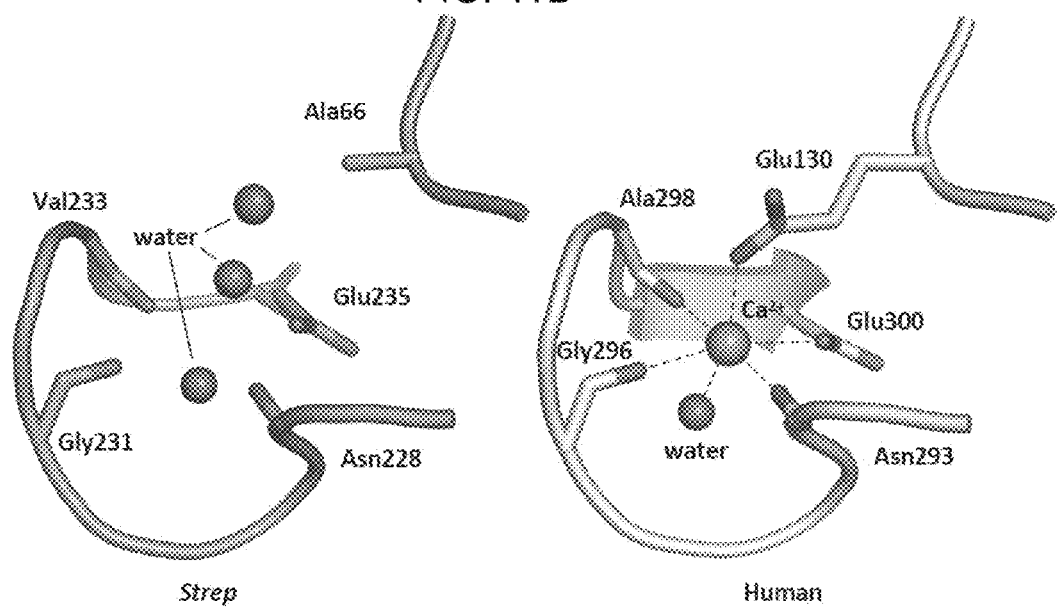
Figure 11C:
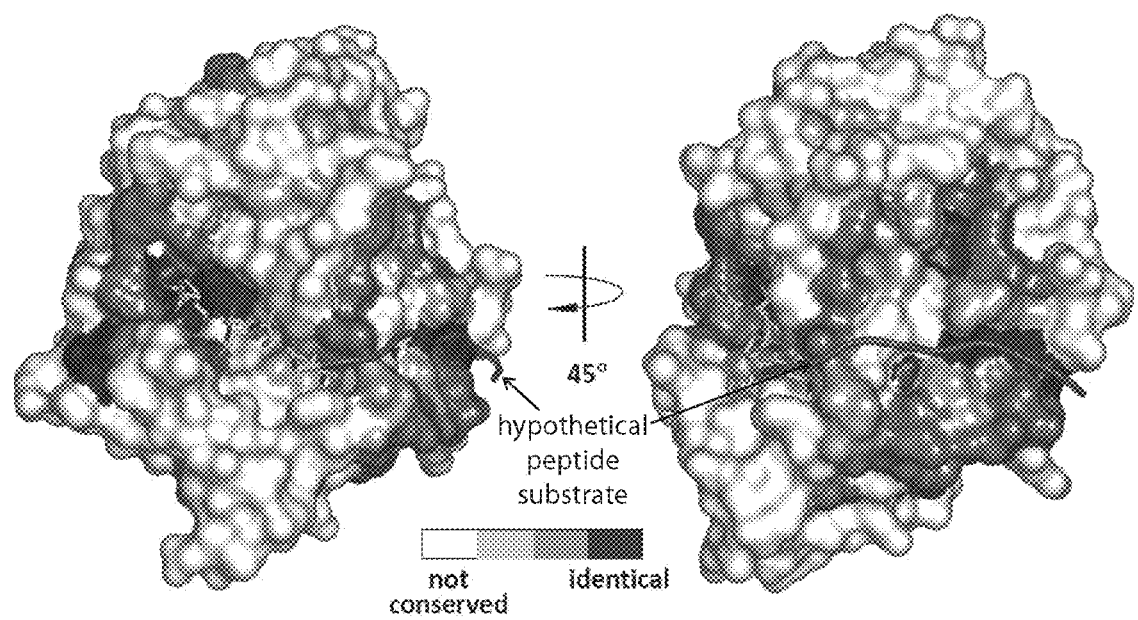
Figure 11D:
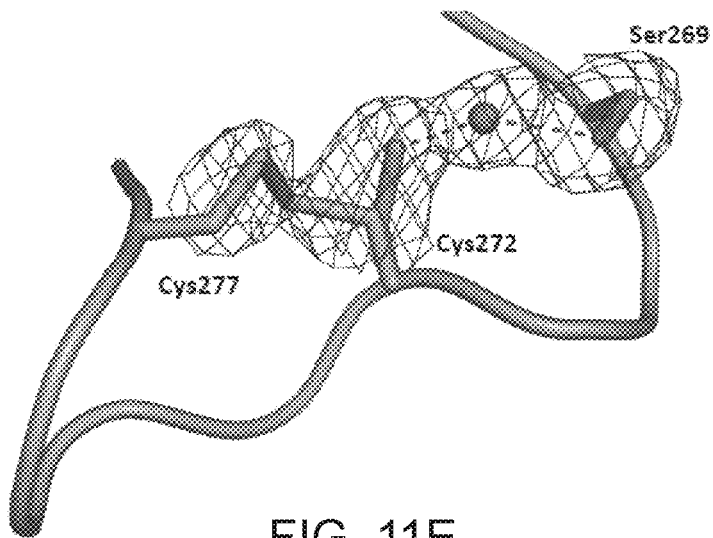
Figure 11E:
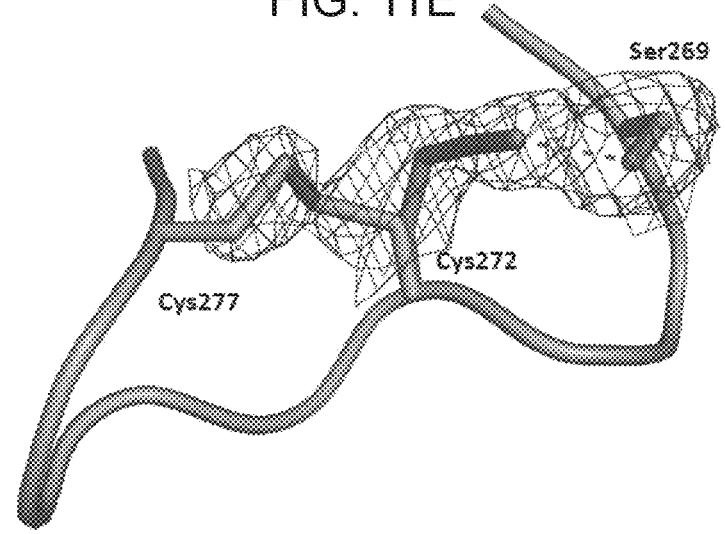
Figure 13:
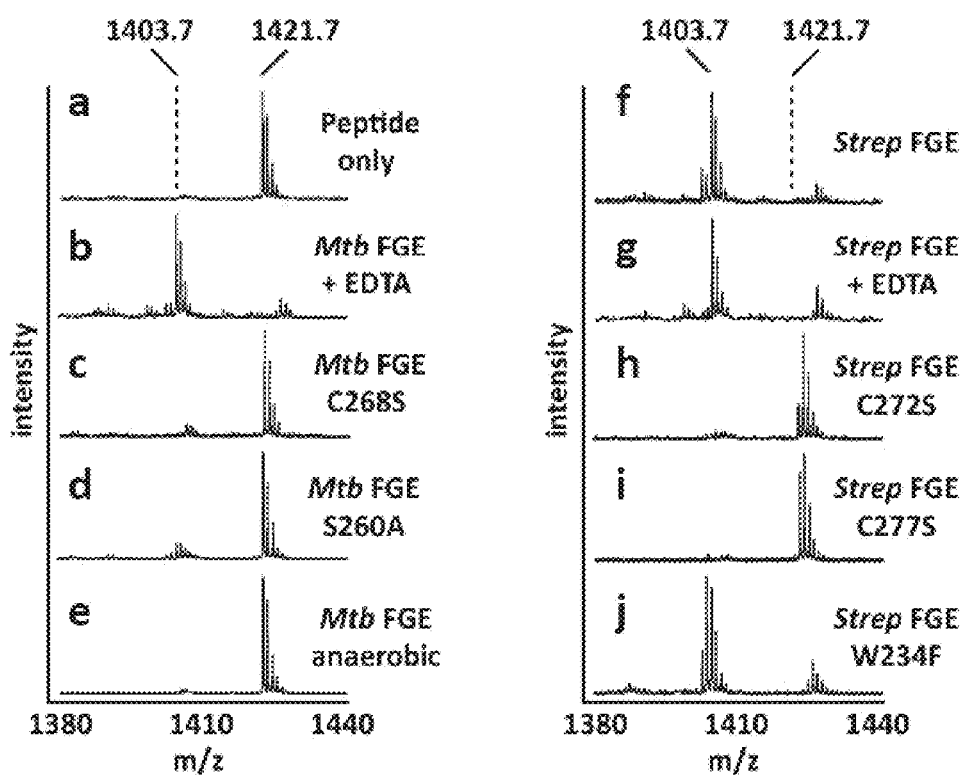
FIG. 13 provides data illustrating that Mtb and Strep FGE activity is dependent upon molecular oxygen but independent of metal cofactors. (a) A synthetic peptide resembling the sulfatase motif (mass=1421.7 Da) was used as a substrate for FGE. Conversion of cysteine to FGly resulted in a loss of 18 Da, which was detected by mass spectrometry. (b,g) Metal chelator EDTA had no effect on activity. (c,h,i) Loss of active site cysteines in Mtb and Strep FGE abolished activity. (d) Loss of active site Ser260 in Mtb FGE significantly reduced activity. (e) Mtb FGE was inactive in the absence of molecular oxygen. (f) WT Strep FGE was able to oxidize the synthetic peptide. (j) Active site Trp234 in Strep FGE is not essential for catalytic activity. The ion at m/z 1427 is the sodium adduct of the FGly-containing product peptide.
Figure 14:
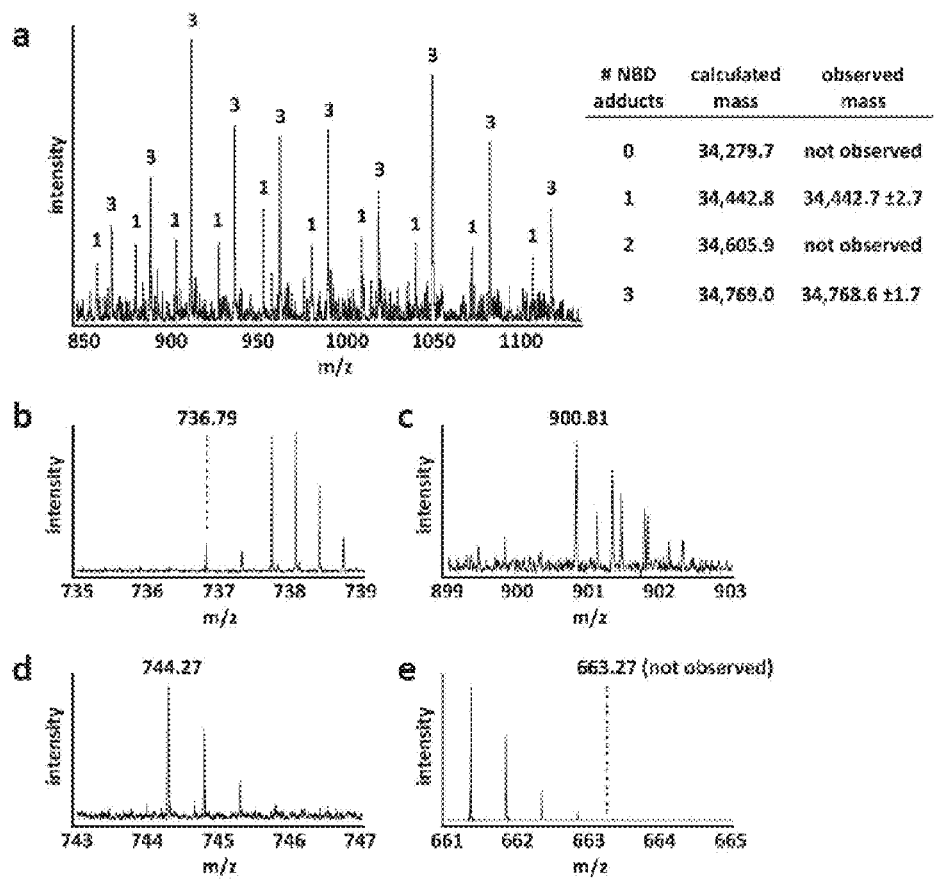
FIG. 14 provides data illustrating that active site cysteines 272 and 277 in Strep FGE are engaged in a partial disulfide bond. (a) Strep FGE was labeled with NBD and adducts were detected by mass spectrometry. Two populations of NBD-modified Strep FGE were observed. One population had a single NBD adduct, which corresponds to disulfide connected Cys272 and Cys277 (see b). The other population had three NDB adducts corresponding to Cys 272 and Cys277 thiols (see c). Multiple charge states are shown for both populations. Numbers above each ion peak indicate the number of NBD adducts attributed to each population. (b-d) NBD adducts were mapped to each surface-exposed thiol using mass spectrometry after trypsinolysis. Shown are the +2 charge state ions corresponding to disulfide connected Cys272 and Cys277 (b, calculated mass=1,471.58; observed mass=1,471.58), NBD adducts on both Cys272 and Cys277 (c, calculated mass=1,799.58; observed mass=1,799.61), and an NBD adduct on Cys301 (d, calculated mass=1486.52; observed mass=1,486.54). (e) Cys301 was not observed as a free thiol (expected position of +2 charge state ion shown).

An unmarked, in-frame genetic deletion of the FGE-encoding open reading frame Rv0712 was created in Mtb H37Rv using allelic replacement (Parish et al. (2000) Microbiology 146 (Pt 8), 1969-75.). A 2-kb region upstream of Rv0712 was amplified and inserted into the mycobacterial delivery vector p2NILX between HindIII and XbaI restriction sites. p2NILX is derived from pNIL (Parish et al. (2000) Microbiology 146 (Pt 8), 1969-75) and modified with the addition of an XbaI restriction site between KpnI and NotI restriction sites. A 2-kb region downstream of Rv0712 was amplified and inserted into p2NILX between XbaI and PacI restriction sites. Selection markers lacZ and sacB were digested from pGOAL17 and ligated into p2NILX using the PacI restriction site. The completed delivery vector was treated with UV light (120 mJ cm$^{-2}$) and electroporated into electrocompetent Mtb II37Rv as previously described (Hatfull, G. F. & Jacobs, W. R. J. (eds.) *Molecular Genetics of Mycobacteria* (ASM Press, Washington, D.C., 2000)). Selection of the mutant was performed as previously described (Parish et al. (2000) Microbiology 146 (Pt 8), 1969-75), and genotype was confirmed by Southern analysis (FIG. 9). The complemented strain was produced by transforming the Δfge strain with the integrating vector pMV306.kan containing the entire Rv0712 open reading frame under the control of the glutamine synthase promoter.

Sulfatase/Phosphatase Assay.

Mtb H37Rv strains were grown in 7H9 media supplemented with ADC (Becton Dickinson) at 37° C. until $OD_{600}$=1.0. Cells were lysed by mechanical disruption using 0.1 mm zirconia beads (FastPrep, MP Biomedicals) and the crude lysate was cleared by centrifugation and filtered through a 0.22 μm membrane. Cleared lysate samples were normalized for total protein concentration (Biorad AC/DC protein assay kit) and 50 μg of lysate protein was added to buffer (50 mM Tris pH 7.5, 500 mM NaCl, 100 μM $MgCl_2$, 100 μM $MnCl_2$, 100 μM $CaCl_2$), protease inhibitors (Protease Inhibitor cocktail set III, EMD Bioscience), and 8 mM 4-methylumbelliferyl sulfate (4MUS). Limpet sulfatase (Sigma) was used at a final concentration of 1 μg/ml as a positive control. Reactions were incubated at 37° C. for 3 h and stopped by adding 4 volumes of 0.5 M $Na_2CO_3$/$NaHCO_3$ pH 10.5. Sulfatase activity was measured using a fluorimeter (Gemini XL, Molecular Devices) using excitation and emission wavelengths of 360 nm and 460 nm, respectively. Sulfatase/phosphatase inhibitors were used per manufacturer's instructions and included microcystin, cantharidin, p-bromotetramisole, sodium vanadate, sodium molybdate, sodium tartrate, and imidazole (Phosphatase Inhibitor Cocktail 1 & 2, Sigma). Sulfatase activity of recombinant Rv2407, Rv3406 and Rv3762c was determined using the same conditions mentioned above, with the addition of 1 mM α-ketoglutarate, 200 μM ascorbate and 100 μM $FeCl_2$ to the buffer. Phosphatase activity was monitored as described above except with the substitution of 4-methylumbelliferyl phosphate for 4MUS.

NBD Labeling.

$His_6$-tagged Strep FGE was treated with 1:50 (w/w) TEV protease to remove the N-terminal $His_6$-tag before NBD labeling and mass spectrometric analyses. Strep FGE (45 μM) was incubated in buffer (25 mM potassium phosphate pH 7.0, 150 mM NaCl) with 1 mM 4-chloro-7-nitrobenz-2-oxa-1,3-diazole (NBD-Cl, Invitrogen) for 30 min at RT (Ellis et al. (1997) Biochemistry 36, 15013-8). The sample was desalted by $C_{18}$ reversed-phase chromatography and protein-NBD adducts were detected by mass spectrometry (Bruker/Agilent Esquire). Mapping of NBD adducts was performed by digesting NBD-reacted Strep FGE with 1:50 (w/w) trypsin, desalting by $C_{18}$ reversed-phase chromatography and analyzing the resulting peptide fragments using electrospray ionization Fourier-transform ion cyclotron resonance mass spectrometry (Bruker 9.4T Apex III).

Example 13

Identification and Cloning of an FGE of *M. Tuberculosis*

The *Mycobacterium tuberculosis* (Mtb) H37Rv open reading frame Rv0712 was identified by BLAST analysis (Altschul, et al. (1997) Nucleic Acids Res 25, 3389-402) to be over 30% identical to the human FGE SUMF1 (Cosma et al. (2003) Cell 113, 445-56 (2003); Dierks et al. (2003) Cell 113, 435-44). Recombinant Rv0712 was able to modify a synthetic peptide containing the sulfatase motif as determined by mass spectrometry (FIG. 8, Panel a). The presence of FGly within the substrate was confirmed by treating the modified peptide with biotin hydrazide, which formed a covalent adduct with the peptide via hydrazone formation (FIG. 8, Panel b). Together these data implicate Rv0712 as Mtb's FGE.

Similar to the human genome, the Mtb genome appears to encode only one functional copy of FGE. Therefore, it was expected that disruption of Rv0712 in Mtb to produce a sulfatase-deficient strain. Rv0712 was disrupted in Mtb H37Rv using homologous recombination and confirmed by Southern analysis (FIG. 9). Δfge Mtb was viable and demonstrated no obvious growth defects in vitro.

Sulfatase activity of the Δfge strain was compared to that of wild-type (WT) H37Rv and to the Δfge mutant into which FGE expression was restored by complementation. Crude lysates were generated from these three Mtb strains and global sulfatase activity was determined using the general substrate 4-methylumbelliferyl sulfate (4MUS). The Δfge strain exhibited a substantial, yet surprisingly incomplete loss of sulfatase activity (FIG. 8, Panel c). While it may have been possible that the residual sulfatase activity resulted from phosphatases acting on 4MUS, when sulfatase activity was monitored in the presence of a cocktail of broad spectrum sulfatase/phosphatase inhibitors, Δfge was not affected. Indeed, activity in lysates from WT and complemented Δfge was reduced by about 40% in the presence of the inhibitor cocktail, matching the sulfatase activity of Δfge in the absence of inhibitors (FIG. 8, Panel c). Because the applied inhibitors are known to inhibit FGE-activated sulfatases (Stankiewicz et al. (1988) Biochemistry 27, 206-12), these data suggest that Mtb possesses FGE-independent sulfatases.

To further verify that promiscuous phosphatases were not responsible for the residual sulfatase activity, phosphatase activity of crude lysates from each strain was monitored using 4-methylumbelliferyl phosphate. All three strains exhibited the same level of phosphatase activity in the absence of inhibitors, but activity was abolished in all strains in the presence of the inhibitors (FIG. 8, Panel d). These data further indicate that phosphatases are not accountable for the residual 4MUS hydrolysis activity observed in the Δfge strain and that FGE-activated sulfatases are responsible for approximately 40% of the total sulfatase activity in Mtb lysate.

The Mtb genome was searched for potential sources of FGE-independent sulfatase activity. The majority of known or putative prokaryotic sulfatases are homologous to eukaryotic sulfatases and contain the sulfatase motif. However, some prokaryotes also have FGE-independent sulfatases that do not require FGly and presumably operate via different mechanisms. These enzymes may not be sensitive to broad-spectrum sulfatase/phosphatase inhibitors. FGE-independent sulfatases are not homologous to FGE-activated sulfatases and have been classified into one of two enzyme families, the metallo-β-lactamases and Fe(II) α-ketoglutarate-dependent $dioxygenases_{18-20}$. Based on sequence similarity with known FGE-independent sulfatases from other prokaryotes, Mtb has at least three putative FGE-independent sulfatases encoded by open reading frames Rv2407, Rv3406 and Rv3762c. Recombinant forms of Rv2407, Rv3406 and Rv3762c were expressed in *E. coli*, but the purified proteins exhibited no activity in the 4MUS assay, indicating that these putative sulfatases are probably not responsible for the residual sulfatase activity in Δfge Mtb (FIG. 10). Considering the lack of sequence similarity among FGE-independent sulfatases, Mtb may have other sulfatases not detectable by BLAST analysis.

Example 14

Structure of Mtb FGE

In order to understand better the unique enzymatic mechanism and substrate binding characteristics of prokaryotic FGEs, the structure of the Mtb FGE ortholog from *Streptomyces coelicolor* (Strep) was determined to a resolution of 2.1 Å. The overall topology of the bacterial FGE is remarkably similar to the recently determined human FGE structure (Dierks, et al. (2005) Cell 121, 541-52). (FIG. 11A). Similar to human FGE, Strep FGE has low secondary structure content, containing 16% α-helix and 12% β-sheet. Both share the novel "FGE fold," but the Strep FGE variant contains only one $Ca^{2+}$ ion as determined by coordination geometry and inductively coupled plasma-atomic emission spectroscopy (ICP-AES) (FIG. 12). The human variant is stabilized by two $Ca_{2+}$ ions; this difference is apparently due to a Glu66Ala substitution in Strep FGE that disrupts an appropriate coordination environment (FIG. 3, panel b). ICP-AES data indicate that Mtb FGE lacks both $Ca^{2+}$ ions (FIG. 12), suggesting that the FGE fold does not require stabilization by divalent cations.

The active sites of the prokaryotic and human FGE are remarkably similar. Both are approximately 20 Å in length, 12 Å in width, and 10 Å in depth and can accommodate only 6 of the 13 amino acids that define the sulfatase motif. Considering that the sulfatase motif extends towards the C-terminus of the peptide substrate for another eight residues beyond the core consensus sequence (CXPXR) (FIG. 7, panel b), it is possible that FGE has evolved a secondary binding region to aid in substrate recognition, similar to other proteins such as thrombin and botulinum neurotoxin (Hageman et al. (1974) *Arch Biochem Biophys* 164:707-15; Breidenbach et al. (2004) *Nature* 432:925-9). Indeed, when conserved residues between Strep, Mtb, human and other putative FGEs are mapped on the surface of the Strep FGE molecule, a region of high conservation is observed where the C-terminal section of the sulfatase motif could possibly bind (FIG. 11C).

FGE is thought to catalyze the oxidation of a thiol to an aldehyde using two conserved cysteine residues within its active site (Dierks et al. (2005) *Cell* 121, 541-52; Roeser et al. (2006) *Proc Natl Acad Sci USA* 103, 81-6). These cysteines in Mtb (Cys263 and Cys268) and Strep FGE (Cys272 and Cys277) are required for substrate turnover as serine mutants were unable to generate FGly in vitro (FIG. 8, panel a, FIG. 13, panels c, h, i). Interestingly, the oxidation state of these residues is different between the five monomers within the asymmetric unit. Omit maps showed Cys272 and Cys277 to be engaged in partial disulfides in three of the five Strep FGE monomers within the asymmetric unit (FIGS. 11D-11E, and data not shown). Biochemical confirmation of these partial disulfides was provided by treating native Strep FGE's three solvent-exposed cysteines with the thiol-labeling reagent 4-chloro-7-nitrobenz-2-oxa-1,3-diazole (NBD). Two distinct populations corresponding to Strep FGE with either 1 or 3 NBD adducts were detected by intact-protein mass spectrometry (FIG. 14), confirming that approximately one-third of these two proximal cysteines are linked in a disulfide bond.

In addition to the two active site cysteines, Strep and Mtb FGE also require molecular oxygen for catalysis as no FGly formation was observed in reactions performed in an anaerobic environment (FIG. 13, panel e, and data not shown). As a member of the oxygenase family, FGE might be expected to contain a transition metal, such as Fe or Cu, or an organic cofactor, such as FADH, for activation of molecular oxygen. However, analysis by ICP-AES and x-ray absorption edge scanning indicated that active Mtb and Strep FGE lack all redox active metals (FIG. 12 and data not shown). Additionally, these FGEs do not require addition of metals to function in assays in vitro and can function in the presence of EDTA (FIG. 13, panels b, g). Similarly, UV-visible absorption spectroscopy did not reveal the presence of chromophoric organic cofactors (data not shown). Together with electron density information for Strep FGE, these data indicate that prokaryotic FGEs, similar to human FGE, do not use exogenous cofactors for catalysis.

As an alternate means of activating molecular oxygen, FGE may function similarly to other cofactor-less oxygenases and make unique use of conventional residues$_{25}$. Absolutely conserved residues within reactive distance from Strep FGE's catalytic cysteine pair include Trp234 and Ser269. Roeser et al. have theorized that Trp234 may function to activate molecular oxygen (Roeser et al. (2006) Proc Natl Acad Sci USA 103:81-6), similar to the proposed mechanism of $O_2$ reduction by catalytic antibodies$_{26}$. However, mutation of Trp234 to Phe did not abolish activity (FIG. 13, panel j), indicating that molecular oxygen activation must be achieved by another route. Activity was severely reduced by the Ser269Ala equivalent mutation in Mtb FGE (Ser260Ala) (FIG. 13, panel d), but it is currently unknown how this residue plays a role in FGE's catalytic cycle.

Interestingly, Cys272 itself may be involved in activating molecular oxygen. All five modeled Cys272 residues within the asymmetric unit of Strep FGE have extra electron density extending away from their alternate, non-disulfide bound conformations. Omit maps indicate that this extra density could be modeled as one water molecule or a hydroperoxide moiety with partial occupancy (FIG. 13, panels d, e). NBD-labeling experiments using the Cys277Ser Strep FGE mutant indicate that Cys272 is not a reactive thiol in a subpopulation of enzyme molecules (FIG. 15), suggesting that the extra density corresponds to a moiety covalently bound to Cys272, such as hydroperoxide. Previously published structures of the human FGE have also suggested that this extra density could be hydroperoxide or cysteine sulfenic acid combined with a bound water molecule$_{21}$. However, the latter fits the observed electron density in Strep FGE poorly. Furthermore, no sulfenic acid was detected when Strep FGE was treated with NBD-chloride (FIG. 15 and FIG. 14). The presence of hydroperoxide modeled with partial occupancy cannot be ruled out based on the observed electron density of Strep FGE. However, mass spectrometric analysis of intact Strep and Mtb FGE revealed no mass anomaly (FIG. 16 and data not shown), suggesting that if Cys272 is modified, the modification is transient or acid labile.

That which is claimed is:

1. A non-naturally occurring, recombinant polypeptide comprising a heterologous sulfatase motif having a 2-formylglycine residue, wherein the heterologous sulfatase motif is less than 13 amino acid residues and contain a contiguous sequence of the formula:

$X_1(FGly)X_2Z_2X_3R$ where
FGly is a 2-formylglycine residue;
$Z_2$ is a proline or alanine residue;
$X_1$ is present or absent and, when present, is any amino acid, with the proviso that when the heterologous sulfatase motif is at an N-terminus of the aldehyde tagged polypeptide, $X_1$ is present; and $X_2$ and $X_3$ are each independently any amino acid,
wherein the heterologous sulfatase motif does not include a threonine-glycine-arginine (TGR) motif C-terminal to the arginine residue of the heterologous sulfatase motif.

2. The non-naturally occurring, recombinant polypeptide of claim 1, wherein the heterologous sulfatase motif
is positioned at a C-terminus of the non-naturally occurring, recombinant polypeptide;
is present in a terminal loop of the non-naturally occurring, recombinant polypeptide;
is, when the non-naturally occurring, recombinant polypeptide is a transmembrane protein, present at an internal site within an extracellular loop or an intracellular loop;

is present at an internal site or at the N-terminus of the non-naturally occurring, recombinant polypeptide, and is solvent-accessible when the polypeptide is folded; and/or is present at a site of post-translational modification.

3. The non-naturally occurring, recombinant polypeptide of claim 1, wherein $X_1$, when present, $X_2$, and $X_3$ are each independently an aliphatic amino acid, a sulfur-containing amino acid, or a polar, uncharged amino acid.

4. The non-naturally occurring, recombinant polypeptide of claim 1, wherein the $X_1$, when present, is L, M, V, S or T.

5. The method non-naturally occurring, recombinant polypeptide of claim 1, wherein $X_2$ and $X_3$ are each independently S, T, A, V, G, or C.

6. The non-naturally occurring, recombinant polypeptide of claim 1, wherein the heterologous sulfatase motif is L(FGly)TPSR.

7. A modified non-naturally occurring, recombinant polypeptide comprising a heterologous sulfatase motif having a 2-formylglycine residue covalently attached to a moiety of interest, wherein the heterologous sulfatase motif is less than 13 amino acid residues and contain a contiguous sequence of the formula:

$X_1(FGly')X_2Z_2X_3R$ where
FGly' is the 2-formylglycine residue covalently attached to the moiety of interest;
$Z_2$ is a proline or alanine residue;
$X_1$ is present or absent and, when present, is any amino acid, with the proviso that when the heterologous sulfatase motif is at an N-terminus of the polypeptide, $X_1$ is present; and
$X_2$ and $X_3$ are each independently any amino acid, and wherein the heterologous sulfatase motif does not include a threonine-glycine-arginine (TGR) motif C-terminal to the arginine residue of the heterologous sulfatase motif.

8. The modified non-naturally occurring, recombinant polypeptide of claim 7, wherein the moiety of interest is a water-soluble polymer, a detectable label, a drug, a toxin, a peptide, or an immobilization tag.

9. The modified non-naturally occurring, recombinant polypeptide of claim 7, wherein the modified sulfatase motif is positioned in the modified polypeptide at a site of post-translational modification of that is native or non-native to the parent of the modified polypeptide.

10. The modified non-naturally occurring, recombinant polypeptide of claim 7, wherein the modified non-naturally occurring, recombinant polypeptide is selected from the group consisting of an Fc fragment, an antibody, an antigen-binding fragment of an antibody, a blood factor, a fibroblast growth factor, a protein vaccine, and an enzyme.

11. The modified non-naturally occurring, recombinant polypeptide of claim 7, wherein the moiety of interest is a drug.

12. The modified non-naturally occurring, recombinant polypeptide of claim 7, wherein the moiety of interest is a peptide.

13. A non-naturally occurring, recombinant polypeptide comprising a heterologous sulfatase motif having a 2-formylglycine residue, wherein the heterologous sulfatase motif is less than 9 amino acid residues and contains a contiguous sequence of the formula:

$X_1(FGly)X_2Z_2X_3R$ where
FGly is a 2-formylglycine residue;
$Z_2$ is a proline or alanine residue;
$X_1$ is present or absent and, when present, is any amino acid, with the proviso that when the heterologous sulfatase motif is at an N-terminus of the aldehyde tagged polypeptide, $X_1$ is present; and
$X_2$ and $X_3$ are each independently any amino acid.

14. The non-naturally occurring, recombinant polypeptide of claim 13, wherein the $X_1$, when present, is L, M, V, S or T.

15. The non-naturally occurring, recombinant polypeptide of claim 13, wherein $X_2$ and $X_3$ are each independently S, T, A, V, G, or C.

16. The non-naturally occurring, recombinant polypeptide of claim 13, wherein the heterologous sulfatase motif is L(FGly)TPSR.

17. The non-naturally occurring, recombinant polypeptide of claim 13, wherein the non-naturally occurring, recombinant polypeptide comprises an Fc fragment.

18. The non-naturally occurring, recombinant polypeptide of claim 13, wherein the non-naturally occurring, recombinant polypeptide comprises an Fc polypeptide.

19. The non-naturally occurring, recombinant polypeptide of claim 13, wherein the non-naturally occurring, recombinant polypeptide is an antibody.

20. The non-naturally occurring, recombinant polypeptide of claim 19, wherein the antibody is an IgG antibody.

21. The non-naturally occurring, recombinant polypeptide of claim 19, wherein the antibody is a humanized antibody.

22. The non-naturally occurring, recombinant polypeptide of claim 13, wherein the non-naturally occurring, recombinant polypeptide comprises an antigen-binding fragment of an antibody.

23. The non-naturally occurring, recombinant polypeptide of claim 22, wherein the non-naturally occurring, recombinant polypeptide comprises a Fab or Fv.

24. The non-naturally occurring, recombinant polypeptide of claim 13, wherein the non-naturally occurring, recombinant polypeptide comprises a single chain antibody.

25. The non-naturally occurring, recombinant polypeptide of claim 13, wherein the non-naturally occurring, recombinant polypeptide is a blood factor.

26. The non-naturally occurring, recombinant polypeptide of claim 25, wherein the blood factor is Factor VIII.

27. The non-naturally occurring, recombinant polypeptide of claim 13, wherein the non-naturally occurring, recombinant polypeptide is a fibroblast growth factor.

28. The non-naturally occurring, recombinant polypeptide of claim 13, wherein the non-naturally occurring, recombinant polypeptide is a protein vaccine.

29. The non-naturally occurring, recombinant polypeptide of claim 13, wherein the non-naturally occurring, recombinant polypeptide is an enzyme.

30. A modified non-naturally occurring, recombinant polypeptide comprising a heterologous sulfatase motif having a 2-formylglycine residue covalently attached to a moiety of interest, wherein the heterologous sulfatase motif is less than 9 amino acid residues and contains a contiguous sequence of the formula:

$X_1(FGly')X_2Z_2X_3R$ where
FGly' is the 2-formylglycine residue covalently attached to the moiety of interest;
$Z_2$ is a proline or alanine residue;

X₁ is present or absent and, when present, is any amino acid, with the proviso that when the heterologous sulfatase motif is at an N-terminus of the polypeptide, X₁ is present; and X₂ and X₃ are each independently any amino acid.

31. The modified non-naturally occurring, recombinant polypeptide of claim 30, wherein the X₁, when present, is L, M, V, S or T.

32. The modified non-naturally occurring, recombinant polypeptide of claim 30, wherein X₂ and X₃ are each independently S, T, A, V, G, or C.

33. The modified non-naturally occurring, recombinant polypeptide of claim 30, wherein the heterologous sulfatase motif is L(FGly')TPSR.

34. The modified non-naturally occurring, recombinant polypeptide of claim 30, wherein the non-naturally occurring, recombinant polypeptide comprises an Fc fragment.

35. The modified non-naturally occurring, recombinant polypeptide of claim 30, wherein the non-naturally occurring, recombinant polypeptide comprises an Fc polypeptide.

36. The modified non-naturally occurring, recombinant polypeptide of claim 30, wherein the non-naturally occurring, recombinant polypeptide is an antibody.

37. The modified non-naturally occurring, recombinant polypeptide of claim 36, wherein the antibody is an IgG antibody.

38. The modified non-naturally occurring, recombinant polypeptide of claim 36, wherein the antibody is a humanized antibody.

39. The modified non-naturally occurring, recombinant polypeptide of claim 30, wherein the non-naturally occurring, recombinant polypeptide comprises an antigen-binding fragment of an antibody.

40. The modified non-naturally occurring, recombinant polypeptide of claim 39, wherein the non-naturally occurring, recombinant polypeptide comprises a Fab or Fv.

41. The modified non-naturally occurring, recombinant polypeptide of claim 30, wherein the non-naturally occurring, recombinant polypeptide comprises a single chain antibody.

42. The modified non-naturally occurring, recombinant polypeptide of claim 30, wherein the non-naturally occurring, recombinant polypeptide is a blood factor.

43. The modified non-naturally occurring, recombinant polypeptide of claim 42, wherein the blood factor is Factor VIII.

44. The modified non-naturally occurring, recombinant polypeptide of claim 30, wherein the non-naturally occurring, recombinant polypeptide is a fibroblast growth factor.

45. The modified non-naturally occurring, recombinant polypeptide of claim 30, wherein the non-naturally occurring, recombinant polypeptide is a protein vaccine.

46. The modified non-naturally occurring, recombinant polypeptide of claim 30, wherein the non-naturally occurring, recombinant polypeptide is an enzyme.

47. The modified non-naturally occurring, recombinant polypeptide of claim 30, wherein the moiety of interest is a drug.

48. The modified non-naturally occurring, recombinant polypeptide of claim 30, wherein the moiety of interest is a peptide.

49. A modified non-naturally occurring, recombinant polypeptide comprising a heterologous sulfatase motif having a 2-formylglycine residue covalently attached to a moiety of interest, wherein the heterologous sulfatase motif is less than 9 amino acid residues and contains a contiguous sequence of the formula:

$$X_1(FGly')X_2Z_2X_3R$$

where

FGly' is the 2-formylglycine residue covalently attached to the moiety of interest through a hydrazone, oxime or semicarbazone linkage;

Z₂ is a proline or alanine residue;

X₁ is present or absent and, when present, is any amino acid, with the proviso that when the heterologous sulfatase motif is at an N-terminus of the polypeptide, X₁ is present; and X₂ and X₃ are each independently any amino acid.

* * * * *

SEQUENCE LISTING

<160> NUMBER OF SEQ ID NOS: 96

<210> SEQ ID NO 1
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 1

Leu Cys Thr Pro Ser Arg
1               5

<210> SEQ ID NO 2
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 2

Ala Ala Leu Leu Thr Gly Arg
1               5

<210> SEQ ID NO 3
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 3

Ser Gln Leu Leu Thr Gly Arg
1               5

<210> SEQ ID NO 4
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 4

Ala Ala Phe Met Thr Gly Arg
1               5

<210> SEQ ID NO 5
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 5

Ala Ala Phe Leu Thr Gly Arg
1               5

<210> SEQ ID NO 6
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 6

Ser Ala Phe Leu Thr Gly Arg
1               5

<210> SEQ ID NO 7
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 7

Ala Ser Ile Leu Thr Gly Lys
1               5

<210> SEQ ID NO 8
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 8

Val Ser Phe Leu Thr Gly Arg
1               5

<210> SEQ ID NO 9
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 9

Ala Ser Leu Leu Thr Gly Leu
1               5

<210> SEQ ID NO 10
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 10

Ala Ser Ile Leu Ile Thr Gly
1               5

<210> SEQ ID NO 11
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 11

Val Ser Phe Leu Thr Gly Arg
1               5

<210> SEQ ID NO 12
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 12

Ser Ala Ile Met Thr Gly Arg
1               5

<210> SEQ ID NO 13
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 13

Ser Ala Ile Val Thr Gly Arg
1               5

<210> SEQ ID NO 14
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 14

Thr Asn Leu Trp Arg Gly
1               5

<210> SEQ ID NO 15
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 15

Thr Asn Leu Trp Arg Gly Gln
1               5

<210> SEQ ID NO 16
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 16

Thr Asn Leu Cys Ala Ala Ser
1               5

<210> SEQ ID NO 17
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 17

Val Ser Leu Trp Thr Gly Lys
1               5

<210> SEQ ID NO 18
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 18

Ser Met Leu Leu Thr Gly
1               5

```
<210> SEQ ID NO 19
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 19

Ser Met Leu Leu Thr Gly Asn
1               5

<210> SEQ ID NO 20
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 20

Ser Met Leu Leu Thr Gly Thr
1               5

<210> SEQ ID NO 21
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 21

Ala Ser Phe Met Ala Gly Gln
1               5

<210> SEQ ID NO 22
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 22

Ala Ser Leu Leu Thr Gly Leu
1               5

<210> SEQ ID NO 23
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 23

Gly Ser Leu Phe Thr Gly Arg
1               5

<210> SEQ ID NO 24
<211> LENGTH: 7
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (6)..(6)
<223> OTHER INFORMATION: The amino acid at this position can be an M
      (Met) or an A (Ala).

<400> SEQUENCE: 24
```

```
Cys Gly Pro Ser Arg Xaa Ser
1               5

<210> SEQ ID NO 25
<211> LENGTH: 6
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (6)..(6)
<223> OTHER INFORMATION: The amino acid at this position can be an M
      (Met) or an A (Ala).

<400> SEQUENCE: 25

Cys Gly Pro Ser Arg Xaa
1               5

<210> SEQ ID NO 26
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 26

Met Cys Thr Pro Ser Arg
1               5

<210> SEQ ID NO 27
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 27

Val Cys Thr Pro Ser Arg
1               5

<210> SEQ ID NO 28
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 28

Leu Cys Ser Pro Ser Arg
1               5

<210> SEQ ID NO 29
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 29

Leu Cys Ala Pro Ser Arg
1               5

<210> SEQ ID NO 30
<211> LENGTH: 6
<212> TYPE: PRT
<213> ORGANISM: Artificial sequence
<220> FEATURE:
```

```
<223> OTHER INFORMATION: Synthetic amino acid sequence

<400> SEQUENCE: 30

Leu Cys Val Pro Ser Arg
1               5

<210> SEQ ID NO 31
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 31

Leu Cys Gly Pro Ser Arg
1               5

<210> SEQ ID NO 32
<211> LENGTH: 6
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (2)..(2)
<223> OTHER INFORMATION: The amino acid at this position is a
      formylglycine.

<400> SEQUENCE: 32

Leu Xaa Thr Pro Ser Arg
1               5

<210> SEQ ID NO 33
<211> LENGTH: 6
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (2)..(2)
<223> OTHER INFORMATION: The amino acid at this position is a
      formylglycine.

<400> SEQUENCE: 33

Met Xaa Thr Pro Ser Arg
1               5

<210> SEQ ID NO 34
<211> LENGTH: 6
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (2)..(2)
<223> OTHER INFORMATION: The amino acid at this position is a
      formylglycine.

<400> SEQUENCE: 34

Val Xaa Thr Pro Ser Arg
1               5

<210> SEQ ID NO 35
<211> LENGTH: 6
<212> TYPE: PRT
<213> ORGANISM: Artificial sequence
```

```
<220> FEATURE:
<223> OTHER INFORMATION: Synthetic amino acid sequence
<220> FEATURE:
<221> NAME/KEY: MISC_FEATURE
<222> LOCATION: (2)..(2)
<223> OTHER INFORMATION: The amino acid at this position is a
      formylglycine.

<400> SEQUENCE: 35

Leu Xaa Ser Pro Ser Arg
1               5

<210> SEQ ID NO 36
<211> LENGTH: 6
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (2)..(2)
<223> OTHER INFORMATION: The amino acid at this position is a
      formylglycine.

<400> SEQUENCE: 36

Leu Xaa Ala Pro Ser Arg
1               5

<210> SEQ ID NO 37
<211> LENGTH: 6
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (2)..(2)
<223> OTHER INFORMATION: The amino acid at this position is a
      formylglycine.

<400> SEQUENCE: 37

Leu Xaa Val Pro Ser Arg
1               5

<210> SEQ ID NO 38
<211> LENGTH: 6
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (2)..(2)
<223> OTHER INFORMATION: The amino acid at this position is a
      formylglycine.

<400> SEQUENCE: 38

Leu Xaa Gly Pro Ser Arg
1               5

<210> SEQ ID NO 39
<211> LENGTH: 299
<212> TYPE: PRT
<213> ORGANISM: Mycobacterium tuberculosis

<400> SEQUENCE: 39

Met Leu Thr Glu Leu Val Asp Leu Pro Gly Gly Ser Phe Arg Met Gly
1               5                   10                  15

Ser Thr Arg Phe Tyr Pro Glu Glu Ala Pro Ile His Thr Val Thr Val
```

```
                    20                  25                  30

Arg Ala Phe Ala Val Glu Arg His Pro Val Thr Asn Ala Gln Phe Ala
                35                  40                  45

Glu Phe Val Ser Ala Thr Gly Tyr Val Thr Val Ala Glu Gln Pro Leu
    50                  55                  60

Asp Pro Gly Leu Tyr Pro Gly Val Asp Ala Ala Asp Leu Cys Pro Gly
65                  70                  75                  80

Ala Met Val Phe Cys Pro Thr Ala Gly Pro Val Asp Leu Arg Asp Trp
                85                  90                  95

Arg Gln Trp Trp Asp Trp Val Pro Gly Ala Cys Trp Arg His Pro Phe
            100                 105                 110

Gly Arg Asp Ser Asp Ile Ala Asp Arg Ala Gly His Pro Val Val Gln
        115                 120                 125

Val Ala Tyr Pro Asp Ala Val Ala Tyr Ala Arg Trp Ala Gly Arg Arg
    130                 135                 140

Leu Pro Thr Glu Ala Glu Trp Glu Tyr Ala Ala Arg Gly Gly Thr Thr
145                 150                 155                 160

Ala Thr Tyr Ala Trp Gly Asp Gln Glu Lys Pro Gly Gly Met Leu Met
                165                 170                 175

Ala Asn Thr Trp Gln Gly Arg Phe Pro Tyr Arg Asn Asp Gly Ala Leu
            180                 185                 190

Gly Trp Val Gly Thr Ser Pro Val Gly Arg Phe Pro Ala Asn Gly Phe
        195                 200                 205

Gly Leu Leu Asp Met Ile Gly Asn Val Trp Glu Trp Thr Thr Thr Glu
    210                 215                 220

Phe Tyr Pro His His Arg Ile Asp Pro Pro Ser Thr Ala Cys Cys Ala
225                 230                 235                 240

Pro Val Lys Leu Ala Thr Ala Ala Asp Pro Thr Ile Ser Gln Thr Leu
                245                 250                 255

Lys Gly Gly Ser His Leu Cys Ala Pro Glu Tyr Cys His Arg Tyr Arg
            260                 265                 270

Pro Ala Ala Arg Ser Pro Gln Ser Gln Asp Thr Ala Thr Thr His Ile
        275                 280                 285

Gly Phe Arg Cys Val Ala Asp Pro Val Ser Gly
    290                 295

<210> SEQ ID NO 40
<211> LENGTH: 42
<212> TYPE: DNA
<213> ORGANISM: Artificial sequence
<220> FEATURE:
<223> OTHER INFORMATION: Synthetic nucleic acid sequence

<400> SEQUENCE: 40
ccactgtgca caccatcgcg gatgtccgac caccccaccg cc                        42

<210> SEQ ID NO 41
<211> LENGTH: 57
<212> TYPE: DNA
<213> ORGANISM: Artificial sequence
<220> FEATURE:
<223> OTHER INFORMATION: Synthetic nucleic acid sequence

<400> SEQUENCE: 41
catggcacca ctgtgcacac catcgcgggg ctcgctgttc accggccgcg acgtcca       57

<210> SEQ ID NO 42
```

```
<211> LENGTH: 55
<212> TYPE: DNA
<213> ORGANISM: Artificial sequence
<220> FEATURE:
<223> OTHER INFORMATION: Synthetic nucleic acid sequence

<400> SEQUENCE: 42
tatggacgtc gcggccggtg aacagcgagc cccgcgatgg tgtgcacagt ggtgc       55

<210> SEQ ID NO 43
<211> LENGTH: 33
<212> TYPE: DNA
<213> ORGANISM: Artificial sequence
<220> FEATURE:
<223> OTHER INFORMATION: Synthetic nucleic acid sequence

<400> SEQUENCE: 43
gcaccaccac caccaccact gagatccggc tgc                              33

<210> SEQ ID NO 44
<211> LENGTH: 29
<212> TYPE: DNA
<213> ORGANISM: Artificial sequence
<220> FEATURE:
<223> OTHER INFORMATION: Synthetic nucleic acid sequence

<400> SEQUENCE: 44
ccatggcacc actggccaca ccatcgcgg                                   29

<210> SEQ ID NO 45
<211> LENGTH: 29
<212> TYPE: DNA
<213> ORGANISM: Artificial sequence
<220> FEATURE:
<223> OTHER INFORMATION: Synthetic nucleic acid sequence

<400> SEQUENCE: 45
cggccgcgat gtgcgccttg aagatctgc                                   29

<210> SEQ ID NO 46
<211> LENGTH: 28
<212> TYPE: DNA
<213> ORGANISM: Artificial sequence
<220> FEATURE:
<223> OTHER INFORMATION: Synthetic nucleic acid sequence

<400> SEQUENCE: 46
gatccctgtg cacaccatcg cggtgagc                                    28

<210> SEQ ID NO 47
<211> LENGTH: 28
<212> TYPE: DNA
<213> ORGANISM: Artificial sequence
<220> FEATURE:
<223> OTHER INFORMATION: Synthetic nucleic acid sequence

<400> SEQUENCE: 47
ggccgctcac cgcgatggtg tgcacagg                                    28

<210> SEQ ID NO 48
<211> LENGTH: 30
<212> TYPE: DNA
<213> ORGANISM: Artificial sequence
<220> FEATURE:
<223> OTHER INFORMATION: Synthetic nucleic acid sequence

<400> SEQUENCE: 48
```

-continued

```
ccgcgtggat ccctggccac accatcgcgg                                         30

<210> SEQ ID NO 49
<211> LENGTH: 53
<212> TYPE: DNA
<213> ORGANISM: Artificial sequence
<220> FEATURE:
<223> OTHER INFORMATION: Synthetic nucleic acid sequence

<400> SEQUENCE: 49
ctatgctacc atggcgctgt gcacaccatc gcggaccatt cccttatcca ggc              53

<210> SEQ ID NO 50
<211> LENGTH: 37
<212> TYPE: DNA
<213> ORGANISM: Artificial sequence
<220> FEATURE:
<223> OTHER INFORMATION: Synthetic nucleic acid sequence

<400> SEQUENCE: 50
ctatgctagc ggccgcgaag ccacagctgc cctccac                                 37

<210> SEQ ID NO 51
<211> LENGTH: 33
<212> TYPE: DNA
<213> ORGANISM: Artificial sequence
<220> FEATURE:
<223> OTHER INFORMATION: Synthetic nucleic acid sequence

<400> SEQUENCE: 51
tataccatgg cgctggccac accatcgcgg acc                                     33

<210> SEQ ID NO 52
<211> LENGTH: 36
<212> TYPE: DNA
<213> ORGANISM: Artificial sequence
<220> FEATURE:
<223> OTHER INFORMATION: Synthetic nucleic acid sequence

<400> SEQUENCE: 52
ctatgctacc atggctgacc gagttggttg acctgc                                  36

<210> SEQ ID NO 53
<211> LENGTH: 33
<212> TYPE: DNA
<213> ORGANISM: Artificial sequence
<220> FEATURE:
<223> OTHER INFORMATION: Synthetic nucleic acid sequence

<400> SEQUENCE: 53
tagcatagct cgagctaccc ggacaccggg tcg                                     33

<210> SEQ ID NO 54
<211> LENGTH: 31
<212> TYPE: DNA
<213> ORGANISM: Artificial sequence
<220> FEATURE:
<223> OTHER INFORMATION: Synthetic nucleic acid sequence

<400> SEQUENCE: 54
gaggaattaa ccatgctgac cgagttggtt g                                       31

<210> SEQ ID NO 55
<211> LENGTH: 13
<212> TYPE: PRT
```

<213> ORGANISM: Artificial sequence
<220> FEATURE:
<223> OTHER INFORMATION: Synthetic amino acid sequence

<400> SEQUENCE: 55

Leu Cys Thr Pro Ser Arg Gly Ser Leu Phe Thr Gly Arg
1               5                   10

<210> SEQ ID NO 56
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 56

Leu Ala Thr Pro Ser Arg Gly Ser Leu Phe Thr Gly Arg
1               5                   10

<210> SEQ ID NO 57
<211> LENGTH: 374
<212> TYPE: PRT
<213> ORGANISM: Artificial sequence
<220> FEATURE:
<223> OTHER INFORMATION: Synthetic amino acid sequence

<400> SEQUENCE: 57

Met Ala Ala Pro Ala Leu Gly Leu Val Cys Gly Arg Cys Pro Glu Leu
1               5                   10                  15

Gly Leu Val Leu Leu Leu Leu Leu Ser Leu Leu Cys Gly Ala Ala
            20                  25                  30

Gly Ser Gln Glu Ala Gly Thr Gly Ala Gly Ala Gly Ser Leu Ala Gly
        35                  40                  45

Ser Cys Gly Cys Gly Thr Pro Gln Arg Pro Gly Ala His Gly Ser Ser
    50                  55                  60

Ala Ala Ala His Arg Tyr Ser Arg Glu Ala Asn Ala Pro Gly Pro Val
65                  70                  75                  80

Pro Gly Glu Arg Gln Leu Ala His Ser Lys Met Val Pro Ile Pro Ala
                85                  90                  95

Gly Val Phe Thr Met Gly Thr Asp Asp Pro Gln Ile Lys Gln Asp Gly
            100                 105                 110

Glu Ala Pro Ala Arg Arg Val Thr Ile Asp Ala Phe Tyr Met Asp Ala
        115                 120                 125

Tyr Glu Val Ser Asn Thr Glu Phe Glu Lys Phe Val Asn Ser Thr Gly
    130                 135                 140

Tyr Leu Thr Glu Ala Glu Lys Phe Gly Asp Ser Phe Val Phe Glu Gly
145                 150                 155                 160

Met Leu Ser Glu Gln Val Lys Thr Asn Ile Gln Gln Ala Val Ala Ala
                165                 170                 175

Ala Pro Trp Trp Leu Pro Val Lys Gly Ala Asn Trp Arg His Pro Glu
            180                 185                 190

Gly Pro Asp Ser Thr Ile Leu His Arg Pro Asp His Pro Val Leu His
        195                 200                 205

Val Ser Trp Asn Asp Ala Val Ala Tyr Cys Thr Trp Ala Gly Lys Arg
    210                 215                 220

Leu Pro Thr Glu Ala Glu Trp Glu Tyr Ser Cys Arg Gly Gly Leu His
225                 230                 235                 240

Asn Arg Leu Phe Pro Trp Gly Asn Lys Leu Gln Pro Lys Gly Gln His
                245                 250                 255

Tyr Ala Asn Ile Trp Gln Gly Glu Phe Pro Val Thr Asn Thr Gly Glu
            260                 265                 270

Asp Gly Phe Gln Gly Thr Ala Pro Val Asp Ala Phe Pro Asn Gly
        275                 280                 285

Tyr Gly Leu Tyr Asn Ile Val Gly Asn Ala Trp Glu Trp Thr Ser Asp
290                 295                 300

Trp Trp Thr Val His His Ser Val Glu Glu Thr Leu Asn Pro Lys Gly
305                 310                 315                 320

Pro Pro Ser Gly Lys Asp Arg Val Lys Lys Gly Ser Tyr Met Cys
            325                 330                 335

His Arg Ser Tyr Cys Tyr Arg Tyr Arg Cys Ala Ala Arg Ser Gln Asn
            340                 345                 350

Thr Pro Asp Ser Ser Ala Ser Asn Leu Gly Phe Arg Cys Ala Ala Asp
        355                 360                 365

Arg Leu Pro Thr Met Asp
    370

<210> SEQ ID NO 58
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 58

Leu Cys Thr Pro Ser Arg Ala Ala Leu Leu Thr Gly Arg
1               5                   10

<210> SEQ ID NO 59
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 59

Asp Tyr Lys Asp Asp Asp Asp Lys
1               5

<210> SEQ ID NO 60
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 60

Leu Ala Thr Pro Ser Arg Ala Ala Leu Leu Thr Gly Arg
1               5                   10

<210> SEQ ID NO 61
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 61

Asp Ser Ser Ser Thr Gly Trp Asn Glu
1               5

<210> SEQ ID NO 62

```
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 62

Gly Ser Leu Cys Thr Pro Ser Arg Gly
1               5

<210> SEQ ID NO 63
<211> LENGTH: 36
<212> TYPE: DNA
<213> ORGANISM: Artificial sequence
<220> FEATURE:
<223> OTHER INFORMATION: Synthetic nucleic acid sequence

<400> SEQUENCE: 63
ctatgctaca tatgctgacc gagttggttg acctgc                              36

<210> SEQ ID NO 64
<211> LENGTH: 33
<212> TYPE: DNA
<213> ORGANISM: Artificial sequence
<220> FEATURE:
<223> OTHER INFORMATION: Synthetic nucleic acid sequence

<400> SEQUENCE: 64
tagcatagct cgagctaccc ggacaccggg tcg                                 33

<210> SEQ ID NO 65
<211> LENGTH: 24
<212> TYPE: DNA
<213> ORGANISM: Artificial sequence
<220> FEATURE:
<223> OTHER INFORMATION: Synthetic nucleic acid sequence

<400> SEQUENCE: 65
caccgccgtg gccgccccgt cccc                                           24

<210> SEQ ID NO 66
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 66
tcactcagcg gctgatccgg                                                20

<210> SEQ ID NO 67
<211> LENGTH: 34
<212> TYPE: DNA
<213> ORGANISM: Artificial sequence
<220> FEATURE:
<223> OTHER INFORMATION: Synthetic nucleic acid sequence

<400> SEQUENCE: 67
ctatgctagg atcccttgag atcacgttgc tcgg                                34

<210> SEQ ID NO 68
<211> LENGTH: 35
<212> TYPE: DNA
<213> ORGANISM: Artificial sequence
<220> FEATURE:
<223> OTHER INFORMATION: Synthetic nucleic acid sequence
```

<400> SEQUENCE: 68
ctatgctact gcagctagcg ccgcgggtgc acctc                                    35

<210> SEQ ID NO 69
<211> LENGTH: 35
<212> TYPE: DNA
<213> ORGANISM: Artificial sequence
<220> FEATURE:
<223> OTHER INFORMATION: Synthetic nucleic acid sequence

<400> SEQUENCE: 69
ctatgctaca tatgacagat ctgattaccg tgaag                                   35

<210> SEQ ID NO 70
<211> LENGTH: 34
<212> TYPE: DNA
<213> ORGANISM: Artificial sequence
<220> FEATURE:
<223> OTHER INFORMATION: Synthetic nucleic acid sequence

<400> SEQUENCE: 70
ctatgctact cgagtcagcc agcgatctcc atcg                                    34

<210> SEQ ID NO 71
<211> LENGTH: 34
<212> TYPE: DNA
<213> ORGANISM: Artificial sequence
<220> FEATURE:
<223> OTHER INFORMATION: Synthetic nucleic acid sequence

<400> SEQUENCE: 71
ctatgctaca tatgccgatg aacacaaac ctcc                                     34

<210> SEQ ID NO 72
<211> LENGTH: 36
<212> TYPE: DNA
<213> ORGANISM: Artificial sequence
<220> FEATURE:
<223> OTHER INFORMATION: Synthetic nucleic acid sequence

<400> SEQUENCE: 72
ctatgctact cgagctacgg cgtcacgatg ttgaag                                  36

<210> SEQ ID NO 73
<211> LENGTH: 34
<212> TYPE: DNA
<213> ORGANISM: Artificial sequence
<220> FEATURE:
<223> OTHER INFORMATION: Synthetic nucleic acid sequence

<400> SEQUENCE: 73
gaccctcaag ggcggcgcac acctgtgcgc gccg                                    34

<210> SEQ ID NO 74
<211> LENGTH: 27
<212> TYPE: DNA
<213> ORGANISM: Artificial sequence
<220> FEATURE:
<223> OTHER INFORMATION: Synthetic nucleic acid sequence

<400> SEQUENCE: 74
tcgcacctga gcgcgccgga gtactgc                                            27

<210> SEQ ID NO 75
<211> LENGTH: 27

<212> TYPE: DNA
<213> ORGANISM: Artificial sequence
<220> FEATURE:
<223> OTHER INFORMATION: Synthetic nucleic acid sequence

<400> SEQUENCE: 75
gcgccggagt acagccaccg ctaccgc                                          27

<210> SEQ ID NO 76
<211> LENGTH: 34
<212> TYPE: DNA
<213> ORGANISM: Artificial sequence
<220> FEATURE:
<223> OTHER INFORMATION: Synthetic nucleic acid sequence

<400> SEQUENCE: 76
caccgcgggc aacgtggcgg aatggtgctc cgac                                  34

<210> SEQ ID NO 77
<211> LENGTH: 34
<212> TYPE: DNA
<213> ORGANISM: Artificial sequence
<220> FEATURE:
<223> OTHER INFORMATION: Synthetic nucleic acid sequence

<400> SEQUENCE: 77
caccgcgggc aacgtgtttg aatggtgctc cgac                                  34

<210> SEQ ID NO 78
<211> LENGTH: 33
<212> TYPE: DNA
<213> ORGANISM: Artificial sequence
<220> FEATURE:
<223> OTHER INFORMATION: Synthetic nucleic acid sequence

<400> SEQUENCE: 78
ggcggctcct acctgtccca cgactcctac tgc                                   33

<210> SEQ ID NO 79
<211> LENGTH: 35
<212> TYPE: DNA
<213> ORGANISM: Artificial sequence
<220> FEATURE:
<223> OTHER INFORMATION: Synthetic nucleic acid sequence

<400> SEQUENCE: 79
gtgccacgac tcctactcca accgctaccg ggtcg                                 35

<210> SEQ ID NO 80
<211> LENGTH: 34
<212> TYPE: DNA
<213> ORGANISM: Artificial sequence
<220> FEATURE:
<223> OTHER INFORMATION: Synthetic nucleic acid sequence

<400> SEQUENCE: 80
ctatgctaaa gcttgaatcg agtgagatat tgcc                                  34

<210> SEQ ID NO 81
<211> LENGTH: 34
<212> TYPE: DNA
<213> ORGANISM: Artificial sequence
<220> FEATURE:
<223> OTHER INFORMATION: Synthetic nucleic acid sequence

<400> SEQUENCE: 81
tagcatagtc tagaatgacg ctcgatcgag aacg       34

<210> SEQ ID NO 82
<211> LENGTH: 35
<212> TYPE: DNA
<213> ORGANISM: Artificial sequence
<220> FEATURE:
<223> OTHER INFORMATION: Synthetic nucleic acid sequence

<400> SEQUENCE: 82
ctatgctatc tagatcctca cagtcgcagg acagc       35

<210> SEQ ID NO 83
<211> LENGTH: 37
<212> TYPE: DNA
<213> ORGANISM: Artificial sequence
<220> FEATURE:
<223> OTHER INFORMATION: Synthetic nucleic acid sequence

<400> SEQUENCE: 83
tagcatagtt aattaatgca ccatctcgtt gctctcg       37

<210> SEQ ID NO 84
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 84

Leu Cys Ser Pro Ser Arg Gly Ser Leu Phe Thr Gly Arg
1               5                   10

<210> SEQ ID NO 85
<211> LENGTH: 19
<212> TYPE: PRT
<213> ORGANISM: Artificial sequence
<220> FEATURE:
<223> OTHER INFORMATION: Synthetic amino acid sequence

<400> SEQUENCE: 85

Ala Ala Ser Leu Cys Thr Pro Ser Arg Ala Ala Phe Leu Thr Gly Arg
1               5                   10                  15

Tyr Pro Val

<210> SEQ ID NO 86
<211> LENGTH: 19
<212> TYPE: PRT
<213> ORGANISM: Artificial sequence
<220> FEATURE:
<223> OTHER INFORMATION: Synthetic amino acid sequence

<400> SEQUENCE: 86

Thr Thr Pro Met Cys Cys Pro Ser Arg Ser Ser Ile Leu Thr Gly Lys
1               5                   10                  15

Tyr Val His

<210> SEQ ID NO 87
<211> LENGTH: 19
<212> TYPE: PRT
<213> ORGANISM: Artificial sequence
<220> FEATURE:
<223> OTHER INFORMATION: Synthetic amino acid sequence

<400> SEQUENCE: 87

Val Asn Gln Leu Cys Thr Pro Thr Arg Ser Ala Phe Met Thr Gly Tyr
1               5                   10                  15

Tyr Pro Phe

<210> SEQ ID NO 88
<211> LENGTH: 19
<212> TYPE: PRT
<213> ORGANISM: Artificial sequence
<220> FEATURE:
<223> OTHER INFORMATION: Synthetic amino acid sequence

<400> SEQUENCE: 88

Thr Ala Pro Leu Cys Thr Pro Ser Arg Gly Ser Leu Phe Thr Gly Arg
1               5                   10                  15

Tyr Pro Gln

<210> SEQ ID NO 89
<211> LENGTH: 19
<212> TYPE: PRT
<213> ORGANISM: Artificial sequence
<220> FEATURE:
<223> OTHER INFORMATION: Synthetic amino acid sequence

<400> SEQUENCE: 89

Cys Ser Pro Val Cys Thr Pro Ala Arg Ala Gly Leu Phe Thr Gly Ile
1               5                   10                  15

Tyr Ala Asn

<210> SEQ ID NO 90
<211> LENGTH: 19
<212> TYPE: PRT
<213> ORGANISM: Artificial sequence
<220> FEATURE:
<223> OTHER INFORMATION: Synthetic amino acid sequence

<400> SEQUENCE: 90

Pro Thr Ala Ile Cys Ile Pro Ala Arg Ala Ser Leu Leu Thr Gly Gln
1               5                   10                  15

Ala Pro Phe

<210> SEQ ID NO 91
<211> LENGTH: 19
<212> TYPE: PRT
<213> ORGANISM: Artificial sequence
<220> FEATURE:
<223> OTHER INFORMATION: Synthetic amino acid sequence

<400> SEQUENCE: 91

Thr Thr Ala Leu Cys Ser Pro Ser Arg Ser Cys Ile Leu Thr Gly Arg
1               5                   10                  15

Asn His His

<210> SEQ ID NO 92
<211> LENGTH: 7
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (3)..(3)
<223> OTHER INFORMATION: The amino acid at this position is a
      formylglycine.

<400> SEQUENCE: 92

```
<210> SEQ ID NO 93
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 93

Pro Leu Cys Thr Pro Ser Arg
1               5

<210> SEQ ID NO 94
<211> LENGTH: 13
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (2)..(2)
<223> OTHER INFORMATION: The amino acid at this position is a
      formylglycine.

<400> SEQUENCE: 94

Leu Xaa Ser Pro Ser Arg Gly Ser Leu Phe Thr Gly Arg
1               5                   10

<210> SEQ ID NO 95
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 95

Leu Ala Thr Pro Ser Arg
1               5

<210> SEQ ID NO 96
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 96

Leu Cys Thr Pro Ser Arg Ala Ala Leu Thr Gly Arg
1               5                   10
```

(Continuation of SEQ ID NO 92:)

Pro Leu Xaa Thr Pro Ser Arg
1               5